US011695155B2

(12) United States Patent
Yoshida et al.

(10) Patent No.: US 11,695,155 B2
(45) Date of Patent: Jul. 4, 2023

(54) NON-AQUEOUS ELECTROLYTIC SOLUTION AND NON-AQUEOUS ELECTROLYTE SECONDARY BATTERY USING THE SAME

(71) Applicants: Mitsubishi Chemical Corporation, Chiyoda-ku (JP); MU IONIC SOLUTIONS CORPORATION, Chiyoda-ku (JP)

(72) Inventors: Hiroaki Yoshida, Inashiki-gun (JP); Daisuke Kawakami, Yokohama (JP); Koji Fukamizu, Inashiki-gun (JP)

(73) Assignees: Mitsubishi Chemical Corporation, Chiyoda-ku (JP); MU IONIC SOLUTIONS CORPORATION, Chiyoda-ku (JP)

( * ) Notice: Subject to any disclaimer, the term of this patent is extended or adjusted under 35 U.S.C. 154(b) by 441 days.

(21) Appl. No.: 16/868,858

(22) Filed: May 7, 2020

(65) Prior Publication Data

US 2020/0263516 A1  Aug. 20, 2020
US 2021/0207452 A2  Jul. 8, 2021

Related U.S. Application Data

(60) Division of application No. 15/185,855, filed on Jun. 17, 2016, now Pat. No. 10,734,680, which is a continuation of application No. PCT/JP2014/083622, filed on Dec. 18, 2014.

(30) Foreign Application Priority Data

Dec. 18, 2013 (JP) .................................. 2013-261591

(51) Int. Cl.
  *H01M 10/0567* (2010.01)
  *C07D 317/36* (2006.01)
  *C07C 303/28* (2006.01)
  *H01M 10/052* (2010.01)
  *H01M 10/0569* (2010.01)
  *E21B 33/12* (2006.01)
  *E21B 33/127* (2006.01)
  *E21B 43/10* (2006.01)
  *H01M 10/0525* (2010.01)
  *C07C 309/65* (2006.01)

(52) U.S. Cl.
  CPC ....... *H01M 10/0567* (2013.01); *C07C 303/28* (2013.01); *C07D 317/36* (2013.01); *E21B 33/127* (2013.01); *E21B 33/1208* (2013.01); *E21B 43/103* (2013.01); *H01M 10/052* (2013.01); *H01M 10/0525* (2013.01); *H01M 10/0569* (2013.01); *C07C 309/65* (2013.01); *E21B 2200/01* (2020.05); *H01M 2300/0017* (2013.01); *H01M 2300/0025* (2013.01)

(58) Field of Classification Search
  None
  See application file for complete search history.

(56) References Cited

U.S. PATENT DOCUMENTS

| 2003/0129500 A1 | 7/2003 | Gan |
| 2004/0023121 A1 | 2/2004 | Nakamura et al. |
| 2007/0117024 A1 | 5/2007 | Nakai et al. |
| 2011/0064998 A1 | 3/2011 | Abe et al. |
| 2012/0171581 A1 | 7/2012 | Abe et al. |
| 2012/0219865 A1 | 8/2012 | Kaneko et al. |
| 2013/0144601 A1 | 6/2013 | Scott et al. |
| 2014/0154587 A1 | 6/2014 | Abe et al. |
| 2014/0199601 A1 | 7/2014 | Onozuka et al. |

FOREIGN PATENT DOCUMENTS

| CN | 103004006 A | 3/2013 |
| EP | 2 495 796 A1 | 9/2012 |
| JP | 2007-141733 | 6/2007 |
| JP | 2011-187235 | 9/2011 |
| JP | 2014-26972 | 2/2014 |
| WO | WO 2009/113545 A1 | 9/2009 |
| WO | WO 2011/034067 A1 | 3/2011 |
| WO | WO 2011/052428 A1 | 5/2011 |
| WO | WO 2013/024748 A1 | 2/2013 |

OTHER PUBLICATIONS

Office Action dated Dec. 11, 2020 in corresponding Korean Patent Applicaton No. 10-2016-7016282 (with English Translation), 13 pages.
International Search Report dated Mar. 31, 2015 in PCT/JP2014/083622, filed on Dec. 18, 2014.
Extended European Search Report dated Sep. 8, 2016 in Patent Application No. 14872647.4.

(Continued)

*Primary Examiner* — Haixia Zhang
(74) *Attorney, Agent, or Firm* — Oblon, McClelland, Maier & Neustadt, L.L.P.

(57) ABSTRACT

A task is to provide a non-aqueous electrolytic solution exhibiting excellent cycle capacity maintaining ratio and excellent low-temperature resistance characteristics and a non-aqueous electrolyte secondary battery using the same. An object of the present invention is to provide a non-aqueous electrolytic solution which improves the cycle capacity maintaining ratio and low-temperature resistance characteristics, and a non-aqueous electrolyte secondary battery using the non-aqueous electrolytic solution. The present invention is a non-aqueous electrolytic solution comprising an electrolyte and a non-aqueous solvent dissolving therein the electrolyte, wherein the non-aqueous electrolytic solution contains a compound represented by formula (1) (wherein X represents an organic group containing a heteroatom, Y represents a sulfur atom, a phosphorus atom, or a carbon atom, n represents an integer of 1 or 2, m represents an integer of 2 to 4, l represents an integer of 1 or 2, and Z represents an organic group having 4 to 12 carbon atoms and optionally having a heteroatom), and a non-aqueous electrolyte secondary battery comprising the non-aqueous electrolytic solution.

7 Claims, No Drawings

(56) References Cited

OTHER PUBLICATIONS

Office Action as received in the counterpart Chinese patent application No. 201480069167.1 dated Mar. 25, 2019 w/English Translation.
European Search Report as received hi the corresponding European Application No. 19168380.4 dated Sep. 30, 2019.
Combined Office Action and Search Report dated Nov. 28, 2017 in Chinese Patent Application No. 201480069167.1 (with partial unedited computer generated English translation and English translation of categories of cited documents), 15 pages.

NON-AQUEOUS ELECTROLYTIC SOLUTION AND NON-AQUEOUS ELECTROLYTE SECONDARY BATTERY USING THE SAME

This application is a divisional application of U.S. application Ser. No. 15/185,855 filed Jun. 17, 2016, allowed and incorporated by reference herein, which is a continuation of PCT/JP2014/083622 filed Dec. 18, 2014 and claims the benefit of JP 2013-261591 filed Dec. 18, 2013.

FIELD OF THE INVENTION

The present invention relates to a non-aqueous electrolytic solution and a non-aqueous electrolyte secondary battery using the same.

BACKGROUND ART

As the industries have recently rapidly progressed, electronic devices are miniaturized and hence secondary batteries for use in the devices are strongly demanded to be further increased in the capacity. For meeting such demands, a lithium secondary battery having a high energy density, as compared to a nickel-cadmium battery and a nickel-hydrogen battery, has been developed, and intensively improved repeatedly in the performance to date.

The components constituting the lithium secondary battery are roughly classified mainly into a positive electrode, a negative electrode, a separator, and an electrolytic solution. In these components, as the electrolytic solution, a non-aqueous electrolytic solution is generally used, wherein the non-aqueous electrolytic solution is obtained by dissolving an electrolyte, such as $LiPF_6$, $LiBF_4$, $LiClO_4$, $LiCF_3SO_3$, $LiAsF_6$, $LiN(CF_3SO_2)_2$, or $LiCF_3(CF_2)_3SO_3$, in a non-aqueous solvent, e.g., a cyclic carbonate, such as ethylene carbonate or propylene carbonate; a linear carbonate, such as dimethyl carbonate, diethyl carbonate, or ethylmethyl carbonate; a cyclic ester, such as γ-butyrolactone or γ-valerolactone; or a linear ester, such as methyl acetate or methyl propionate.

In recent years, there are problems to be solved on a global scale, such as environmental problems and energy problems, and lithium secondary batteries are expected to be applied to large-size power sources including a car power source and a stationary power source. However, the batteries applied to such uses are generally presumed to be used in an environment exposed to the air, and therefore, in the development of the batteries, efforts are focused on the battery characteristics in an environment at low temperatures, such as sub-zero temperatures, particularly on the low-temperature resistance characteristics. Further, the batteries are required to have more excellent life performance than conventional lithium secondary batteries due to the uses of the batteries.

As one of attempts to further improve various characteristics of the lithium secondary battery, a method of adding an arbitrary compound to the above-mentioned electrolytic solution has been attempted.

For example, patent documents 1 and 2 have proposed a technique of using a hydroxy acid derivative in a non-aqueous electrolyte when using a carbon material in the negative electrode. Further, patent documents 3 and 4 have proposed a technique of adding a specific sulfonic ester to a non-aqueous electrolyte.

PRIOR ART REFERENCES

Patent Documents

Patent document 1: International Publication No. WO2009/113545
Patent document 2: International Publication No. WO 2011/034067
Patent document 3: Japanese Unexamined Patent Publication No. 2011-187235
Patent document 4: Japanese Unexamined Patent Publication No. 2014-26972

SUMMARY OF THE INVENTION

Problems to be Solved by the Invention

As mentioned above, attempts have been made to improve the battery in life performance and low-temperature resistance characteristics. However, satisfactory battery characteristics have not yet been achieved, and further improvements are desired.

In view of the above-mentioned background art, the present invention has been made, and an object of the present invention is to provide a non-aqueous electrolytic solution exhibiting excellent cycle capacity maintaining ratio and excellent low-temperature resistance characteristics, and a non-aqueous electrolyte secondary battery using the same.

Means for Solving the Problems

The present inventors have conducted extensive and intensive studies with a view toward solving the above-mentioned problems. As a result, it has been found that, when the non-aqueous electrolytic solution contains a specific compound, both the cycle capacity maintaining ratio and the low-temperature resistance characteristics of the non-aqueous electrolyte secondary battery are improved at the same time, and the present invention has been completed. Specifically, the gist of the present invention is as follows.

(a) A non-aqueous electrolytic solution comprising an electrolyte and a non-aqueous solvent dissolving therein the electrolyte, wherein the non-aqueous electrolytic solution contains a compound represented by the following formula (1):

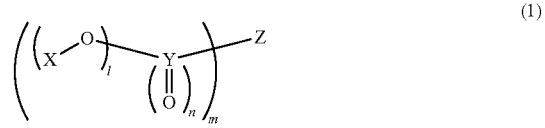

wherein:
X represents an organic group containing a heteroatom, the organic group having at least one oxygen atom as the heteroatom,
Y represents a sulfur atom, a phosphorus atom, or a carbon atom,
n represents an integer of 1 or 2, m represents an integer of 2 to 4, and l represents an integer of 1 or 2, and
Z represents an organic group having 4 to 12 carbon atoms and optionally having a heteroatom.

(b) The non-aqueous electrolytic solution according to item (a) above, wherein the X is an organic group containing a carbonyl group.

(c) The non-aqueous electrolytic solution according to item (a) or (b) above, wherein the Y is a sulfur atom.

(d) The non-aqueous electrolytic solution according to any one of items (a) to (c) above, wherein the Z is an alkylene group having 4 to 6 carbon atoms.

(e) The non-aqueous electrolytic solution according to any one of items (a) to (d) above, wherein the at least one compound represented by the formula (1) is contained in an amount of 0.01 to 5% by mass, based on the mass of the non-aqueous electrolytic solution (100% by mass).

(f) The non-aqueous electrolytic solution according to any one of items (a) to (e) above, which further contains a cyclic carbonate having an unsaturated bond.

(g) A non-aqueous electrolyte secondary battery comprising a negative electrode and a positive electrode each being capable of having occluded therein and releasing metal ions, and the non-aqueous electrolytic solution according to any one of items (a) to (f) above.

(h) The non-aqueous electrolyte secondary battery according to item (g) above, wherein the positive electrode capable of having occluded therein and releasing metal ions comprises at least one layer transition metal oxide.

(i) The non-aqueous electrolyte secondary battery according to item (g) above, wherein the negative electrode capable of having occluded therein and releasing metal ions comprises at least one carbon compound.

(j) A method for producing a sulfonic ester represented by the following formula (10):

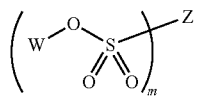

(10)

wherein:
W represents an organic group containing a heteroatom, the organic group having at least one oxygen atom as the heteroatom,
m represents an integer of 2 to 4, and
Z represents an organic group having 4 to 12 carbon atoms and optionally having a heteroatom,
the method comprising the steps of:
reacting a sulfonyl chloride represented by the following formula (11):

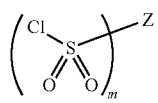

(11)

wherein Z and m are as defined for the formula (10)
and a compound having an alcoholic hydroxyl group and being represented by the following formula (12):

 (12)

wherein W is as defined for the formula (10)
with each other; and
taking out a sulfonic ester represented by the formula (10) in the form of a solid by crystal deposition.

(k) The method for producing a sulfonic ester according to item (j) above, wherein the crystal deposition is conducted by reducing the temperature of a solution containing the sulfonic ester represented by the formula (10).

(l) The method for producing a sulfonic ester according to item (k) above, wherein the solution containing the sulfonic ester represented by the formula (10) is a methanol solution.

(m) The method for producing a sulfonic ester according to any one of items (j) to (k) above, wherein the crystal deposition is conducted under temperature conditions at 20° C. or lower.

(n) The method for producing a sulfonic ester according to any one of items (j) to (m) above, wherein Z in the formula (10) is an organic group having a linear structure.

(o) The method for producing a sulfonic ester according to any one of items (j) to (o) above, wherein the sulfonyl chloride represented by the formula (11) is represented by the following formula (21):

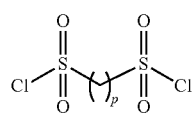

(21)

wherein p represents an integer of 4 to 6.

(p) The method for producing a sulfonic ester according to any one of items (j) to (o) above, wherein the compound having an alcoholic hydroxyl group and being represented by the formula (12) is represented by the following formula (22):

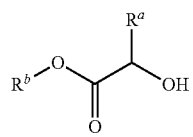

(22)

wherein:
$R^a$ independently represents an alkyl group having 1 to 4 carbon atoms, and
$R^b$ independently represents an alkyl group having 1 to 4 carbon atoms.

(q) The method for producing a sulfonic ester according to any one of items (j) to (p) above, wherein the compound having an alcoholic hydroxyl group and being represented by the formula (12) is glycerol carbonate.

(r) A compound which is represented by the following formula (20):

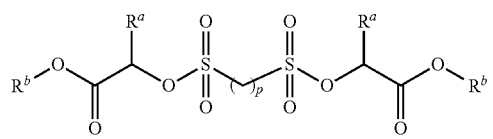

(20)

wherein:
$R^a$ each occurrence independently represents an alkyl group having 1 to 4 carbon atoms,
$R^b$ each occurrence independently represents an alkyl group having 1 to 4 carbon atoms, and
p represents an integer of 4 to 6.

(s) A compound which is represented by the following formula (30):

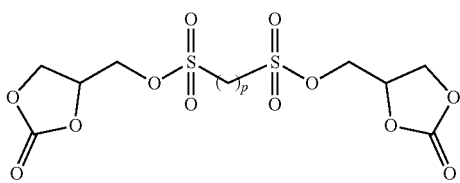

(30)

wherein p represents an integer of 4 to 6.

Effects of the Invention

One of the characteristic features of the present invention resides in that a compound represented by the formula (1) is used in the non-aqueous electrolytic solution. When the non-aqueous electrolytic solution of the present invention is used in a non-aqueous electrolyte secondary battery, the compound represented by the formula (1) is electrochemically reduced on the surface of the negative electrode, so that a metal salt (for example, a lithium salt) derived from the compound is formed. The salt is considered to improve the negative electrode film in thermal stability, suppressing a side reaction caused on the negative electrode due to the solvent.

That is, by using the non-aqueous electrolytic solution of the present invention, the non-aqueous electrolyte secondary battery is expected to be improved in the cycle capacity maintaining ratio and prevented from suffering a lowering of the low-temperature resistance characteristics due to the side reaction.

MODE FOR CARRYING OUT THE INVENTION

Hereinbelow, embodiments of the present invention will be described, but the present invention is not limited to the following embodiments, and can be arbitrarily changed or modified as long as there is no departure from the gist of the present invention.

1. Non-Aqueous Electrolytic Solution

The present invention is directed to a non-aqueous electrolytic solution comprising an electrolyte (for example, a lithium salt) and a non-aqueous solvent dissolving therein the electrolyte, wherein the non-aqueous electrolytic solution contains a compound represented by the formula (1).

1-1. Electrolyte

As the electrolyte, typically, there can be mentioned a lithium salt, and the electrolyte is not limited to a lithium salt, and may be a metal salt, such as a sodium, potassium, calcium, or barium salt. With respect to the lithium salt, there is no particular limitation as long as it is known to be used in the applications of non-aqueous electrolytic solution. Specifically, there can be mentioned the followings.

Examples include inorganic lithium salts, such as $LiPF_6$, $LiBF_4$, $LiClO_4$, $LiAlF_4$, $LiSbF_6$, $LiTaF_6$, and $LiWF_7$; lithium tungstates, such as $LiWOF_5$; lithium carboxylates, such as $HCO_2Li$, $CH_3CO_2Li$, $CH_2FCO_2Li$, $CHF_2CO_2Li$, $CF_3CO_2Li$, $CF_3CH_2CO_2Li$, $CF_3CF_2CO_2Li$, $CF_3CF_2CF_2CO_2Li$, and $CF_3CF_2CF_2CF_2CO_2Li$; lithium sulfonates, such as $FSO_3Li$, $CH_3SO_3Li$, $CH_2FSO_3Li$, $CHF_2SO_3Li$, $CF_3SO_3Li$, $CF_3CF_2SO_3Li$, $CF_3CF_2CF_2SO_3Li$, and $CF_3CF_2CF_2CF_2SO_3Li$; lithium imide salts, such as $LiN(FCO)_2$, $LiN(FCO)(FSO_2)$, $LiN(FSO_2)_2$, $LiN(FSO_2)$ $(CF_3SO_2)$, $LiN(CF_3SO_2)_2$, $LiN(C_2FSO_2)_2$, lithium cyclic 1,2-perfluoroethanedisulfonyl imide, lithium cyclic 1,3-perfluoropropanedisulfonyl imide, and $LiN(CF_3SO_2)$ $(C_4F_9SO_2)$; lithium methide salts, such as $LiC(FSO_2)_3$, $LiC(CF_3SO_2)_3$, and $LiC(C_2F_5SO_2)_3$; lithium oxalatoborates, such as lithium difluorooxalatoborate and lithium bis(oxalato)borate; lithium oxalatophosphates, such as lithium tetrafluorooxalatophosphate, lithium difluorobis(oxalato)phosphate, and lithium tris(oxalato)phosphate; and fluorine-containing organolithium salts, such as $LiPF_4(CF_3)_2$, $LiPF_4$ $(C_2F_5)_2$, $LiPF_4(CF_3SO_2)_2$, $LiPF_4(C_2F_5SO_2)_2$, $LiBF_3CF_3$, $LiBF_3C_2F_5$, $LiBF_3C_3F_7$, $LiBF_2(CF_3)_2$, $LiBF_2(C_2F_5)_2$, $LiBF_2(CF_3SO_2)_2$, and $LiBF_2(C_2F_5SO_2)_2$.

Of these, from the viewpoint of the effects of improving, for example, the output characteristics, high-rate charge-discharge characteristics, high-temperature storage characteristics, and cycle characteristics, especially preferred are $LiPF_6$, $LiBF_4$, $LiSbF_6$, $LiTaF_6$, $FSO_3Li$, $CF_3SO_3Li$, $LiN$ $(FSO_2)_2$, $LiN(FSO_2)(CF_3SO_2)$, $LiN(CF_3SO_2)_2$, $LiN$ $(C_2F_5SO_2)_2$, lithium cyclic 1,2-perfluoroethanedisulfonyl imide, lithium cyclic 1,3-perfluoropropanedisulfonyl imide, $LiC(FSO_2)_3$, $LiC(CF_3SO_2)_3$, $LiC(C_2F_5SO_2)_3$, lithium bisoxalatoborate, lithium difluorooxalatoborate, lithium tetrafluorooxalatophosphate, lithium difluorobisoxalatophosphate, $LiBF_3CF_3$, $LiBF_3C_2F_5$, $LiPF_3(CF_3)_3$, and $LiPF_3(C_2F_5)_3$.

These lithium salts may be used individually or in combination. When two or more types of the lithium salts are used in combination, as preferred examples of combinations of the lithium salts, there can be mentioned a combination of $LiPF_6$ and $LiBF_4$ and a combination of $LiPF_6$ and $FSO_3Li$, which exhibit effects of improving the load characteristics and cycle characteristics. In this case, the concentration of $LiBF_4$ or $FSO_3Li$ in the non-aqueous electrolytic solution (100% by mass) is not limited, and is arbitrary as long as the effects of the present invention are not markedly sacrificed, and the concentration of $LiBF_4$ or $FSO_3Li$ is generally 0.01% by mass or more, preferably 0.1% by mass or more, and is generally 30% by mass or less, preferably 20% by mass or less, based on the mass of the non-aqueous electrolytic solution of the present invention. Further, the concentration of $LiPF_6$ is not limited, and is arbitrary as long as the effects of the present invention are not markedly sacrificed, and the $LiPF_6$ concentration is generally 0.5 mol/L or more, preferably 0.8 mol/L or more, and is generally 3 mol/L or less, preferably 2 mol/L or less.

As another example, there can be mentioned the use of an inorganic lithium salt and an organolithium salt in combination, which exhibits an effect of suppressing the deterioration due to storage at high temperatures. As the organolithium salt, preferred are, for example, $CF_3SO_3Li$, $LiN$ $(FSO_2)_2$, $LiN(FSO_2)(CF_3SO_2)$, $LiN(CF_3SO_2)_2$, $LiN$ $(C_2F_5SO_2)_2$, lithium cyclic 1,2-perfluoroethanedisulfonyl imide, lithium cyclic 1,3-perfluoropropanedisulfonyl imide, $LiC(FSO_2)_3$, $LiC(CF_3SO_2)_3$, $LiC(C_2F_5SO_2)_3$, lithium bisoxalatoborate, lithium difluorooxalatoborate, lithium tetrafluorooxalatophosphate, lithium difluorobisoxalatophosphate, $LiBF_3CF_3$, $LiBF_3C_2F_5$, $LiPF_3(CF_3)_3$, and $LiPF_3(C_2F_5)_3$. In this case, the proportion of the organolithium salt to the non-aqueous electrolytic solution (100% by mass) is preferably 0.1% by mass or more, especially preferably 0.5% by mass or more, and is preferably 30% by mass or less, especially preferably 20% by mass or less. The concentration of the inorganic lithium salt is not limited, and is arbitrary as long as the effects of the present invention are not markedly sacrificed, and the concentration of the inorganic lithium salt is generally 0.1% by mass or more, preferably 0.2% by mass or more, and is generally 10% by mass or less, preferably 5% by mass or less, based on the mass of the non-aqueous electrolytic solution of the present invention.

With respect to the concentration of the lithium salt in the non-aqueous electrolytic solution, there is no particular limitation as long as the effects of the present invention are not sacrificed. From the viewpoint of achieving the electrical conductivity of the electrolytic solution in an advantageous range to secure excellent battery performance, the total lithium molar concentration of the non-aqueous electrolytic solution is preferably 0.3 mol/L or more, more preferably 0.4 mol/L or more, further preferably 0.5 mol/L or more, and is preferably 3 mol/L or less, more preferably 2.5 mol/L or less, further preferably 2.0 mol/L or less. When the total lithium molar concentration is in the above range, the amount of lithium which is a charged particle is not too small, and further the viscosity of the electrolytic solution can be in an appropriate range, making it easy to secure excellent electrical conductivity.

1-2. Non-Aqueous Solvent

As the non-aqueous solvent, for example, a cyclic carbonate, a linear carbonate, a cyclic or linear carboxylate, an ether compound, or a sulfone compound can be used.

<Cyclic Carbonate>

Examples of cyclic carbonates include those having an alkylene group having 2 to 4 carbon atoms.

Specific examples of cyclic carbonates having 2 to 4 carbon atoms include alkylene carbonates having an alkylene group having 2 to 4 carbon atoms, such as ethylene carbonate, propylene carbonate, and butylene carbonate. Of these, ethylene carbonate and propylene carbonate are especially preferred from the viewpoint of the improvement of the battery characteristics due to the improvement of the degree of dissociation of lithium ions.

The cyclic carbonates may be used individually, or two or more types of the cyclic carbonates may be used in an arbitrary combination and in an arbitrary ratio.

With respect to the amount of the cyclic carbonate incorporated, there is no particular limitation, and the amount is arbitrary as long as the effects of the present invention are not markedly sacrificed. However, when a single type of the cyclic carbonate is used, the lower limit of the amount of the cyclic carbonate incorporated is 5% by volume or more, more preferably 10% by volume or more, based on the volume of the non-aqueous solvent (100% by volume). When the lower limit is in the above range, a lowering of the electrical conductivity due to the lowering of the permittivity of the non-aqueous electrolytic solution can be avoided, so that the large-current discharge characteristics, the stability to negative electrode, and the cycle characteristics of the non-aqueous electrolyte secondary battery can be easily in their respective advantageous ranges. The upper limit is 95% by volume or less, more preferably 90% by volume or less, further preferably 85% by volume or less. When the upper limit is in the above range, the viscosity of the non-aqueous electrolytic solution can be in an appropriate range, so that a lowering of the ionic conductivity is suppressed, and further the load characteristics of the non-aqueous electrolyte secondary battery can be easily in an advantageous range.

When two or more types of the cyclic carbonates are used in an arbitrary combination, as a preferred example of a combination of the cyclic carbonates, there can be mentioned a combination of ethylene carbonate and propylene carbonate. In this case, the volume ratio of ethylene carbonate and propylene carbonate is preferably 99:1 to 40:60, especially preferably 95:5 to 50:50. Further, the amount of propylene carbonate in the all non-aqueous solvents is 0.1% by volume or more, preferably 1% by volume or more, more preferably 2% by volume or more, and is generally 20% by volume or less, preferably 8% by volume or less, more preferably 5% by volume or less. When propylene carbonate is contained in an amount in the above range, further excellent low-temperature characteristics can be advantageously obtained.

<Linear Carbonate>

As the linear carbonate, preferred is a linear carbonate having 3 to 7 carbon atoms.

Specific examples of linear carbonates having 3 to 7 carbon atoms include dimethyl carbonate, diethyl carbonate, di-n-propyl carbonate, diisopropyl carbonate, n-propylisopropyl carbonate, ethylmethyl carbonate, methyl-n-propyl carbonate, n-butylmethyl carbonate, isobutylmethyl carbonate, t-butylmethyl carbonate, ethyl-n-propyl carbonate, n-butylethyl carbonate, isobutylethyl carbonate, and t-butylethyl carbonate.

Of these, preferred are dimethyl carbonate, diethyl carbonate, di-n-propyl carbonate, diisopropyl carbonate, n-propylisopropyl carbonate, ethylmethyl carbonate, and methyl-n-propyl carbonate, and especially preferred are dimethyl carbonate, diethyl carbonate, and ethylmethyl carbonate.

Further, a linear carbonate having a fluorine atom (hereinafter, frequently referred to simply as "fluorinated linear carbonate") can be preferably used. With respect to the number of the fluorine atom(s) of the fluorinated linear carbonate, there is no particular limitation as long as the number is 1 or more, but the number of the fluorine atom(s) is generally 6 or less, preferably 4 or less. When the fluorinated linear carbonate has a plurality of fluorine atoms, the fluorine atoms may be either bonded to the same carbon or individually bonded to different carbon atoms. Examples of fluorinated linear carbonates include fluorinated dimethyl carbonate derivatives, fluorinated ethylmethyl carbonate derivatives, and fluorinated diethyl carbonate derivatives.

Examples of fluorinated dimethyl carbonate derivatives include fluoromethylmethyl carbonate, difluoromethylmethyl carbonate, trifluoromethylmethyl carbonate, bis(fluoromethyl) carbonate, bis(difluoro)methyl carbonate, and bis(trifluoromethyl) carbonate.

Examples of fluorinated ethylmethyl carbonate derivatives include 2-fluoroethylmethyl carbonate, ethylfluoromethyl carbonate, 2,2-difluoroethylmethyl carbonate, 2-fluoroethylfluoromethyl carbonate, ethyldifluoromethyl carbonate, 2,2,2-trifluoroethylmethyl carbonate, 2,2-difluoroethylfluoromethyl carbonate, 2-fluoroethyldifluoromethyl carbonate, and ethyltrifluoromethyl carbonate.

Examples of fluorinated diethyl carbonate derivatives include ethyl-(2-fluoroethyl) carbonate, ethyl-(2,2-difluoroethyl) carbonate, bis(2-fluoroethyl) carbonate, ethyl-(2,2,2-trifluoroethyl) carbonate, 2,2-difluoroethyl-2'-fluoroethyl carbonate, bis(2,2-difluoroethyl) carbonate, 2,2,2-trifluoroethyl-2'-fluoroethyl carbonate, 2,2,2-trifluoroethyl-2',2'-difluoroethyl carbonate, and bis(2,2,2-trifluoroethyl) carbonate.

The linear carbonates may be used individually, or two or more types of the linear carbonates may be used in an arbitrary combination and in an arbitrary ratio.

The amount of the linear carbonate incorporated is preferably 5% by volume or more, more preferably 10% by volume or more, further preferably 15% by volume or more, based on the volume of the non-aqueous solvent (100% by volume). When the lower limit of the amount of the linear carbonate incorporated is set to be in the above range, the viscosity of the non-aqueous electrolytic solution can be in an appropriate range, so that a lowering of the ionic conductivity is suppressed, and further the large-current discharge characteristics of the non-aqueous electrolyte secondary battery can be easily in an advantageous range. Further, the amount of the linear carbonate incorporated is preferably 90% by volume or less, more preferably 85% by volume or less, based on the volume of the non-aqueous solvent (100% by volume). When the upper limit of the amount of the linear carbonate incorporated is set to be in the above range, a lowering of the electrical conductivity due to the lowering of the permittivity of the non-aqueous electrolytic solution can be avoided, so that the large-current discharge characteristics of the non-aqueous electrolyte secondary battery can be easily in an advantageous range.

<Cyclic Carboxylate>

As examples of cyclic carboxylates, there can be mentioned ones having a structural formula in which the total number of carbon atoms is 3 to 12.

Specific examples include gamma-butyrolactone, gamma-valerolactone, gamma-caprolactone, and epsilon-caprolactone. Of these, gamma-butyrolactone is especially preferred from the viewpoint of the improvement of the battery characteristics due to the improvement of the degree of dissociation of lithium ions.

The amount of the cyclic carboxylate incorporated is preferably 5% by volume or more, more preferably 10% by volume or more, based on the volume of the non-aqueous solvent (100% by volume). When the amount of the cyclic carboxylate incorporated is in the above range, the electrical conductivity of the non-aqueous electrolytic solution is improved, making it easy to improve the large-current discharge characteristics of the non-aqueous electrolyte secondary battery. Further, the amount of the cyclic carboxylate incorporated is preferably 50% by volume or less, more preferably 40% by volume or less. When the upper limit of the amount of the cyclic carboxylate incorporated is set to be in the above range, the viscosity of the non-aqueous electrolytic solution can be in an appropriate range, so that a lowering of the electrical conductivity can be avoided and an increase of the negative electrode resistance can be suppressed, and thus the large-current discharge characteristics of the non-aqueous electrolyte secondary battery can be easily in an advantageous range.

<Linear Carboxylate>

As examples of linear carboxylates, there can be mentioned ones having a structural formula in which the total number of carbon atoms is 3 to 7.

Specific examples include methyl acetate, ethyl acetate, n-propyl acetate, isopropyl acetate, n-butyl acetate, isobutyl acetate, t-butyl acetate, methyl propionate, ethyl propionate, n-propyl propionate, isopropyl propionate, n-butyl propionate, isobutyl propionate, t-butyl propionate, methyl butyrate, ethyl butyrate, n-propyl butyrate, isopropyl butyrate, methyl isobutyrate, ethyl isobutyrate, n-propyl isobutyrate, and isopropyl isobutyrate.

Of these, preferred are methyl acetate, ethyl acetate, n-propyl acetate, n-butyl acetate, methyl propionate, ethyl propionate, n-propyl propionate, isopropyl propionate, methyl butyrate, and ethyl butyrate from the viewpoint of the improvement of the ionic conductivity due to the lowering of the viscosity.

The amount of the linear carboxylate incorporated is preferably 10% by volume or more, more preferably 15% by volume or more, based on the volume of the non-aqueous solvent (100% by volume). When the lower limit of the amount of the linear carboxylate incorporated is set to be in the above range, the electrical conductivity of the non-aqueous electrolytic solution can be improved, making it easy to improve the large-current discharge characteristics of the non-aqueous electrolyte secondary battery. Further, the amount of the linear carboxylate incorporated is preferably 60, by volume or less, more preferably 50% by volume or less, based on the volume of the non-aqueous solvent (100% by volume). When the upper limit of the amount of the linear carboxylate incorporated is set to be in the above range, an increase of the negative electrode resistance can be suppressed, so that the large-current discharge characteristics and the cycle characteristics of the non-aqueous electrolyte secondary battery can be easily in their respective advantageous ranges.

<Ether Compound>

As the ether compound, preferred are a linear ether having 3 to 10 carbon atoms, in which part of hydrogens are optionally replaced by fluorine, and a cyclic ether having 3 to 6 carbon atoms.

Examples of linear ethers having 3 to 10 carbon atoms include diethyl ether, di(2-fluoroethyl) ether, di(2,2-difluoroethyl) ether, di(2,2,2-trifluoroethyl) ether, ethyl(2-fluoroethyl) ether, ethyl(2,2,2-trifluoroethyl) ether, ethyl(1,1,2,2-tetrafluoroethyl) ether, (2-fluoroethyl)(2,2,2-trifluoroethyl) ether, (2-fluoroethyl)(1,1,2,2-tetrafluoroethyl) ether, (2,2,2-trifluoroethyl)(1,1,2,2-tetrafluoroethyl) ether, ethyl-n-propyl ether, ethyl(3-fluoro-n-propyl) ether, ethyl(3,3,3-trifluoro-n-propyl) ether, ethyl(2,2,3,3-tetrafluoro-n-propyl) ether, ethyl (2,2,3,3,3-pentafluoro-n-propyl) ether, 2-fluoroethyl-n-propyl ether, (2-fluoroethyl)(3-fluoro-n-propyl) ether, (2-fluoroethyl)(3,3,3-trifluoro-n-propyl) ether, (2-fluoroethyl)(2,2,3,3-tetrafluoro-n-propyl) ether, (2-fluoroethyl)(2,2,3,3,3-pentafluoro-n-propyl) ether, 2,2,2-trifluoroethyl-n-propyl ether, (2,2,2-trifluoroethyl)(3-fluoro-n-propyl) ether, (2,2,2-trifluoroethyl)(3,3,3-trifluoro-n-propyl) ether, (2,2,2-trifluoroethyl)(2,2,3,3-tetrafluoro-n-propyl) ether, (2,2,2-trifluoroethyl)(2,2,3,3,3-pentafluoro-n-propyl) ether, 1,1,2,2-tetrafluoroethyl-n-propyl ether, (1,1,2,2-tetrafluoroethyl)(3-fluoro-n-propyl) ether, (1,1,2,2-tetrafluoroethyl)(3,3,3-trifluoro-n-propyl) ether, (1,1,2,2-tetrafluoroethyl)(2,2,3,3-tetrafluoro-n-propyl) ether, (1,1,2,2-tetrafluoroethyl)(2,2,3,3,3-pentafluoro-n-propyl) ether, di-n-propyl ether, (n-propyl)(3-fluoro-n-propyl) ether, (n-propyl)(3,3,3-trifluoro-n-propyl) ether, (n-propyl)(2,2,3,3-tetrafluoro-n-propyl) ether, (n-propyl)(2,2,3,3,3-pentafluoro-n-propyl) ether, di(3-fluoro-n-propyl) ether, (3-fluoro-n-propyl)(3,3,3-trifluoro-n-propyl) ether, (3-fluoro-n-propyl)(2,2,3,3-tetrafluoro-n-propyl) ether, (3-fluoro-n-propyl)(2,2,3,3,3-pentafluoro-n-propyl) ether, di(3,3,3-trifluoro-n-propyl) ether, (3,3,3-trifluoro-n-propyl)(2,2,3,3-tetrafluoro-n-propyl) ether, (3,3,3-trifluoro-n-propyl)(2,2,3,3,3-pentafluoro-n-propyl) ether, di(2,2,3,3-tetrafluoro-n-propyl) ether, (2,2,3,3-tetrafluoro-n-propyl)(2,2,3,3,3-pentafluoro-n-propyl) ether, di(2,2,3,3,3-pentafluoro-n-propyl) ether, di-n-butyl ether, dimethoxymethane, methoxyethoxymethane, methoxy(2-fluoroethoxy)methane, methoxy(2,2,2-trifluoroethoxy)methane, methoxy(1,1,2,2-tetrafluoroethoxy)methane, diethoxymethane, ethoxy(2-fluoroethoxy)methane, ethoxy(2,2,2-trifluoroethoxy)methane, ethoxy(1,1,2,2-tetrafluoroethoxy)methane, di(2-fluoroethoxy)methane. (2-fluoroethoxy)(2,2,2-trifluoroethoxy)methane, (2-fluoroethoxy)(1,1,2,2-tetrafluoroethoxy)methane, di(2,2,2-trifluoroethoxy)methane, (2,2,2-trifluoroethoxy)(1,1,2,2-tetrafluoroethoxy)methane, di(1,1,2,2-tetrafluoroethoxy)methane, dimethoxyethane, methoxyethoxyethane, methoxy(2-fluoroethoxy)ethane, methoxy(2,2,2-trifluoroethoxy)ethane, methoxy(1,1,2,2-tetrafluoroethoxy)ethane, diethoxyethane, ethoxy(2-fluoroethoxy)ethane, ethoxy(2,2,2-trifluoroethoxy)ethane, ethoxy(1,1,2,2-tetrafluoroethoxy)ethane, di(2-fluoroethoxy)ethane, (2-fluoroethoxy)(2,2,2-trifluoroethoxy)ethane, (2-fluoroethoxy)(1,1,2,2-tetrafluoroethoxy)ethane, di(2,2,2-trifluoroethoxy)ethane, (2,2,2-trifluoroethoxy)(1,1,2,2-tetrafluoroethoxy)ethane, di(1,1,2,2-tetrafluoroethoxy)ethane, ethylene glycol di-n-propyl ether, ethylene glycol di-n-butyl ether, and diethylene glycol dimethyl ether.

Examples of cyclic ethers having 3 to 6 carbon atoms include tetrahydrofuran, 2-methyltetrahydrofuran, 3-methyltetrahydrofuran, 1,3-dioxane, 2-methyl-1,3-dioxane, 4-methyl-1,3-dioxane, 1,4-dioxane, and fluorinated compounds thereof.

Of these, preferred are dimethoxymethane, diethoxymethane, ethoxymethoxymethane, ethylene glycol di-n-propyl ether, ethylene glycol di-n-butyl ether, and diethylene glycol dimethyl ether from the viewpoint of exhibiting high solvating ability for lithium ions to improve the ion dissociation properties, and especially preferred are dimethoxymethane, diethoxymethane, and ethoxymethoxymethane because they have low viscosity and exhibit high ionic conductivity.

The amount of the ether compound incorporated is preferably 5% by volume or more, more preferably 10% by volume or more, further preferably 15% by volume or more, and is preferably 70% by volume or less, more preferably 60% by volume or less, further preferably 50% by volume or less, based on the volume of the non-aqueous solvent (100% by volume). When the amount of the ether compound incorporated is in the above range, the ionic conductivity improvement effect due to the improvement of the degree of dissociation of lithium ions and the lowering of the viscosity obtained by the linear ether can be easily secured, and, when the negative electrode active material is a carbonaceous material, it is easy to avoid a problem, such as a lowering of the capacity due to co-insertion of the linear ether together with lithium ions.

<Sulfone Compound>

As the sulfone compound, preferred are a cyclic sulfone having 3 to 6 carbon atoms and a linear sulfone having 2 to 6 carbon atoms. The number of the sulfonyl group(s) per molecule is preferably 1 or 2.

Examples of cyclic sulfones having 3 to 6 carbon atoms include trimethylene sulfones, tetramethylene sulfones, and hexamethylene sulfones, which are monosulfone compounds; and trimethylene disulfones, tetramethylene disulfones, and hexamethylene disulfones, which are disulfone compounds. Of these, from the viewpoint of the permittivity and viscosity, more preferred are tetramethylene sulfones, tetramethylene disulfones, hexamethylene sulfones, and hexamethylene disulfones, and especially preferred are tetramethylene sulfones (sulfolanes).

As the sulfolanes, preferred are sulfolane and/or sulfolane derivatives (hereinafter, frequently referred to simply as "sulfolanes" including sulfolane). Preferred sulfolane derivatives are ones in which one or more hydrogen atoms bonded onto the carbon atoms constituting the sulfolane ring are replaced by a fluorine atom or an alkyl group.

Of these, from the viewpoint of exhibiting high ionic conductivity to achieve high input and output, preferred are 2-methylsulfolane, 3-methylsulfolane, 2-fluorosulfolane, 3-fluorosulfolane, 2,2-difluorosulfolane, 2,3-difluorosulfolane, 2,4-difluorosulfolane, 2,5-difluorosulfolane, 3,4-difluorosulfolane, 2-fluoro-3-methylsulfolane, 2-fluoro-2-methylsulfolane, 3-fluoro-3-methylsulfolane, 3-fluoro-2-methylsulfolane, 4-fluoro-3-methylsulfolane, 4-fluoro-2-methylsulfolane, 5-fluoro-3-methylsulfolane, 5-fluoro-2-methylsulfolane, 2-fluoromethylsulfolane, 3-fluoromethylsulfolane, 2-difluoromethylsulfolane, 3-difluoromethylsulfolane, 2-trifluoromethylsulfolane, 3-trifluoromethylsulfolane, 2-fluoro-3-(trifluoromethyl)sulfolane, 3-fluoro-3-(trifluoromethyl)sulfolane, 4-fluoro-3-(trifluoromethyl)sulfolane, and 5-fluoro-3-(trifluoromethyl)sulfolane.

Examples of linear sulfones having 2 to 6 carbon atoms include dimethyl sulfone, ethylmethyl sulfone, diethyl sulfone, n-propylmethyl sulfone, n-propylethyl sulfone, di-n-propyl sulfone, isopropylmethyl sulfone, isopropylethyl sulfone, diisopropyl sulfone, n-butylmethyl sulfone, n-butylethyl sulfone, t-butylmethyl sulfone, t-butylethyl sulfone, monofluoromethylmethyl sulfone, difluoromethylmethyl sulfone, trifluoromethylmethyl sulfone, monofluoroethylmethyl sulfone, difluoroethylmethyl sulfone, trifluoroethylmethyl sulfone, pentafluoroethylmethyl sulfone, ethylmonofluoromethyl sulfone, ethyldifluoromethyl sulfone, ethyltrifluoromethyl sulfone, perfluoroethylmethyl sulfone, ethyltrifluoroethyl sulfone, ethylpentafluoroethyl sulfone, di(trifluoroethyl) sulfone, perfluorodiethyl sulfone, fluoromethyl-n-propyl sulfone, difluoromethyl-n-propyl sulfone, trifluoromethyl-n-propyl sulfone, fluoromethylisopropyl sulfone, difluoromethylisopropyl sulfone, trifluoromethylisopropyl sulfone, trifluoroethyl-n-propyl sulfone, trifluoroethylisopropyl sulfone, pentafluoroethyl-n-propyl sulfone, pentafluoroethylisopropyl sulfone, trifluoroethyl-n-butyl sulfone, trifluoroethyl-t-butyl sulfone, pentafluoroethyl-n-butyl sulfone, and pentafluoroethyl-t-butyl sulfone.

Of these, from the viewpoint of exhibiting high ionic conductivity to achieve high input and output, preferred are dimethyl sulfone, ethylmethyl sulfone, diethyl sulfone, n-propylmethyl sulfone, isopropylmethyl sulfone, n-butylmethyl sulfone, t-butylmethyl sulfone, monofluoromethylmethyl sulfone, difluoromethylmethyl sulfone, trifluoromethylmethyl sulfone, monofluoroethylmethyl sulfone, difluoroethylmethyl sulfone, trifluoroethylmethyl sulfone, pentafluoroethylmethyl sulfone, ethylmonofluoromethyl sulfone, ethyldifluoromethyl sulfone, ethyltrifluoromethyl sulfone, ethyltrifluoroethyl sulfone, ethylpentafluoroethyl sulfone, trifluoromethyl-n-propyl sulfone, trifluoromethylisopropyl sulfone, trifluoroethyl-n-butyl sulfone, trifluoroethyl-t-butyl sulfone, trifluoromethyl-n-butyl sulfone, and trifluoromethyl-t-butyl sulfone.

The amount of the sulfone compound incorporated is preferably 0.3% by volume or more, more preferably 1% by volume or more, further preferably 5% by volume or more, and is preferably 40% by volume or less, more preferably 35% by volume or less, further preferably 30% by volume or less, based on the volume of the non-aqueous solvent (100% by volume). When the amount of the sulfone compound incorporated is in the above range, an effect of improving durability, such as cycle characteristics or storage characteristics, can be easily obtained, and further the viscosity of the non-aqueous electrolytic solution can be in an appropriate range, so that a lowering of the electrical conductivity can be avoided, and thus it is easy to avoid a problem caused when the non-aqueous electrolyte secondary battery is charged and discharged at a high current density, such as a lowering of the charge-discharge capacity maintaining ratio.

These compounds may be used individually or in combination, and two or more types of the compounds are preferably used in combination. For example, when a high-permittivity solvent, such as a cyclic carbonate, a cyclic carbonate having a fluorine atom, or a cyclic carboxylate, and a low-viscosity solvent, such as a linear carbonate or a linear carboxylate, are used in combination in a specific incorporation ratio, the battery performance can be advantageously remarkably improved.

As a preferred combination of the non-aqueous solvents, there can be mentioned a combination of mainly a cyclic carbonate and a linear carbonate. In the combination, especially, the proportion of the total of the cyclic carbonate and the linear carbonate to the all non-aqueous solvents is preferably 700/% by volume or more, more preferably 80% by volume or more, further preferably 90% by volume or more, and the proportion of the cyclic carbonate to the total of the cyclic carbonate and the linear carbonate is preferably 5% by volume or more, more preferably 10% by volume or more, further preferably 15% by volume or more, and is preferably 50% by volume or less, more preferably 35% by volume or less, further preferably 30% by volume or less, especially preferably 25% by volume or less. When these non-aqueous solvents are used in combination, the battery produced using these solvents is likely to be improved in the balance between the cycle characteristics and the high-temperature storage characteristics (particularly, the residual capacity and high-load discharge capacity after high-temperature storage).

As the cyclic carbonate, from the viewpoint of the improvement of the cycle characteristics and high-temperature storage characteristics of the battery, preferred are ethylene carbonate, propylene carbonate, monofluoroethylene carbonate, 4,4-difluoroethylene carbonate, 4,5-difluoroethylene carbonate, and 4,5-difluoro-4,5-dimethylethylene carbonate. Specific examples of preferred combinations of ethylene carbonate and a linear carbonate include a combination of ethylene carbonate and dimethyl carbonate, a combination of ethylene carbonate and diethyl carbonate, a combination of ethylene carbonate and ethylmethyl carbonate, a combination of ethylene carbonate, dimethyl carbonate, and diethyl carbonate, a combination of ethylene carbonate, dimethyl carbonate, and ethylmethyl carbonate, a combination of ethylene carbonate, diethyl carbonate, and ethylmethyl carbonate, and a combination of ethylene carbonate, dimethyl carbonate, diethyl carbonate, and ethylmethyl carbonate.

Preferred combinations include combinations of ethylene carbonate and a linear carbonate and further propylene carbonate. When propylene carbonate is contained, the volume ratio of ethylene carbonate and propylene carbonate is preferably 99:1 to 40:60, especially preferably 95:5 to 50:50. Further, the proportion of the propylene carbonate to the all non-aqueous solvents is preferably 0.1% by volume or more, more preferably 1% by volume or more, further preferably 2% by volume or more, and is preferably 20% by volume or less, more preferably 8% by volume or less, further preferably 5% by volume or less. When propylene carbonate is contained in the above concentration range, an advantage is obtained in that while maintaining the characteristics of the combination of ethylene carbonate and a dialkyl carbonate, further excellent low-temperature characteristics are achieved.

Among the combinations of ethylene carbonate and a linear carbonate, those containing an asymmetric linear alkyl carbonate as a linear carbonate are further preferred. Especially preferred are the combinations containing ethylene carbonate, a symmetric linear carbonate, and an asymmetric linear carbonate, such as a combination of ethylene carbonate, dimethyl carbonate, and ethylmethyl carbonate, a combination of ethylene carbonate, diethyl carbonate, and ethylmethyl carbonate, and a combination of ethylene carbonate, dimethyl carbonate, diethyl carbonate, and ethylmethyl carbonate because excellent balance between the cycle characteristics and the large-current discharge characteristics can be obtained. Of these, preferred are those in which the asymmetric linear carbonate is ethylmethyl carbonate, or the alkyl group of the linear carbonate has 1 to 2 carbon atoms.

Specific examples of preferred combinations of monofluoroethylene carbonate and a linear carbonate include a combination of monofluoroethylene carbonate and dimethyl carbonate, a combination of monofluoroethylene carbonate and diethyl carbonate, a combination of monofluoroethylene carbonate and ethylmethyl carbonate, a combination of monofluoroethylene carbonate, dimethyl carbonate, and diethyl carbonate, a combination of monofluoroethylene carbonate, dimethyl carbonate, and ethylmethyl carbonate, a combination of monofluoroethylene carbonate, diethyl carbonate, and ethylmethyl carbonate, and a combination of monofluoroethylene carbonate, dimethyl carbonate, diethyl carbonate, and ethylmethyl carbonate.

Preferred combinations include combinations of monofluoroethylene carbonate and a linear carbonate, which further contain ethylene carbonate and/or propylene carbonate. When the combination of monofluoroethylene carbonate and a linear carbonate contains ethylene carbonate and/or propylene carbonate, the volume ratio of monofluoroethylene carbonate and ethylene carbonate and/or propylene carbonate is preferably 1:3 to 3:1, especially preferably 1:2 to 2:1. When ethylene carbonate and/or propylene carbonate is contained in the above concentration range, a stable protective film can be formed on the negative electrode and further the electrical conductivity of the electrolytic solution can be secured.

When diethyl carbonate is contained in the non-aqueous solvents, the proportion of the diethyl carbonate to the all non-aqueous solvents is preferably 10% by volume or more, more preferably 20% by volume or more, further preferably 25% by volume or more, especially preferably 30% by volume or more, and is preferably 90% by volume or less, more preferably 80% by volume or less, further preferably 75% by volume or less, especially preferably 70% by volume or less, and, when diethyl carbonate is contained in the above range, gas generation during high-temperature storage is likely to be suppressed.

When dimethyl carbonate is contained in the non-aqueous solvents, the proportion of the dimethyl carbonate to the all non-aqueous solvents is preferably 10% by volume or more, more preferably 20% by volume or more, further preferably 25% by volume or more, especially preferably 30% by volume or more, and is preferably 90% by volume or less, more preferably 80% by volume or less, further preferably 75% by volume or less, especially preferably 70% by volume or less, and, when dimethyl carbonate is contained in the above range, the load characteristics of the battery are likely to be improved.

Especially, when dimethyl carbonate and ethylmethyl carbonate are contained in such a proportion that the amount of dimethyl carbonate is larger than the amount of ethylmethyl carbonate, it is advantageously likely that the battery characteristics after high-temperature storage can be improved while securing the electrical conductivity of the electrolytic solution.

From the viewpoint of the improvement of the electrical conductivity of the electrolytic solution and the improvement of the battery characteristics after storage, the volume ratio of dimethyl carbonate to ethylmethyl carbonate (dimethyl carbonate/ethylmethyl carbonate) in the all non-aqueous solvents is preferably 1.1 or more, more preferably 1.5 or more, further preferably 2.5 or more. From the viewpoint of the improvement of the battery characteristics at low temperatures, the volume ratio (dimethyl carbonate/ethylmethyl carbonate) is preferably 40 or less, more preferably 20 or less, further preferably 10 or less, especially preferably 8 or less.

In the above-mentioned combinations of mainly a cyclic carbonate and a linear carbonate, a solvent other than the above cyclic carbonates and linear carbonates, such as a cyclic carbonate, a linear carbonate, a cyclic carboxylate, a linear carboxylate, a cyclic ether, a linear ether, a sulfur-containing organic solvent, a phosphorus-containing organic solvent, or an aromatic fluorine-containing solvent, may be mixed.

Other preferred examples of non-aqueous solvents include ones containing 60% by volume or more of an organic solvent selected from the group consisting of ethylene carbonate, propylene carbonate, and butylene carbonate or a mixed solvent of two or more organic solvents selected from the above group. The non-aqueous electrolytic solution using the above mixed solvent is likely to rarely cause evaporation of the solvent or solution leak even when used at high temperatures. Especially, the proportion of the total of the ethylene carbonate and the propylene carbonate to the all non-aqueous solvents is preferably 70% by volume or more, more preferably 80% by volume or more, further preferably 90% by volume or more, and further the volume ratio of ethylene carbonate and propylene carbonate is preferably 30:70 to 60:40, and, when the non-aqueous electrolytic solution using such a mixed solvent is used, the balance between, for example, the cycle characteristics and the high-temperature storage characteristics is likely to be improved.

In the present specification, the volume of the non-aqueous solvent is a value measured at 25° C., and, with respect to a solvent which is in a solid state at 25° C., such as ethylene carbonate, a volume measured at the melting point of the solvent is used.

1-3. Compound Represented by the Formula (1)

The non-aqueous electrolytic solution of the present invention has a characteristic feature in that it contains a compound represented by the formula (1). The compound represented by the formula (1) is a compound having a carboxylate structure, sulfonic ester structure, and/or phosphoric ester structure. It is considered that, by virtue of having a plurality of the structures, when being electrochemically reduced on the surface of the negative electrode, the compound represented by the formula (1) improves the negative electrode film in thermal stability, so that an effect of promoting the formation of a preferred metal salt of multianion (for example, a lithium salt) is exhibited. Further, these structures can be efficiently formed in high yield, and therefore are considered to have a role in facilitating a synthesis of the compound represented by the formula (1) to suppress the production cost.

Further, one of the characteristic features of the present invention resides in that Z in the formula (1) above has 4 to 12 carbon atoms. It is considered that when Z has 4 to 12 carbon atoms, the molecular size is large such that the solubility of the above-mentioned metal salt of multianion (for example, lithium salt) in the electrolytic solution is suppressed. This effect is more remarkable when Z is nonpolar, for example, Z is a linear alkylene group.

It is considered that when the solubility of the metal salt of multianion (for example, a lithium salt) in the electrolytic solution is suppressed, the negative electrode film is further stabilized to suppress a side reaction, so that the cycle capacity maintaining ratio and low-temperature resistance characteristics are improved.

<Compound Represented by Formula (1)>

The compound in the present invention is represented by the following formula (1).

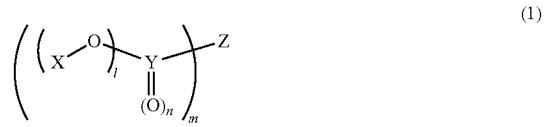

Wherein:

X represents an organic group containing a heteroatom, the organic group having at least one oxygen atom as the heteroatom, Y represents a sulfur atom, a phosphorus atom, or a carbon atom, n represents an integer of 1 or 2, m represents an integer of 2 to 4, and l represents an integer of 1 or 2, and Z represents an organic group having 4 to 12 carbon atoms and optionally having a heteroatom.

The heteroatom indicates an atom other than a carbon atom and a hydrogen atom. The organic group containing a heteroatom is, for example, of a structure comprising an atom selected from the group consisting of a nitrogen atom, a phosphorus atom, a boron atom, a sulfur atom, a silicon atom, an oxygen atom, and a halogen atom, and has at least one oxygen atom. With respect to X, the organic group containing a heteroatom may be of a structure comprising no carbon atom, but preferably comprises a carbon atom. With respect to X, the organic group containing a heteroatom preferably has 1 or more carbon atoms, more preferably 2 or more carbon atoms, and preferably 15 or less, more preferably 10 or less carbon atoms. With respect to X, the organic group containing a heteroatom may be of a structure comprising no carbon atom, but has at least one oxygen atom.

X is an organic group containing a heteroatom, and has at least one oxygen atom as the heteroatom. By virtue of having a structure containing a heteroatom (at least one of which is an oxygen atom) at the end of the compound, the compound can be increased in the reactivity on the surface of the negative electrode to improve the negative electrode film in thermal stability. As a result, a more advantageous metal salt of multianion (for example, a lithium salt) can be formed. As specific examples of X's, there can be mentioned the followings.

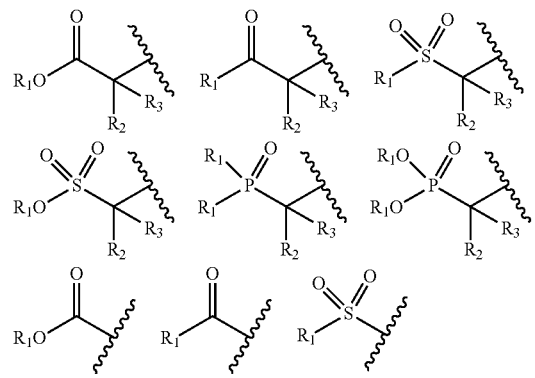

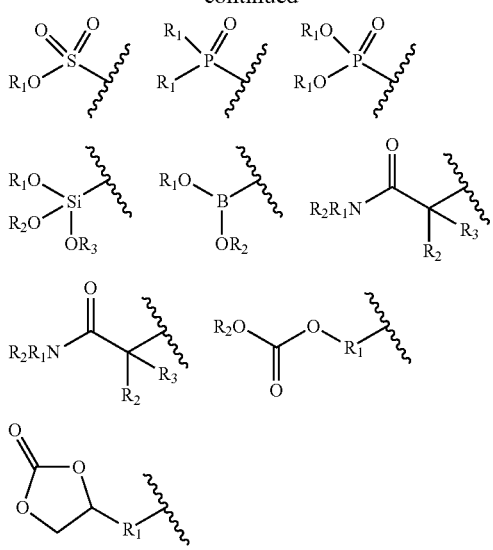

Wherein each of $R_1$ to $R_4$ independently represents a hydrogen atom or a hydrocarbon group having 1 to 12 carbon atoms.

Examples of the hydrocarbon groups having 1 to 12 carbon atoms include an alkyl group, a cycloalkyl group, an aryl group, an alkenyl group, and an alkynyl group. Of these, an alkyl group is preferred. As the alkyl group, a methyl group and an ethyl group are preferred, and a methyl group is more preferred.

Among the above-shown specific examples of X's, the below-shown structures containing a sulfonyl group or a carbonyl group are more preferred. These structures are likely to suffer bond cleavage on the surface of the negative electrode, and the compound having a plurality of the structures can remarkably improve the negative electrode film in thermal stability.

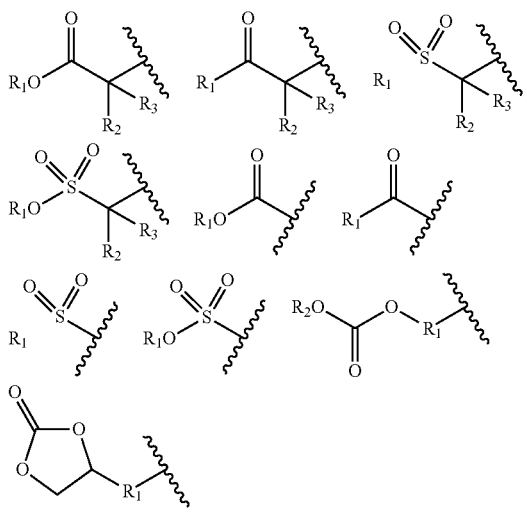

Wherein $R_1$ to $R_3$ are as defined above.
Among the above structures, the structures shown below are more preferred.

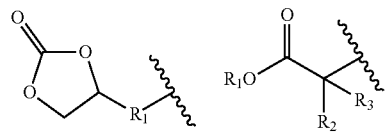

Wherein $R_1$ to $R_3$ are as defined above.

Of these, the below-shown structures containing a carbonyl group are further preferred.

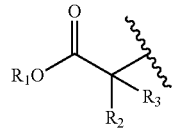

Wherein $R_1$ to $R_3$ are as defined above.
Especially preferred are the structures shown below.

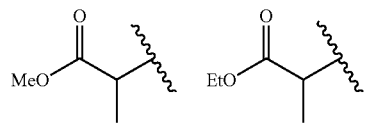

Y is a sulfur atom, a phosphorus atom, or a carbon atom, and, from the viewpoint of the improvement of the battery characteristics, Y is preferably a sulfur atom or a carbon atom, most preferably a sulfur atom.

n and l are an integer of 1 or 2, and, when Y is a sulfur atom, n and l represent 1 and 2, or 1 and 1, respectively, and it is preferred that n and l represent 2 and 1, respectively. When Y is a carbon atom, each of n and l represents 1.

m represents an integer of 2 to 4, and, from the viewpoint of the thermal stability of the negative electrode film, m especially preferably represents 2.

Z is an organic group having 4 to 12 carbon atoms and optionally having a heteroatom. The organic group optionally having a heteroatom is, for example, of a structure comprising an atom selected from the group consisting of a carbon atom, a hydrogen atom, a nitrogen atom, a phosphorus atom, a boron atom, a sulfur atom, a silicon atom, an oxygen atom, and a halogen atom, and may have either a heteroatom or no heteroatom in the structure. Z preferably has 4 to 10 carbon atoms, more preferably 4 to 6 carbon atoms. In the structure, the carbon atoms may be either linear or branched, and are preferably linear.

The organic group for Z is preferably an alkylene group, an ether group, or an ester group, more preferably an alkylene group or an ether group, further preferably an alkylene group, especially preferably a linear alkylene group having 4 to 6 carbon atoms. Z is a linking group that links Y's together, and a plurality of Y's may be bonded to any of the atoms in Z, and may be bonded to either the same atom or different atoms in Z, and are preferably bonded to different atoms in Z.

As specific preferred examples of the compounds represented by the formula (1), there can be mentioned the followings.

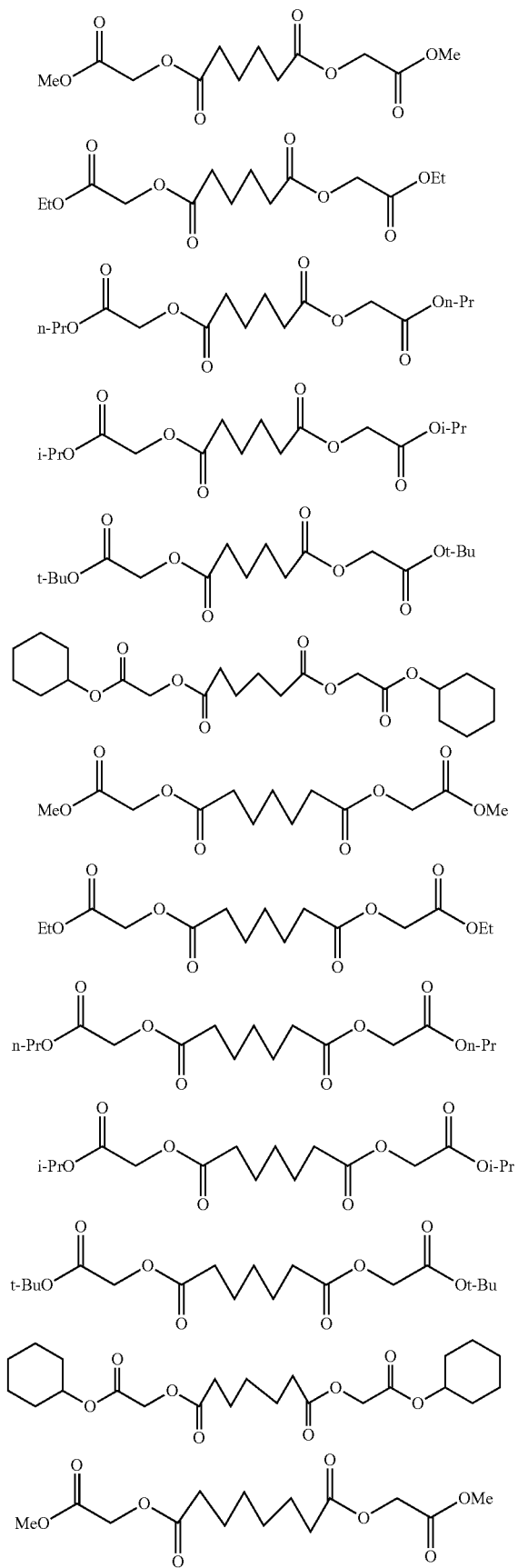
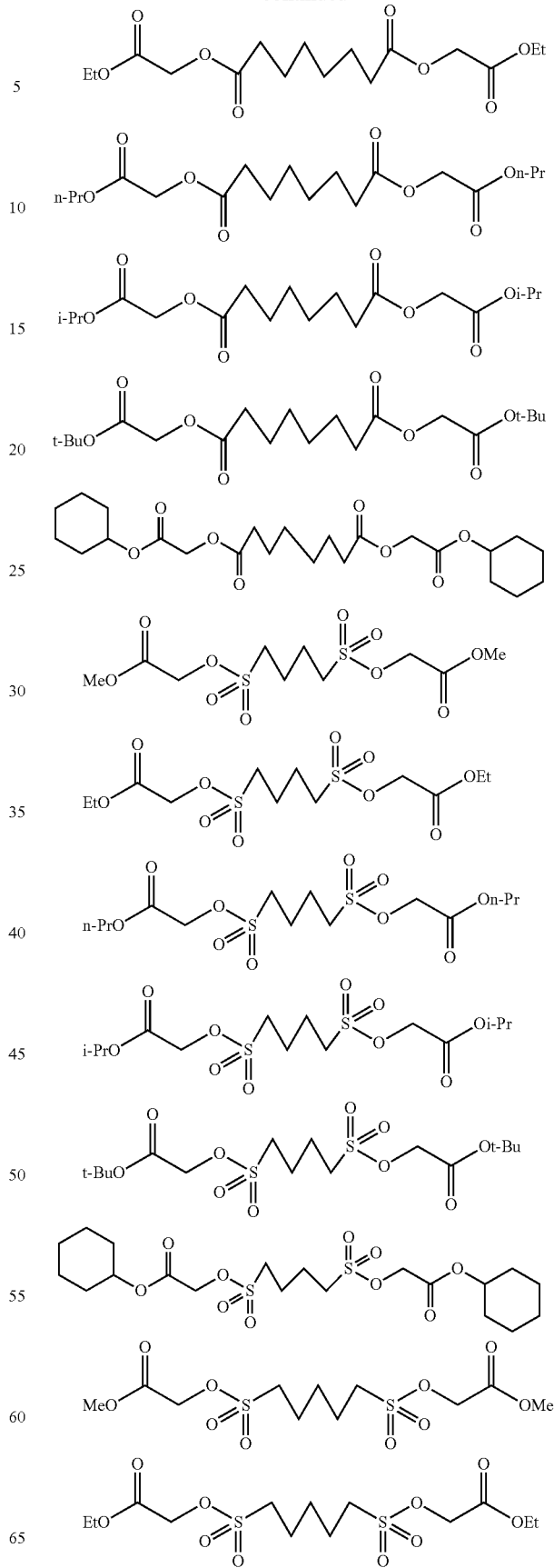
-continued

-continued
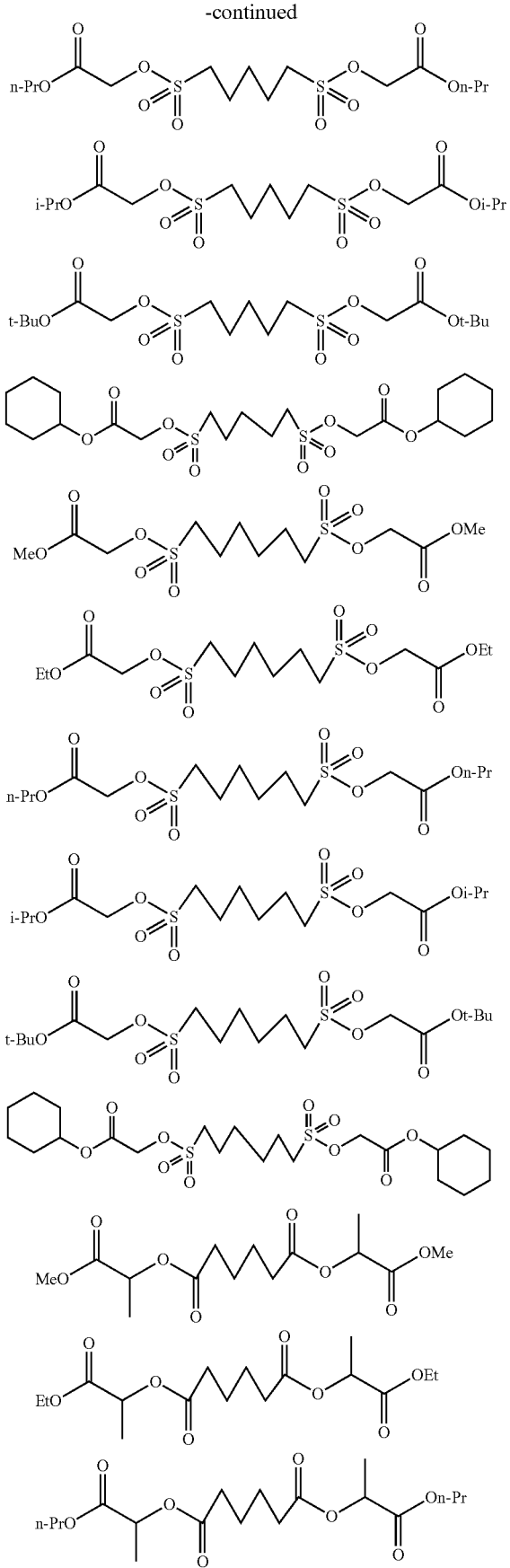
-continued
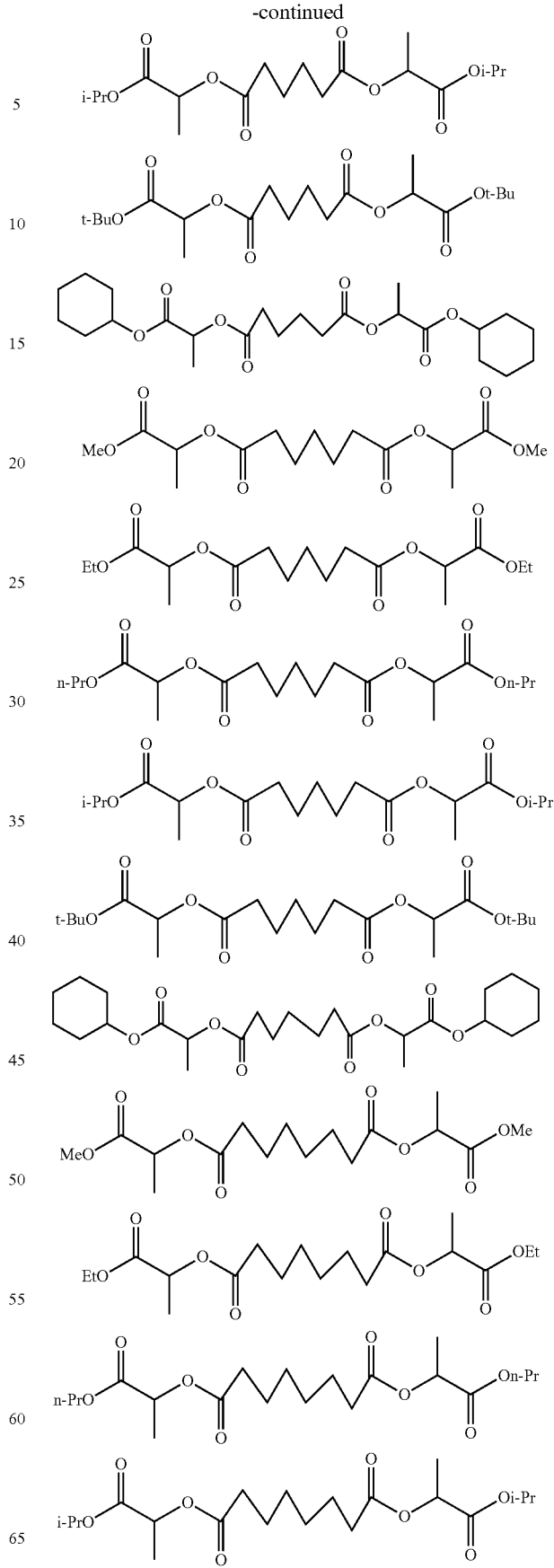

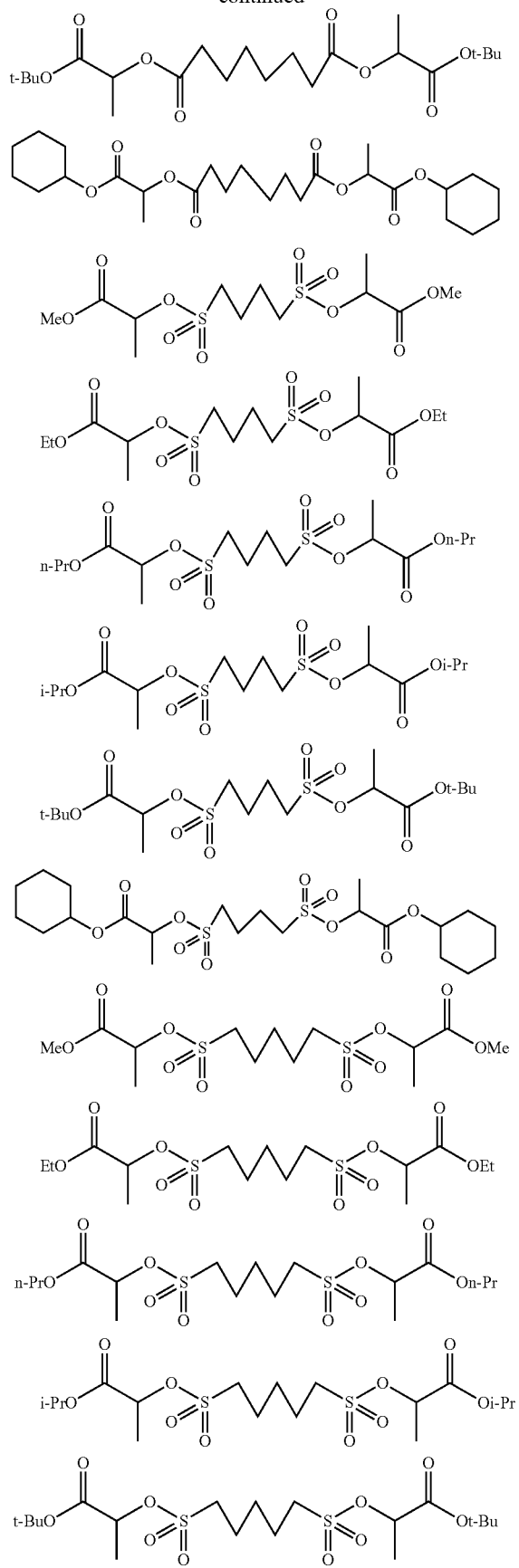
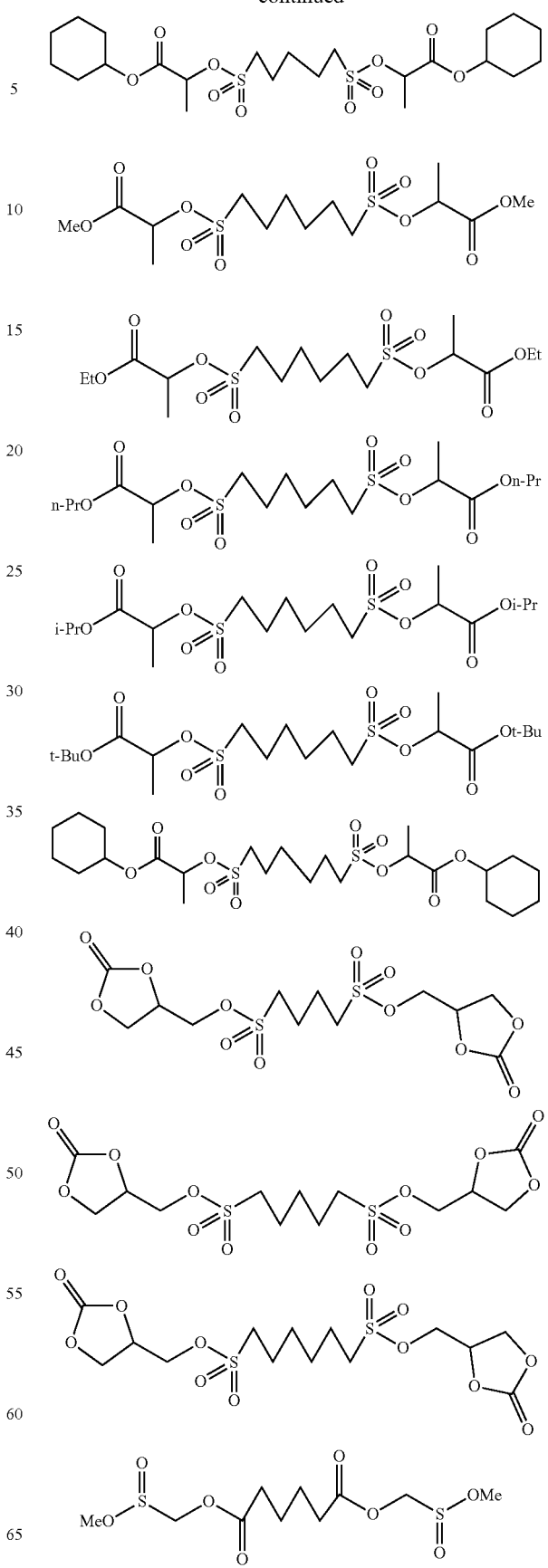

-continued
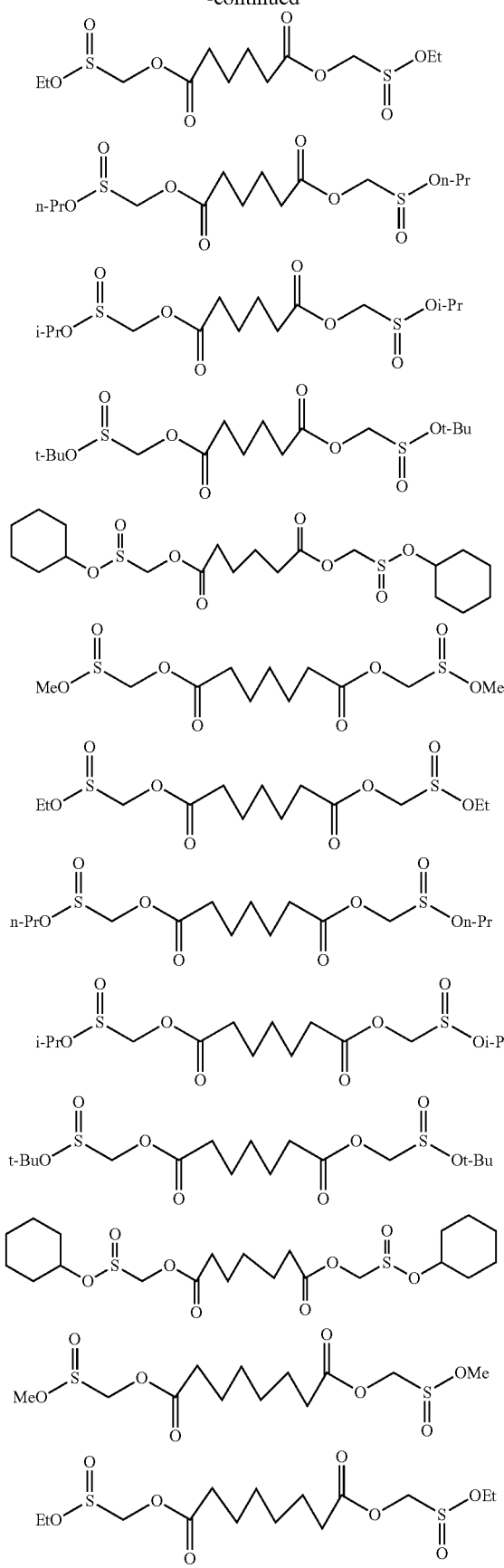
-continued
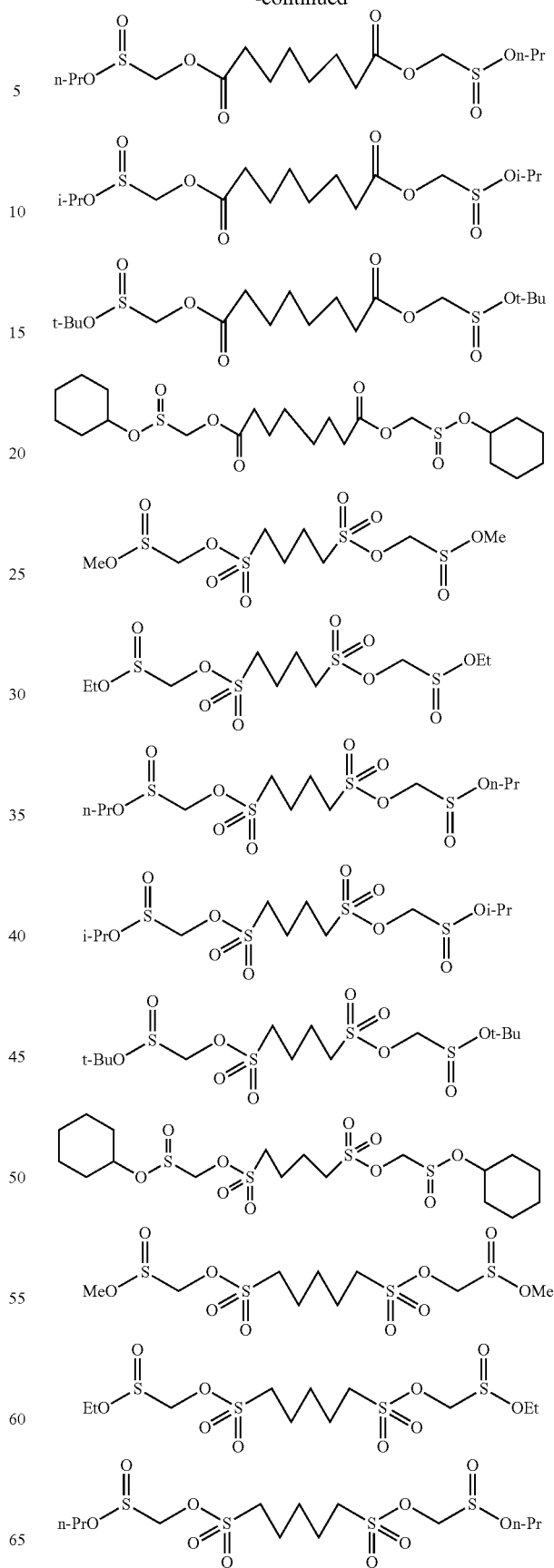

-continued
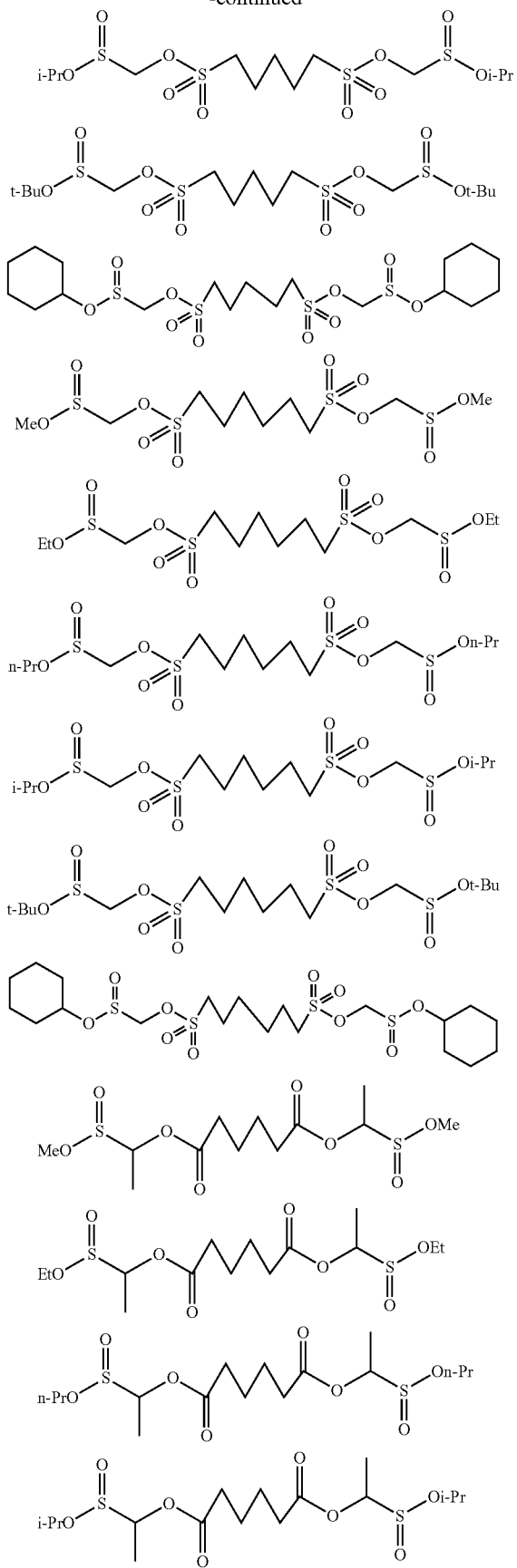
-continued
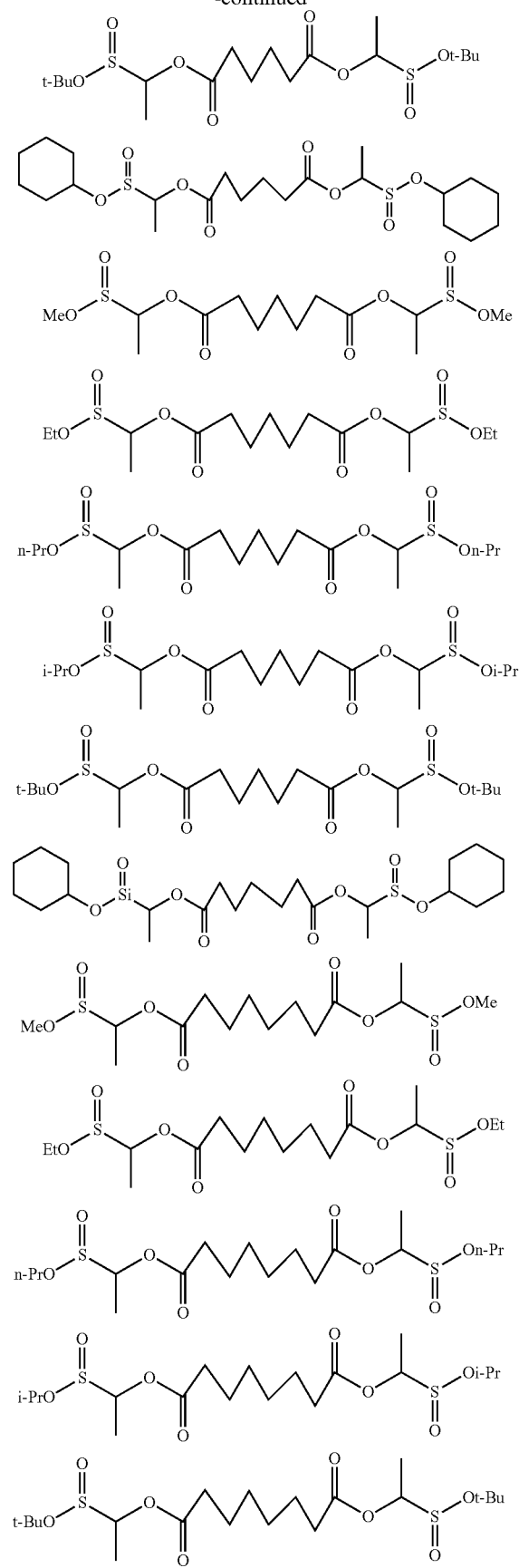

29
-continued
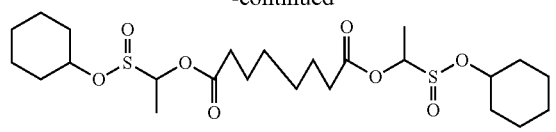
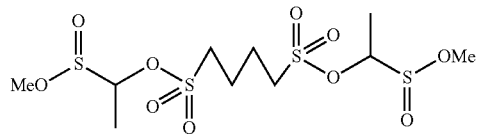
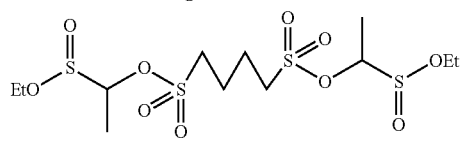
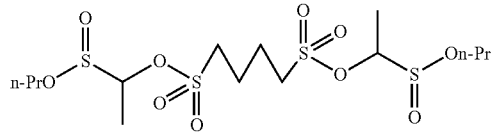
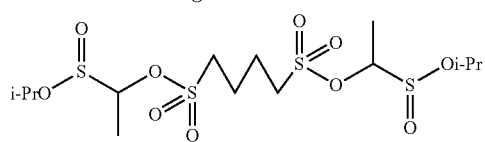
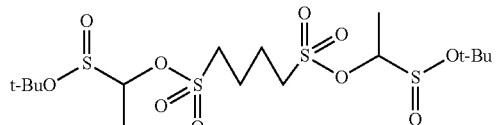
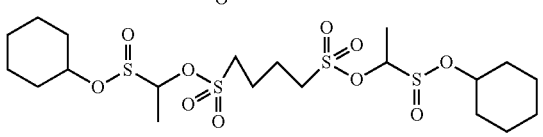
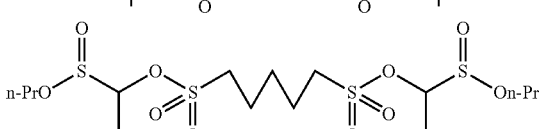
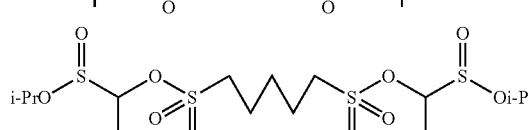
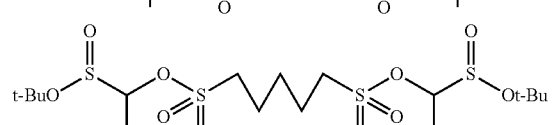
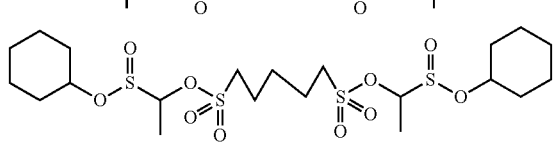
30
-continued
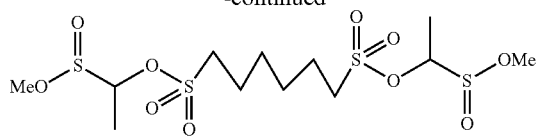
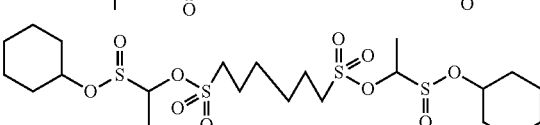
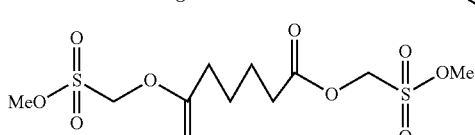
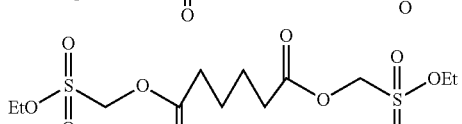
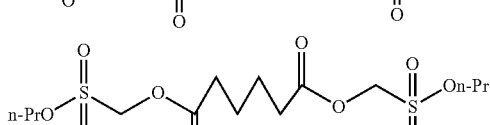
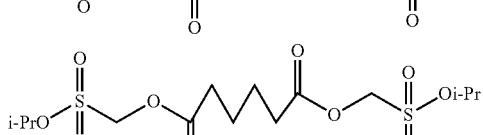
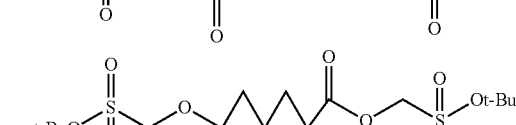
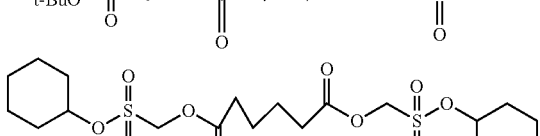
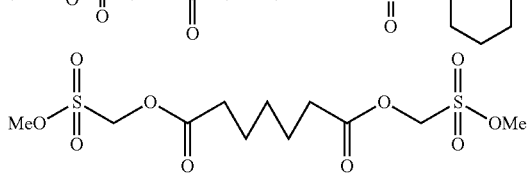

-continued
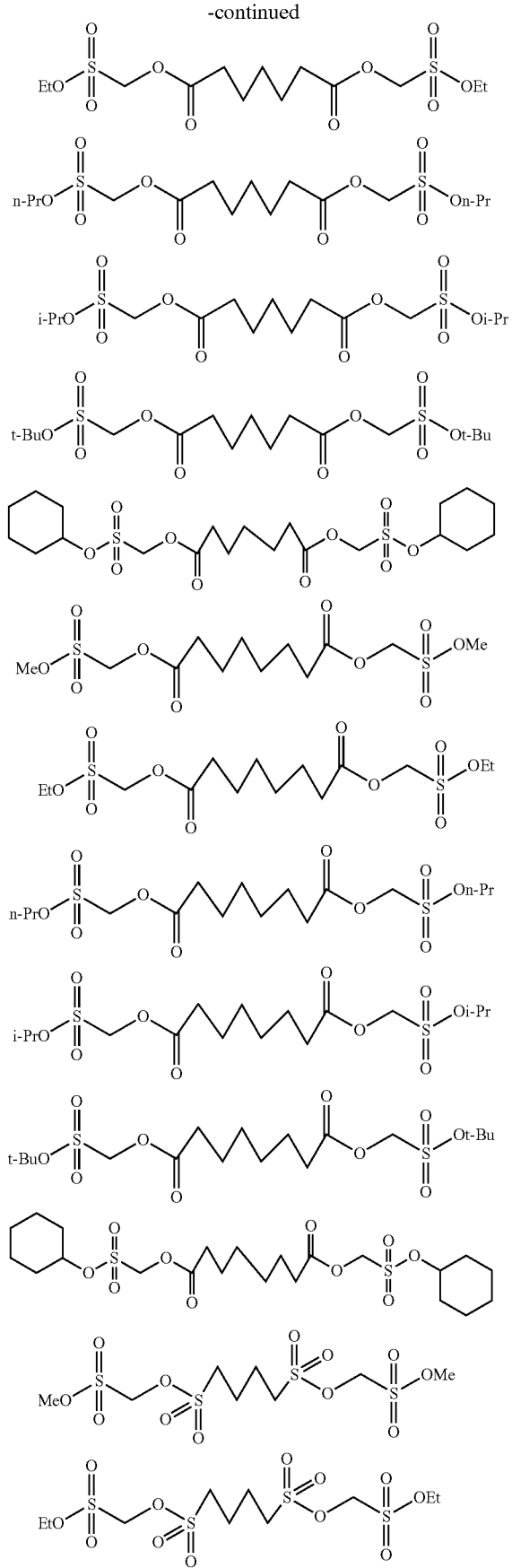
-continued
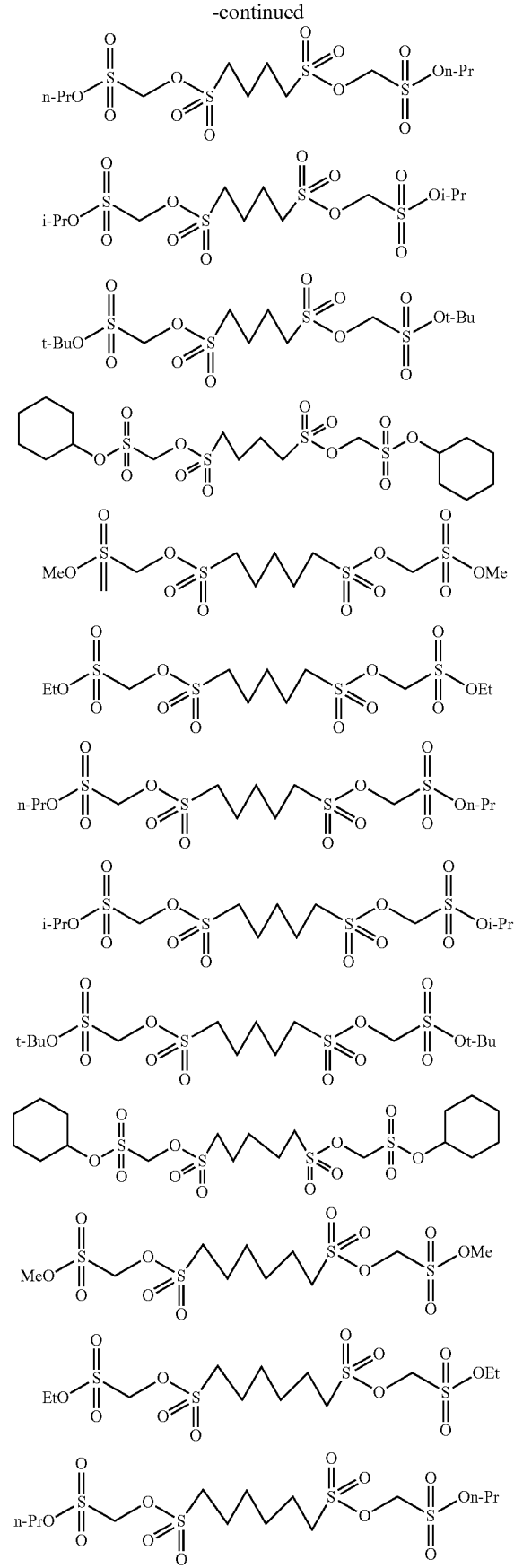

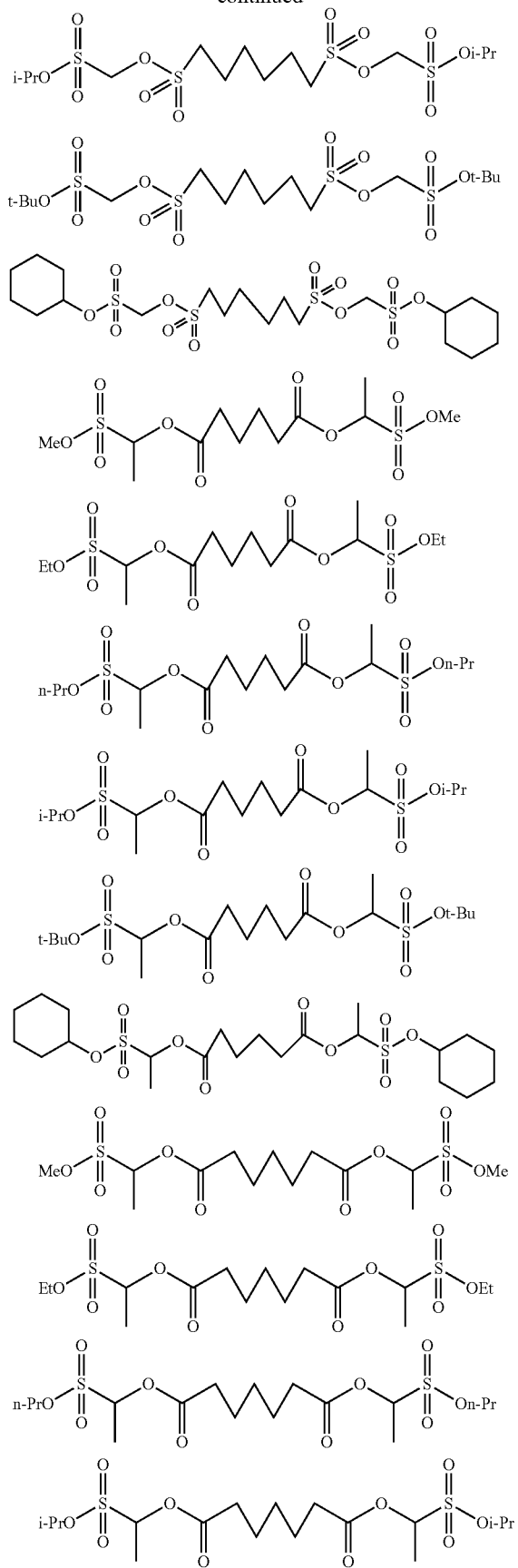
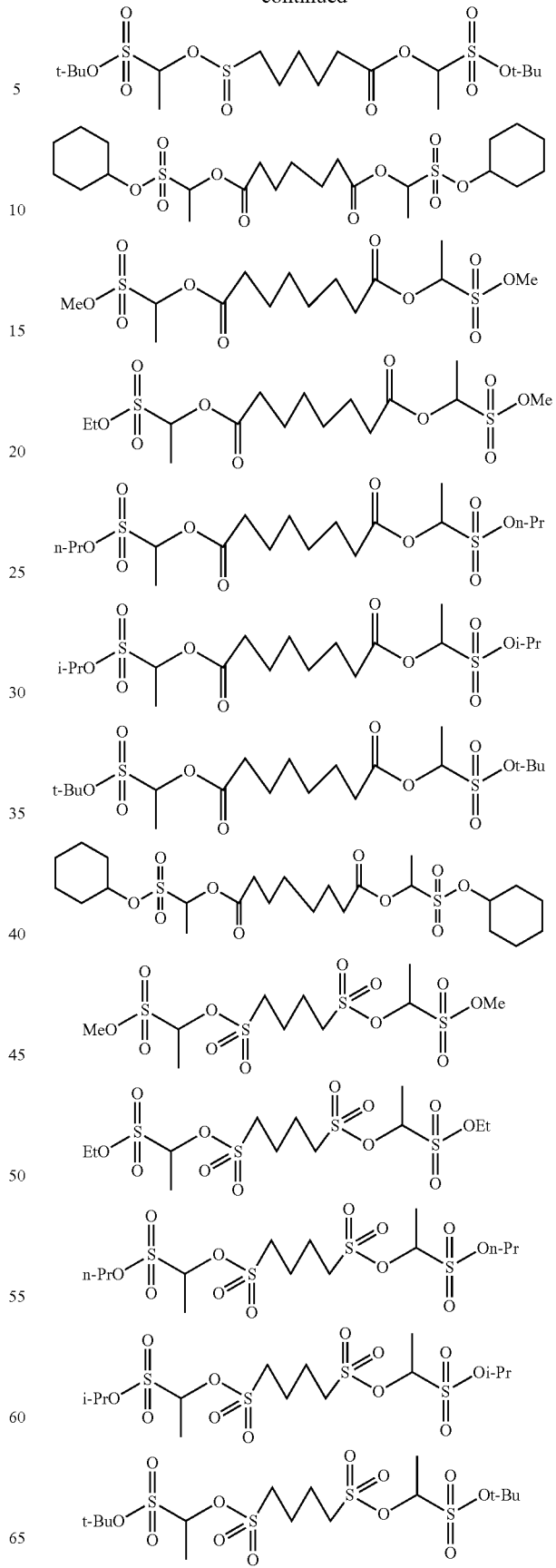

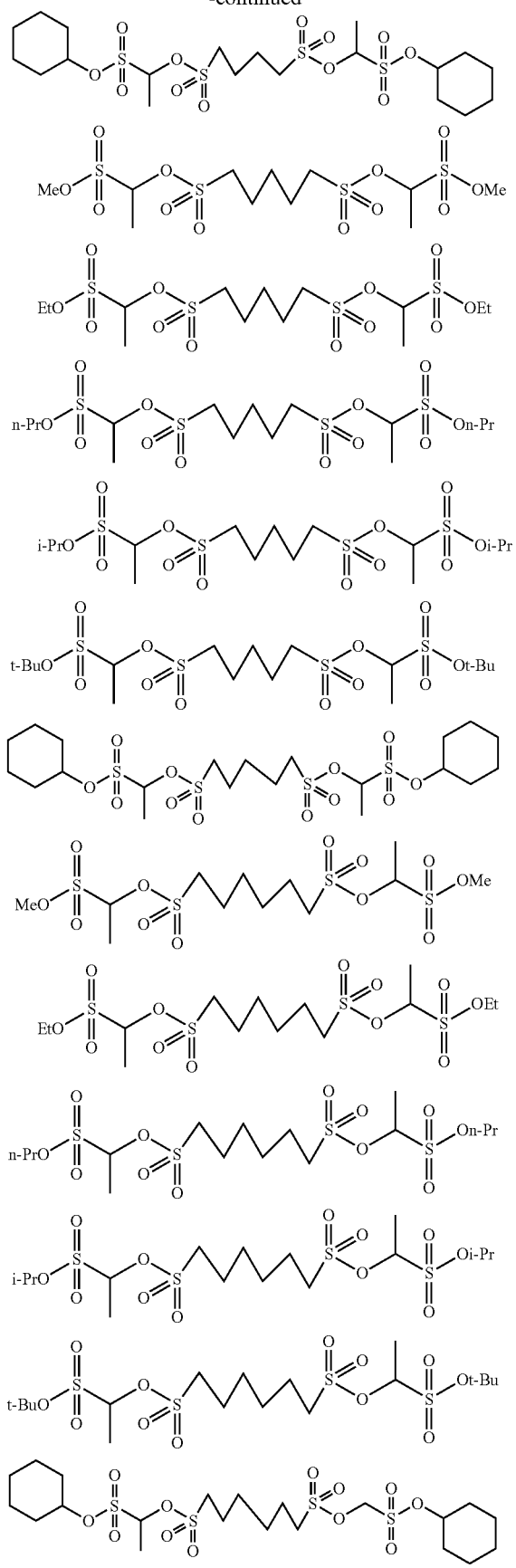
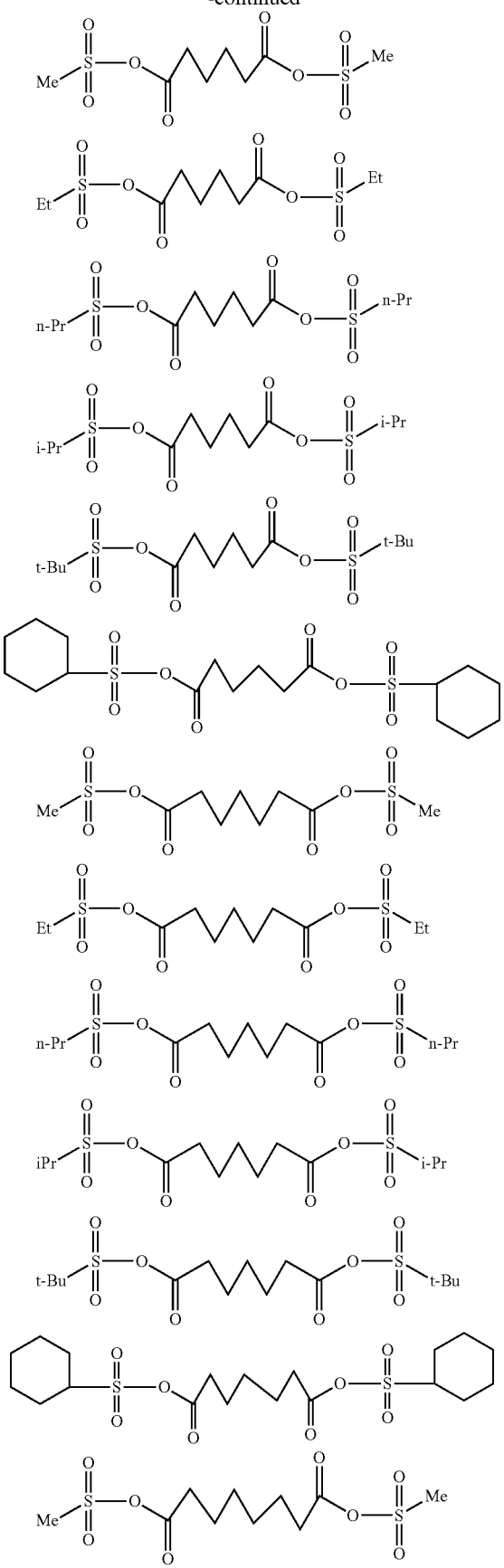

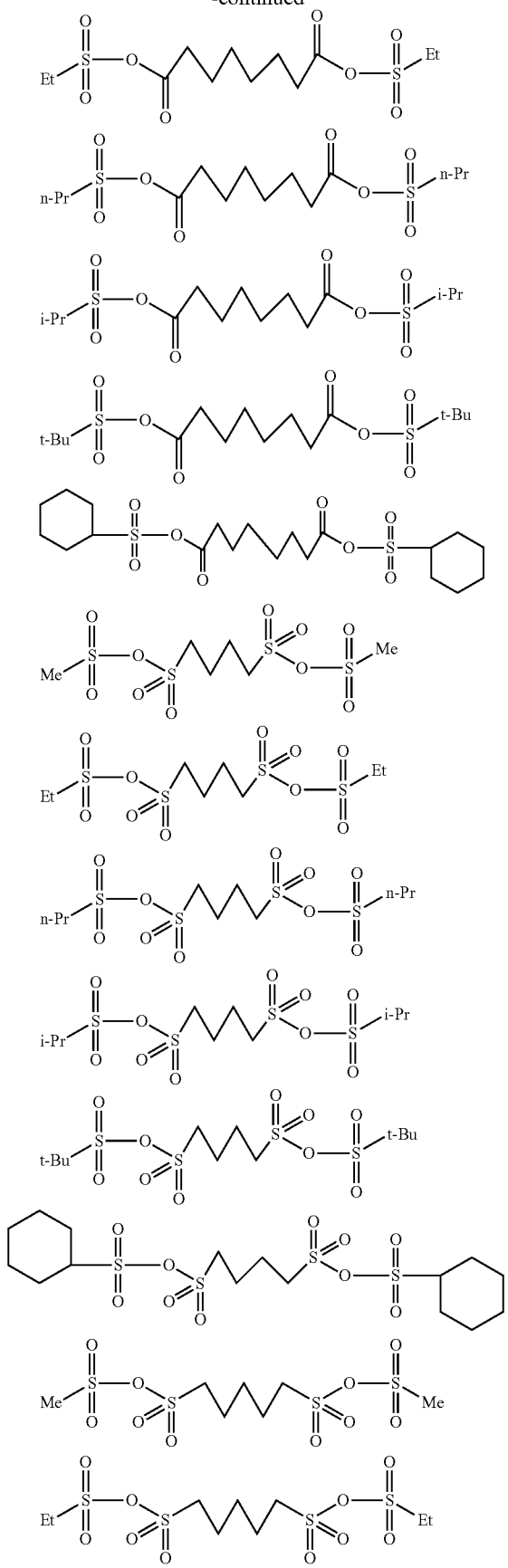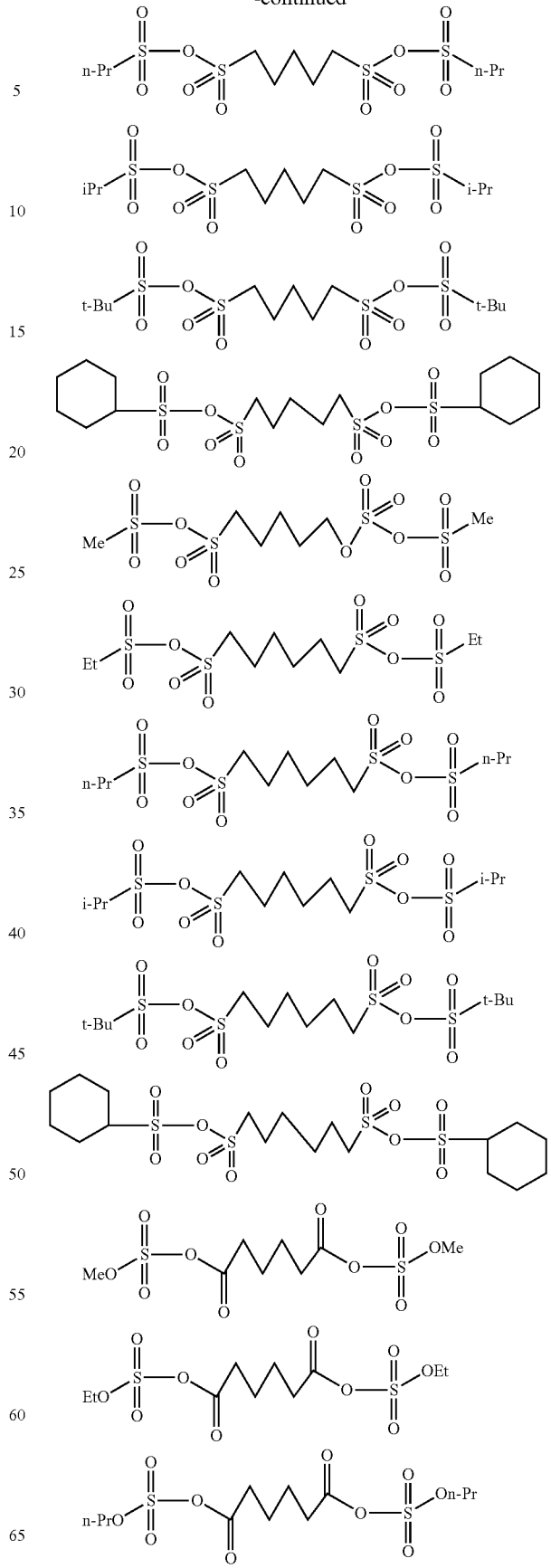

-continued
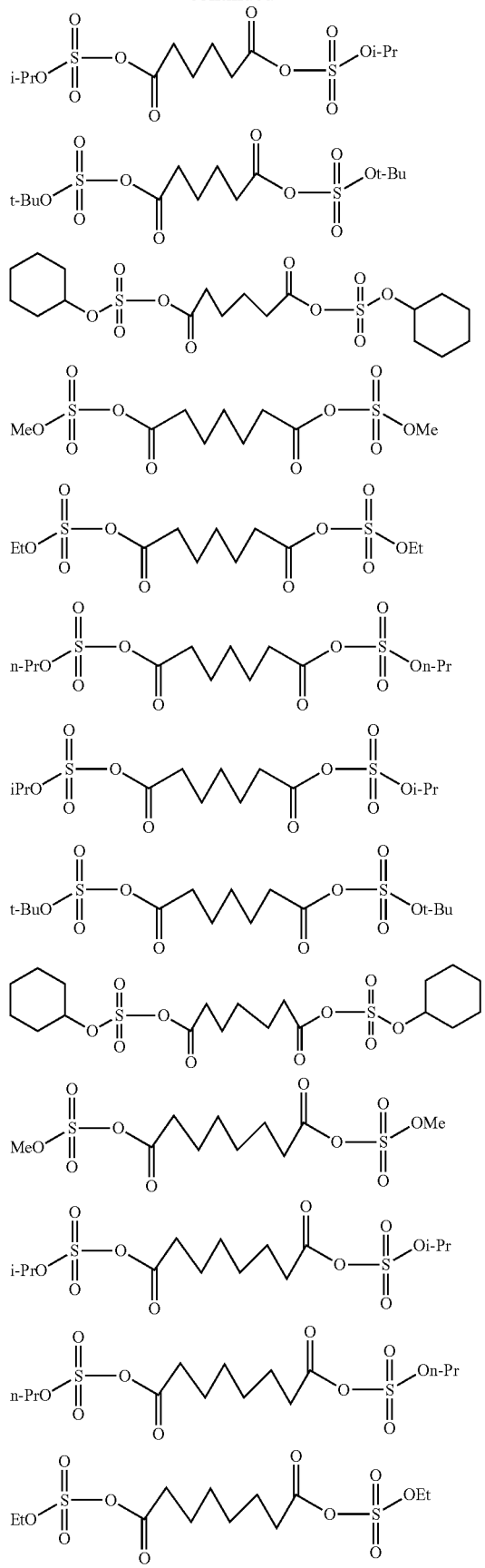
-continued
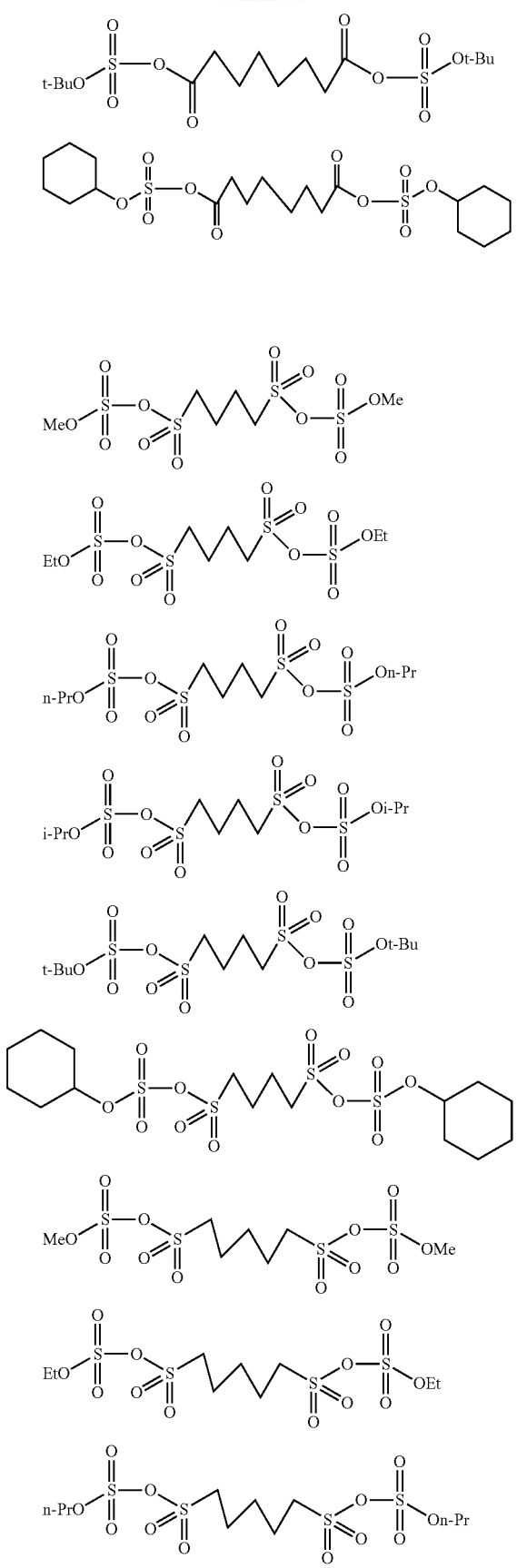

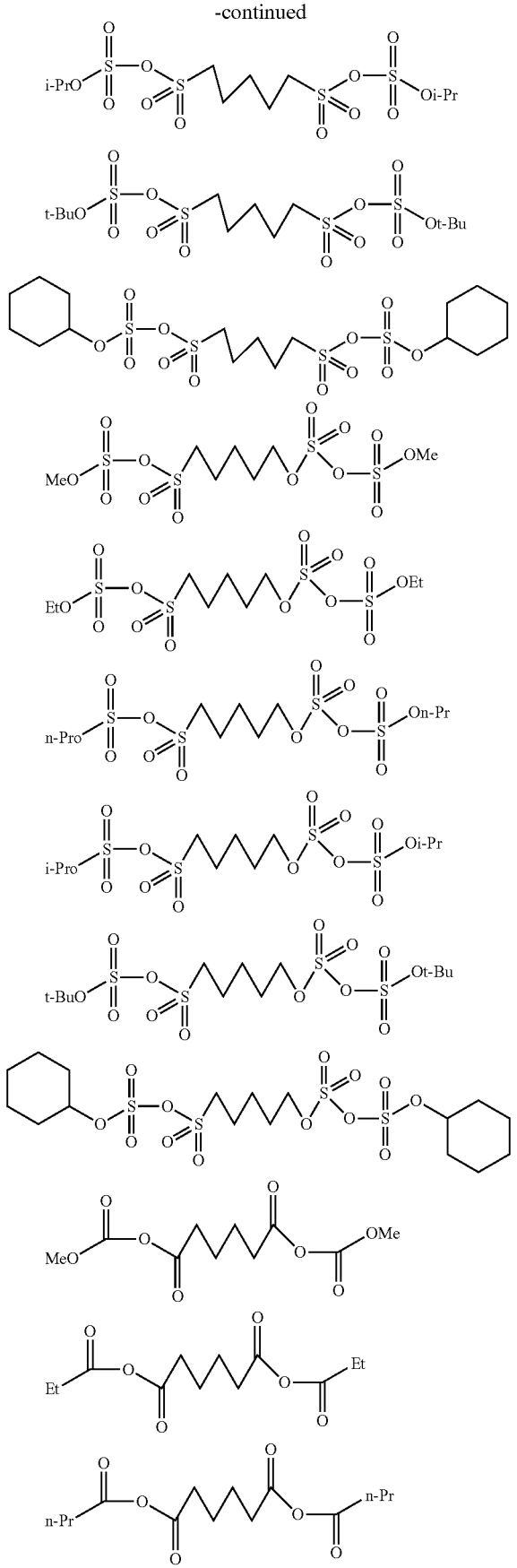
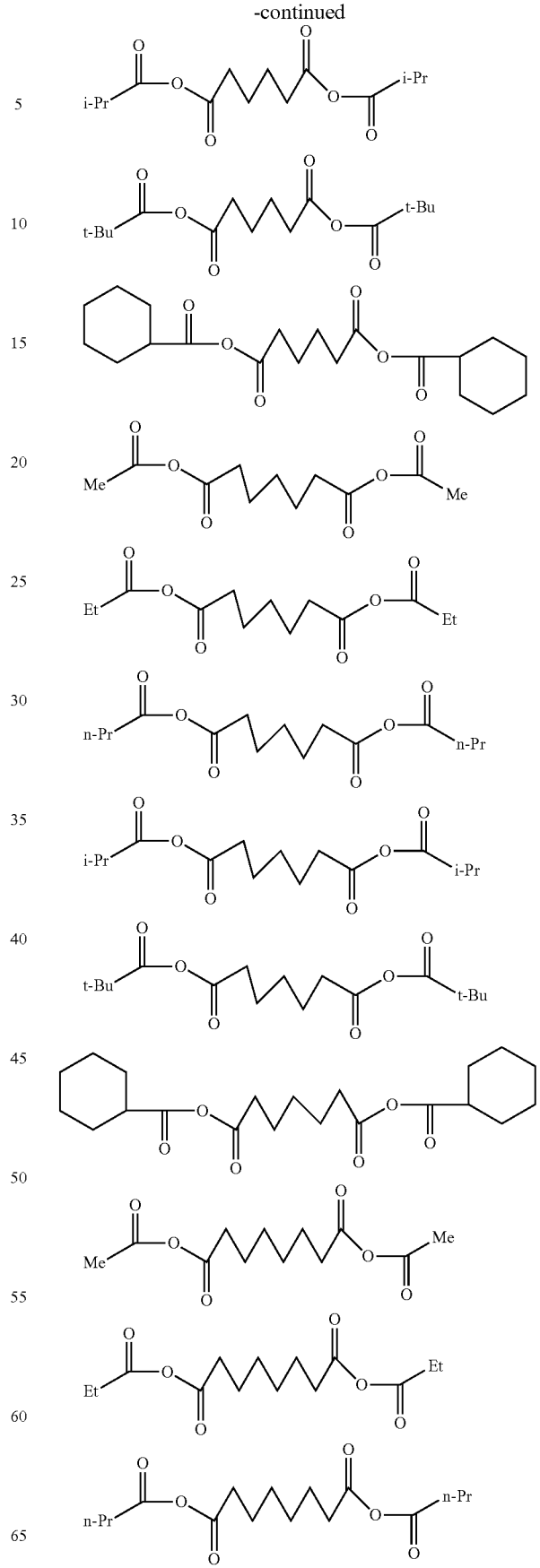

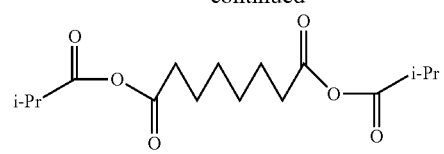
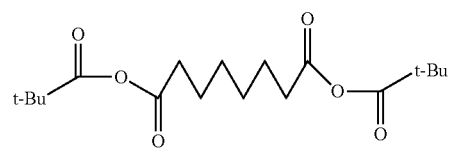
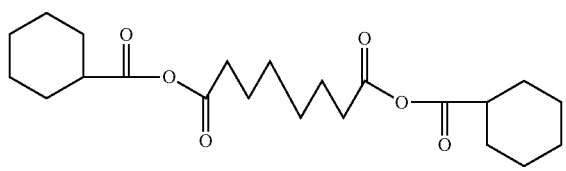
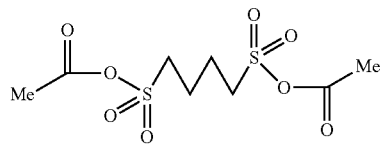
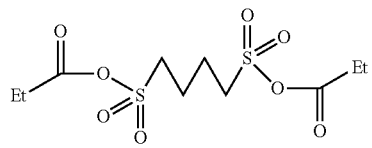
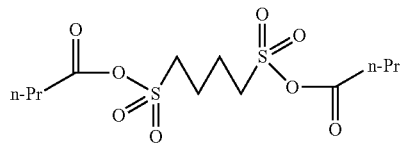
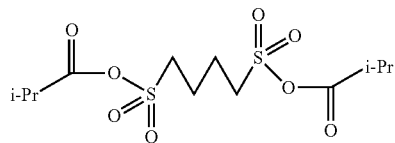
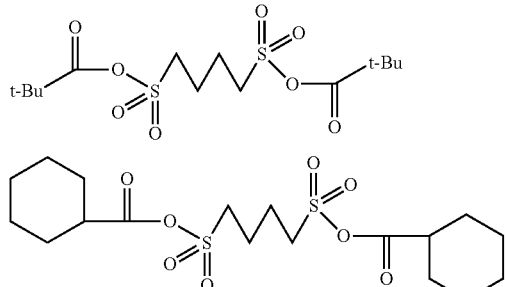
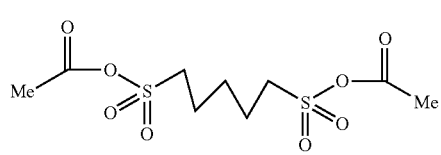
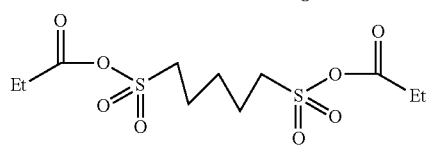
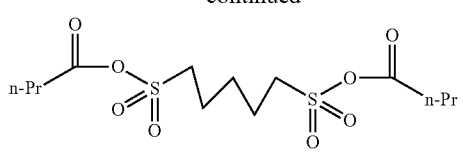
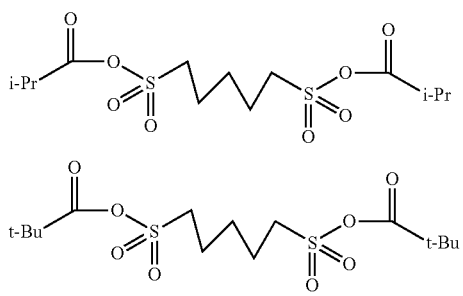
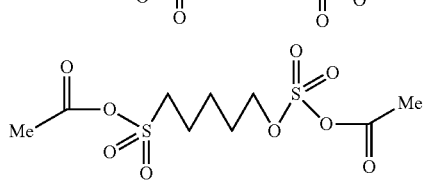
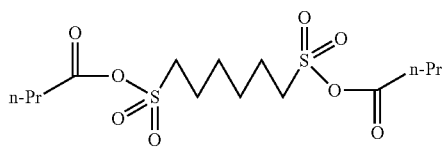
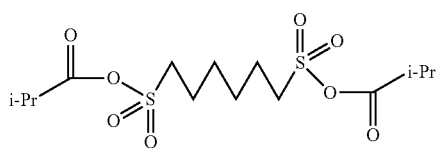
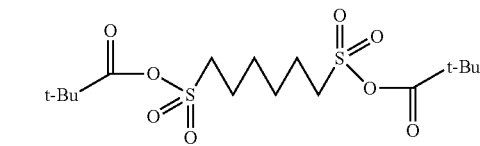
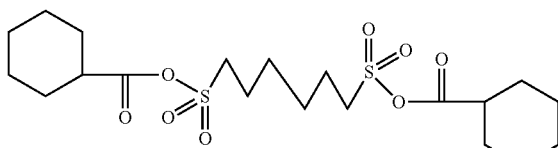
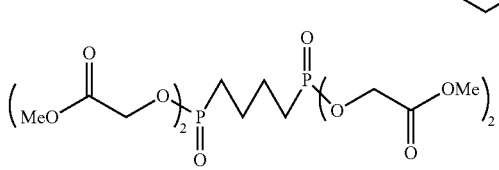

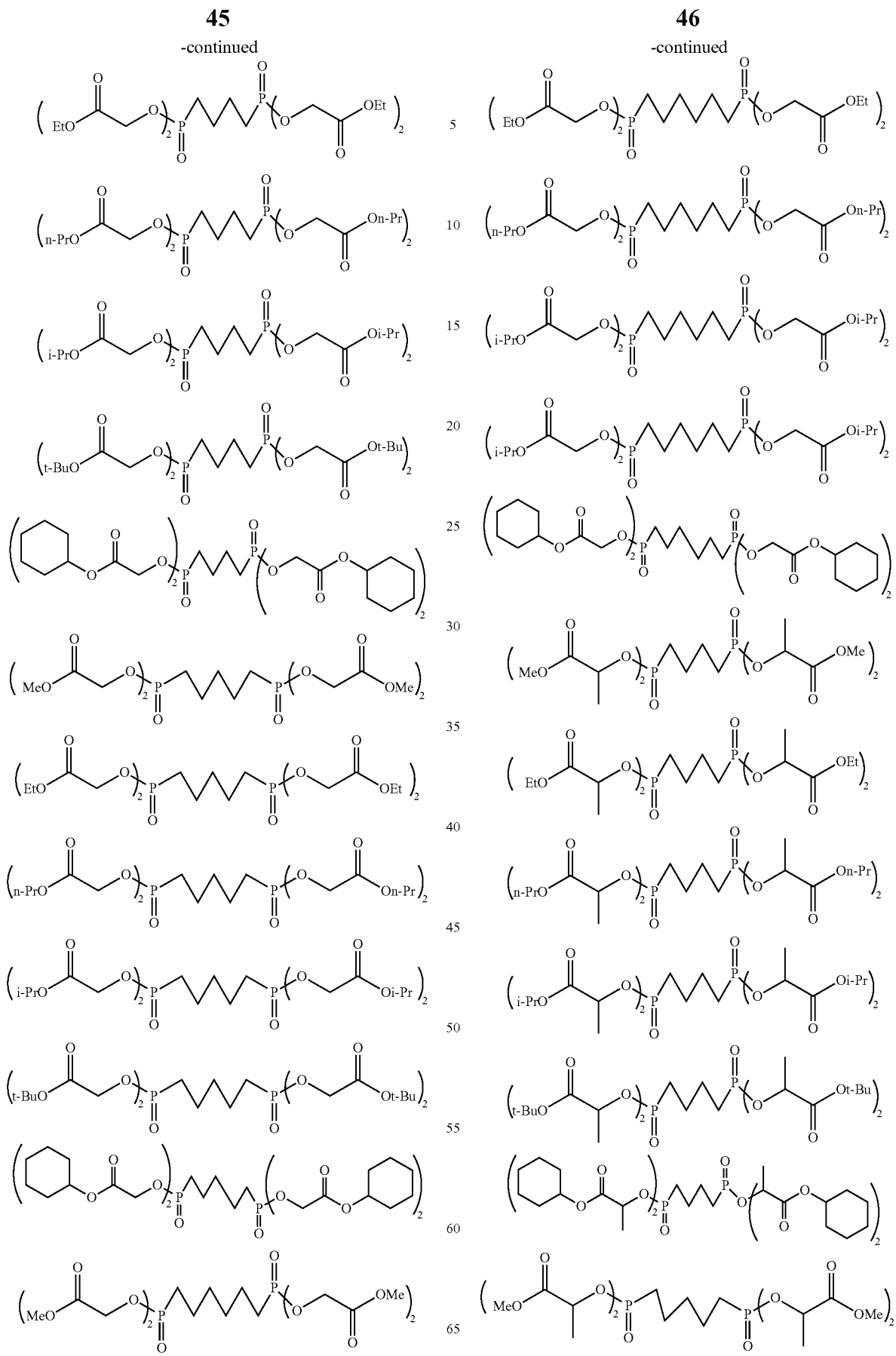

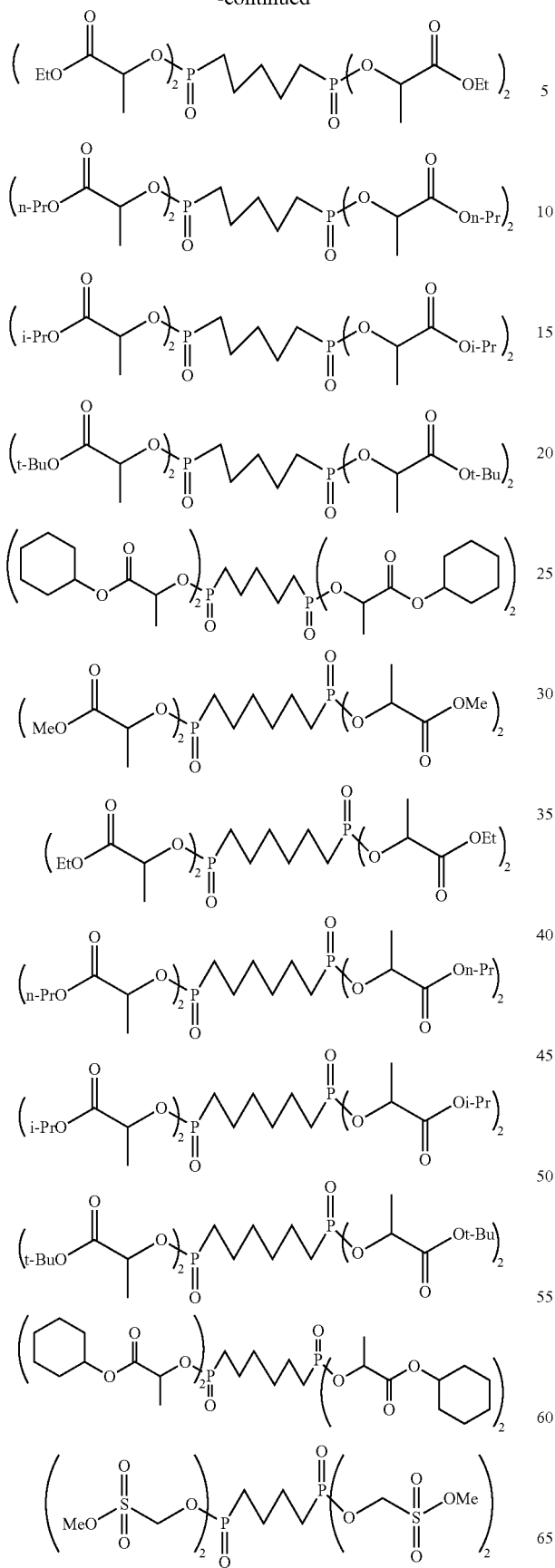
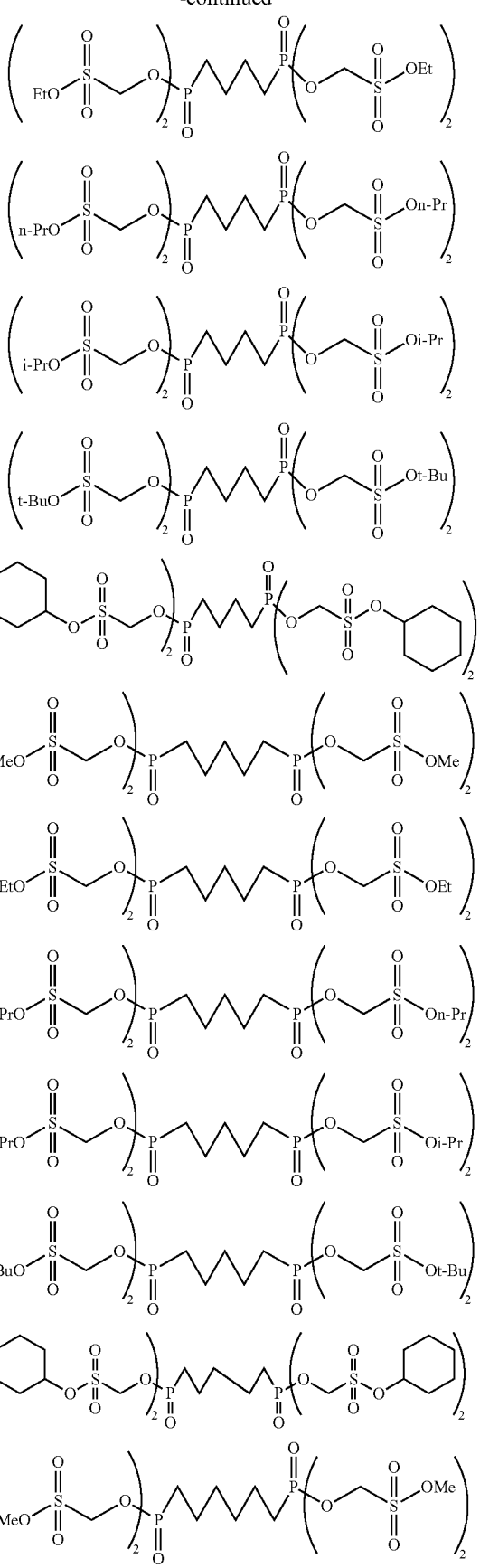

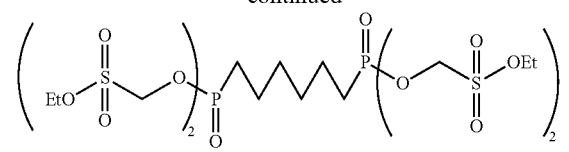
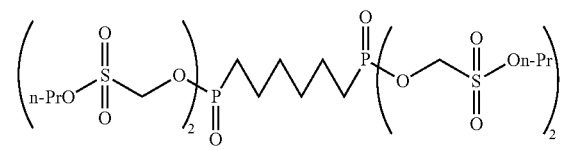
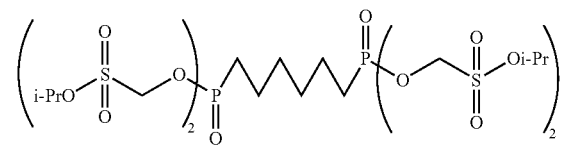
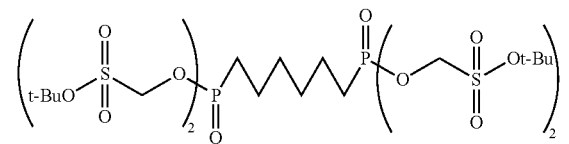
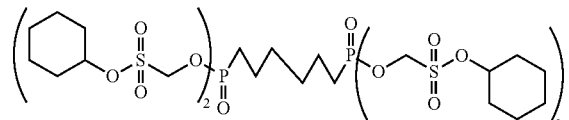
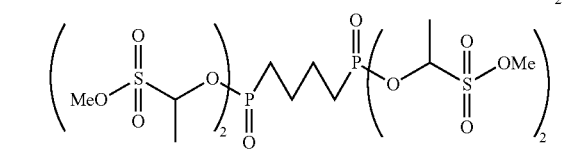
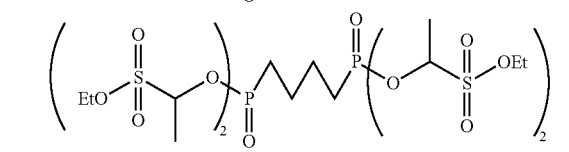
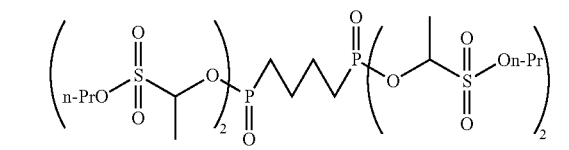
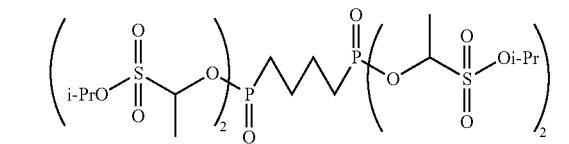
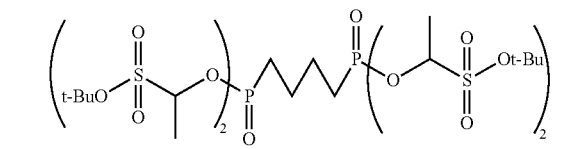
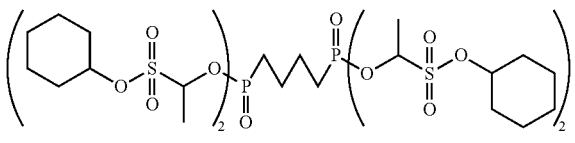
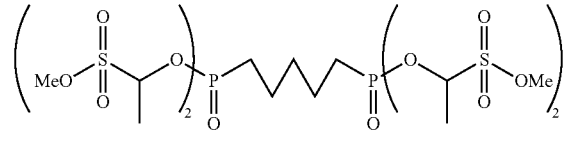
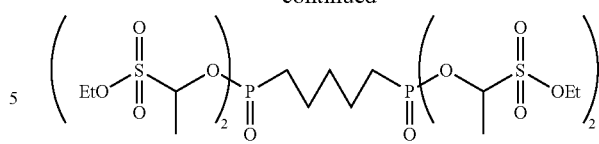
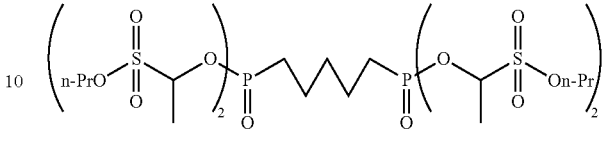
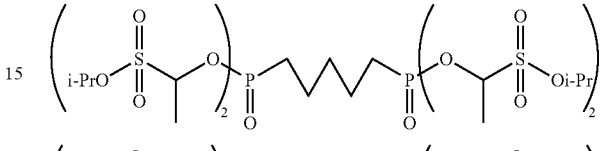
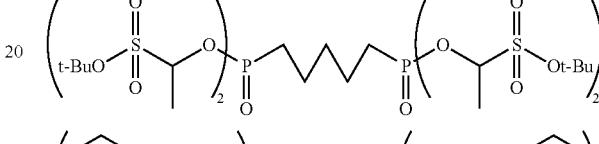
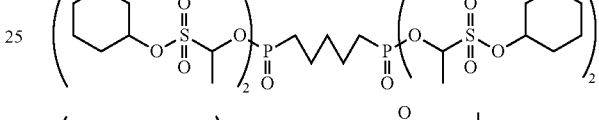
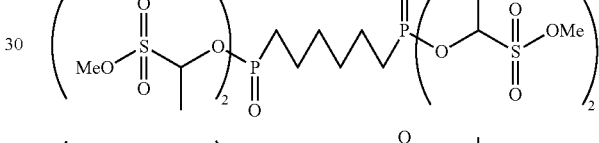
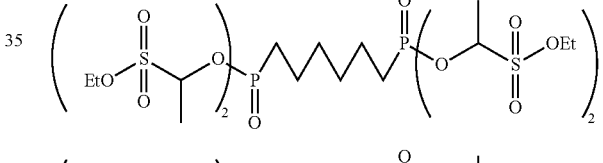
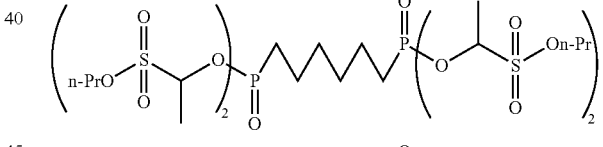
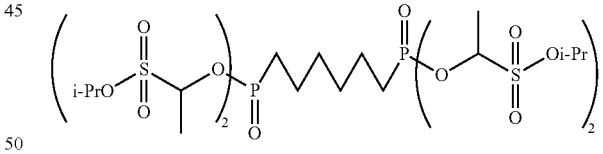
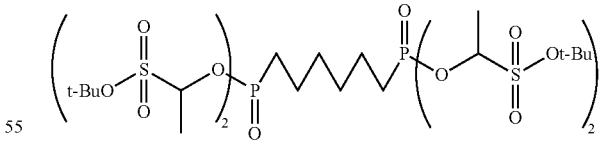
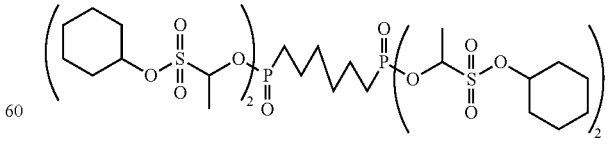
Among the above-shown compounds, more preferred is the following.
A compound which is represented by the following formula (20):

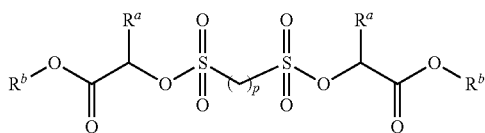

wherein $R^a$ each occurrence independently represents an alkyl group having 1 to 4 carbon atoms, $R^b$ each occurrence independently represents an alkyl group having 1 to 4 carbon atoms, and p represents an integer of 4 to 6.

As the compound represented by the formula (20), further preferred are the followings.

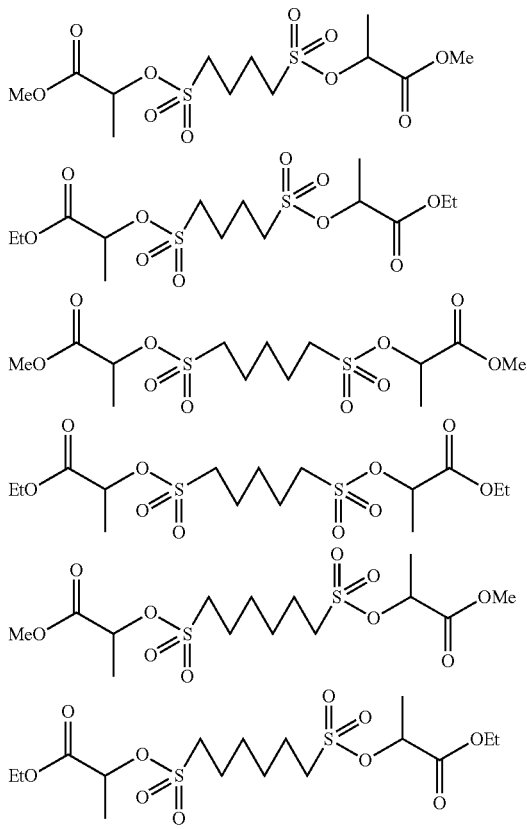

In addition to the compound represented by the formula (20), preferred is a compound represented by the following formula (30):

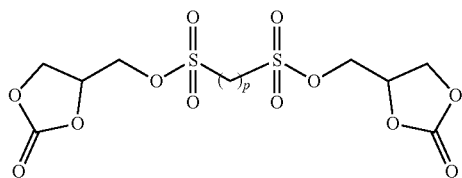

wherein p represents an integer of 4 to 6.

As the compound represented by the formula (30), further preferred are the followings.

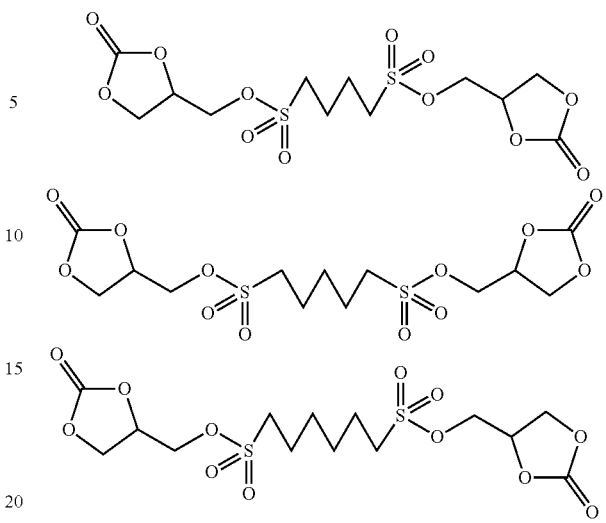

As the compound represented by the formula (1), especially preferred are the followings.

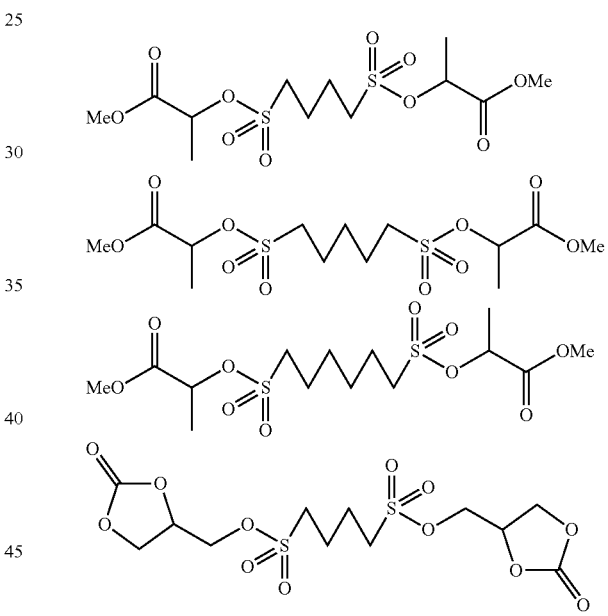

<Method for Producing the Compound>

With respect to the method for producing the compound represented by the formula (1), explanation is made taking as an example a sulfonic ester represented by the following formula (10):

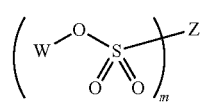

(10)

wherein:

W represents an organic group containing a heteroatom, the organic group having at least one oxygen atom as the heteroatom, m represents an integer of 2 to 4, and Z represents an organic group having 4 to 12 carbon atoms and optionally having a heteroatom.

In the above formula, with respect to W, when the portion bonded to W is replaced by a hydroxyl group, the resultant hydroxyl group is an alcoholic hydroxyl group.

The sulfonic ester represented by the formula (10) can be obtained by reacting a corresponding sulfonyl chloride with a compound having an alcohol skeleton. S (sulfur) compounds including a monosulfonic ester as a representative example are used in a wide variety of technical fields of from the medical application to the secondary battery material application, and there are a number of reports on the production of S compounds. However, with respect to a polysulfonic ester, substantially only two documents shown below specifically describe a method for producing some sulfonic esters encompassed by the formula (10) (document 1: U.S. Pat. No. 3,748,132A; and document 2: Chemistry of Materials (2004), 16(9), 1770-1774).

In document 1, there is a description of a method for producing a disulfonic ester by reacting a disulfonyl chloride and an alcohol compound. However, the disulfonic ester in this document is synthesized as an intermediate, and the synthesized disulfonic ester is subjected to the next reaction without being subjected to particular purification. Therefore, there is a possibility that the disulfonyl chloride and alcohol compound remain in the product. Further, a monosulfonic ester caused due to the reaction of only one of the two reaction sites is possibly mixed into the product. However, a method for isolating a high-purity product having the remaining compounds removed therefrom is not shown.

In document 2, a disulfonic ester is synthesized by reacting butanedisulfonyl chloride and 2-hydroxyethyl methacrylate, but there is no description about the purification, and thus there is a possibility that an impurity is mixed into the product.

Document 3 (working Examples of Japanese Unexamined Patent Publication No. 2001-92127) has a description of some sulfonic esters encompassed by the formula (10), but has no description about a method for producing them.

Document 4 (Chemical & Pharmaceutical Bulletin (1986), 34(8), 3252-66) and document 5 (Armyanskii Khimicheskii Zhurnal28_8_669.) have descriptions of methods for producing some sulfonic esters encompassed by the formula (10), and these methods are respectively a method of reacting a disulfonic acid and a diazo compound and a method of reacting a disulfonyl chloride and dimedone, and are applied only to the production of specific sulfonic esters and have no general-purpose properties as a production method. In addition, with respect to the method for synthesizing a sulfonic ester, there have been reported preparations of specific sulfonic esters by, for example, a method of reacting sulfonic acid and a diazo compound (Japanese Unexamined Patent Publication No. Sho 57-193442) or a method of reacting sulfonic acid and an orthoformate (Japanese Unexamined Patent Publication No. 2014-098857). However, these methods have no general-purpose properties and have a problem about the reactivity.

In the above-mentioned documents 1 to 5, a method for purifying the obtained sulfonic ester is not specifically shown. In the reaction in which a plurality of reaction sites are present, there is a possibility that a chemical material used as a raw material, a reaction promoter, such as a base, and further a compound caused due to the reaction of only part of the reaction sites are mixed into the product. Therefore, for obtaining an intended product with high purity, it is essential to employ a purification method unique to the product. Especially when applied to the technical field that is considerably affected by an impurity, for example, the field of a material for lithium secondary battery, the purity of the compound is important, and establishment of a purification method for the compound is essential. In view of the above problems, the present invention provides a method for producing a sulfonic ester represented by the formula (10) with high purity.

Specifically, with respect to the production of a sulfonic ester represented by the formula (10), it has been found that, after the reaction of a corresponding sulfonyl chloride and a compound having an alcoholic hydroxyl group, the obtained sulfonic ester can be isolated from the solvent by crystal deposition, and that an intended product with high purity can be obtained by this method.

The present invention is directed to a method for producing a sulfonic ester represented by the following formula (10):

wherein:

W represents an organic group containing a heteroatom, the organic group having at least one oxygen atom as the heteroatom, m represents an integer of 2 to 4, and Z represents an organic group having 4 to 12 carbon atoms and optionally having a heteroatom, wherein the method comprises the steps of:

reacting a sulfonyl chloride represented by the following formula (11):

wherein m and Z are as defined for the formula (10) and a compound having an alcoholic hydroxyl group and being represented by the following formula (12):

W—OH wherein W is as defined for the formula (10) with each other; and taking out a sulfonic ester represented by the formula (10) in the form of a solid by crystal deposition.

In the formulae (10), (11), and (12), as preferred examples of W, Z, and m, those described for X, Z, and m in the compound represented by the formula (1) are applied, but, with respect to W, when the portion bonded to W is replaced by a hydroxyl group, the resultant hydroxyl group is an alcoholic hydroxyl group. As specific examples of W's, there can be mentioned organic groups having an aliphatic portion.

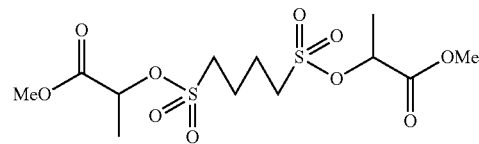

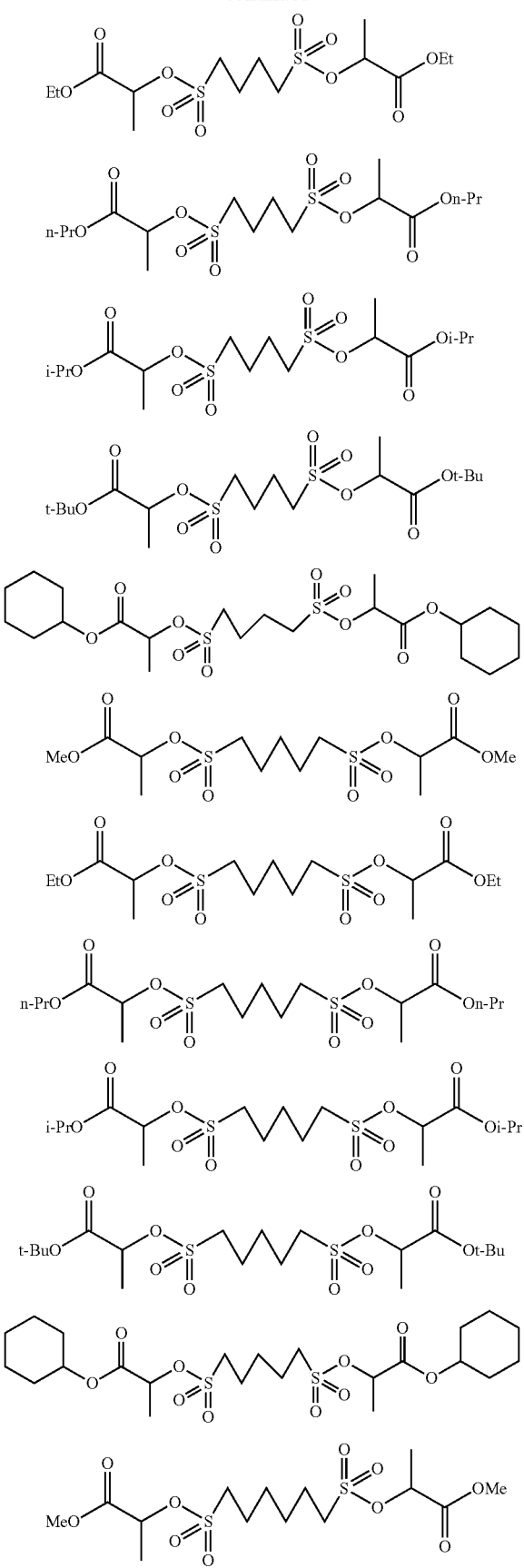
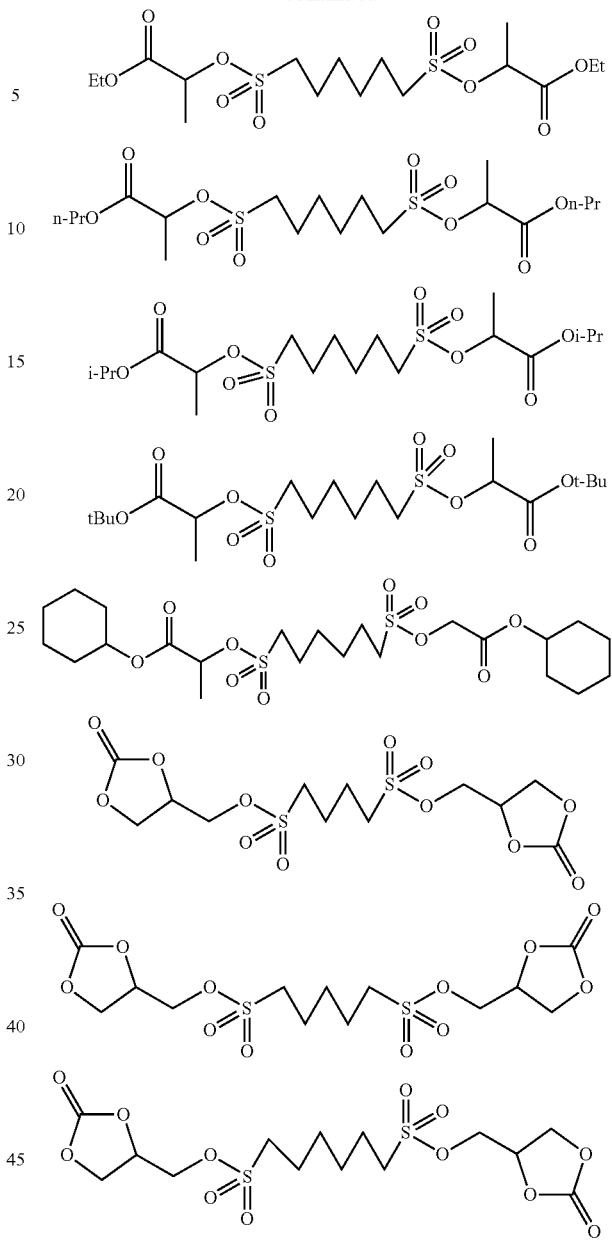
These sulfonic esters can be synthesized from the respective corresponding sulfonyl chlorides and a compound having an alcoholic hydroxyl group.
For example, a compound represented by the following formula (20):
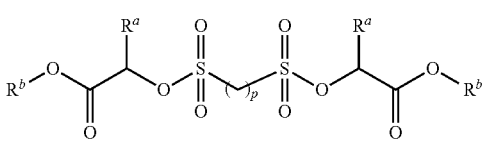
wherein:
$R^a$ each occurrence independently represents an alkyl group having 1 to 4 carbon atoms, $R^b$ each occurrence independently represents an alkyl group having 1 to 4 carbon atoms, and p represents an integer of 4 to 6 can be obtained by reacting a sulfonyl chloride represented by the following formula (21):

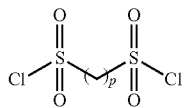
(21)

wherein p represents an integer of 4 to 6
with a compound having an alcoholic hydroxyl group and being represented by the following formula (22):

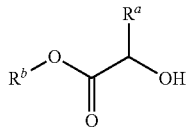
(22)

wherein:

$R^a$ independently represents an alkyl group having 1 to 4 carbon atoms, and $R^b$ independently represents an alkyl group having 1 to 4 carbon atoms.

A compound represented by the following formula (30):

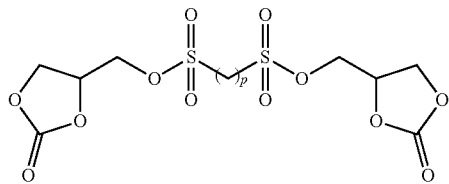
(30)

wherein p represents an integer of 4 to 6
can be obtained by reacting a sulfonyl chloride represented by the following formula (31):

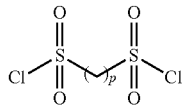
(31)

wherein p represents an integer of 4 to 6
with glycerol carbonate.

<Esterification Reaction>

The reaction of a sulfonyl chloride and a compound having an alcoholic hydroxyl group can be conducted without a solvent or in a solvent. The reaction is preferably conducted at a low temperature in a non-aqueous solvent to which a base is added as a reaction promoter.

<Solvent for Esterification Reaction>

When the reaction is conducted in a solvent, a non-aqueous solvent can be used, and one which does not react with a sulfonyl chloride is preferably used. Examples of such solvents include aliphatic hydrocarbons, such as pentane, hexane, heptane, octane, and petroleum ether; ethers, such as diethyl ether, diisopropyl ether, t-butylmethyl ether, anisole, tetrahydrofuran, dioxane, ethylene glycol dimethyl ether, and triethylene glycol dimethyl ether; halogenated hydrocarbons, such as methylene chloride, chloroform, carbon tetrachloride, 1,2-dichloroethane, trichloroethane, bromopropane, chlorobenzene, and dichlorobenzene; cyano-containing hydrocarbons, such as acetonitrile, propionitrile, butyronitrile, and benzonitrile; esters, such as ethyl acetate and butyl acetate; aromatic hydrocarbons, such as benzene, toluene, and nitrobenzene; and ketones, such as acetone and methyl ethyl ketone. These solvents may be used individually or in combination. Further, water may be mixed in such an amount that the sulfonyl chloride does not suffer decomposition. From the viewpoint of the cost, preferred are aliphatic hydrocarbons, ethers, cyano-containing hydrocarbons, esters, aromatic hydrocarbons, and ketones, and more preferred are aliphatic hydrocarbons, ethers, esters, aromatic hydrocarbons, and ketones.

The appropriate amount of the solvent used is generally in the range of from 1 to 50 times, preferably in the range of from 1 to 20 times the weight of the corresponding sulfonyl chloride.

<Base Used in the Esterification>

When a base is used, examples of bases include carbonates, such as potassium carbonate, sodium carbonate, sodium hydrogencarbonate, and potassium hydrogencarbonate; hydroxides, such as sodium hydroxide, potassium hydroxide, and lithium hydroxide; inorganic bases, such as sodium hydride, potassium hydride, metal sodium, and metal potassium; metal alkoxides, such as sodium methoxide, potassium methoxide, sodium ethoxide, and sodium t-butoxide; amines, such as triethylamine and trimethylamine; pyridines, such as pyridine and picoline; anilines, such as N,N-dimethylaniline; alkylmetal compounds, such as methyllithium, ethyllithium, propyllithium, and butyllithium; and arylmetal compounds, such as phenyllithium. The base can be appropriately selected according to the type of the solvent used. From the viewpoint of the solubility in the reaction solvent and ease of handling, preferred are amines, pyridines, and anilines, and more preferred are amines and pyridines.

The amount of the base used is preferably in the range of from 1 to 10 equivalents, further preferably in the range of from 1 to 3 equivalents with respect to the alcoholic hydroxyl group in the compound having an alcoholic hydroxyl group.

<Temperature for the Esterification>

The upper limit of the temperature for the esterification reaction is preferably 80° C. or lower, more preferably 60° C. or lower, further preferably 50° C. or lower. This reaction is an exothermic reaction, and therefore, by setting the upper limit of the temperature as mentioned above, runaway of the reaction can be suppressed, and further the formed sulfonic ester can be prevented from suffering thermal decomposition. The lower limit of the temperature for the esterification reaction is preferably −30° C. or higher, more preferably −25° C. or higher, further preferably −20° C. or higher. By setting the lower limit of the temperature as mentioned above, a danger that termination of the reaction or stagnation of the reaction occurs can be avoided.

<Time for the Esterification>

The time for the esterification reaction is preferably 30 minutes or more, more preferably 1 hour or more. A sulfonyl chloride has a plurality of reaction sites, and therefore, when the reaction time is too short, there is a possibility that a product caused due to the reaction of only part of the reaction sites is mixed, and the above-mentioned reaction time can easily avoid such a problem. On the other hand, with respect to the upper limit of the reaction time, there is no particular limitation. However, for avoiding decomposition of the formed sulfonic ester and a lowing of the productivity due to a prolonged period of time for the reaction, the reaction time can be 48 hours or less, and is preferably 24 hours or less, more preferably 10 hours or less.

The esterification reaction can be conducted under any of atmospheric pressure conditions, conditions under a pressure, and reduced pressure conditions. From the viewpoint of the productivity and safety, the esterification reaction is preferably conducted under atmospheric pressure conditions.

With respect to the reaction apparatus for the esterification reaction, there is no particular limitation, but a known apparatus made of a metal or apparatus made of a metal having on the inner surface thereof a lining of, e.g., glass or a resin, and further, for example, an apparatus made of glass or a resin can be used. From the viewpoint of, for example, the strength and safety, an apparatus made of a metal or apparatus made of a metal having a glass lining on the inner surface thereof is preferred. As a material for the metal used in the apparatus, a known material can be used, and examples include carbon steel, ferrite stainless steel, martensite stainless steel, such as SUS 410, austenite stainless steel, such as SUS 310, SUS 304, and SUS 316, clad steel, cast iron, copper, a copper alloy, aluminum, Inconel, Hastelloy, and titanium.

<Reagent Used in the Reaction>

With respect to the reagent used in the reaction in the present invention, a commercially available product may be used as such or may be purified and used. The reagent may be produced from the other compounds. With respect to the purity of the reagent, there is no particular limitation, but the reaction involves a plurality of reaction sites and hence, preferred is a reagent having a high purity such that the amount of an impurity derived from the raw materials is small, and the purity of the reagent is preferably 90% by mass or more.

<Sulfonyl Chloride>

With respect to the sulfonyl chloride, a commercially available product may be used as such or may be purified and used. When there is no commercially available product, a sulfonyl chloride may be separately produced. When a sulfonyl chloride is produced, for example, there can be mentioned the following methods for production.

a) A method for producing a sulfonyl chloride by oxidative chlorination of a corresponding alkylthiouronium salt; for example: Synlett (2013), 24(16), 2165-2169; Journal of the Chemical Society (1952), 3334-40.

b) A method for producing a sulfonyl chloride by oxidative chlorination of a corresponding thiol; for example: Inorganica Chimica Acta (2011), 369(1), 45-48; Industrial & Engineering Chemistry Process Design and Development (1964), 3(2), 164-9.

c) A method for producing a sulfonyl chloride by chlorinating a corresponding sulfonic acid or a metal salt thereof using thionyl chloride or phosphorus pentachloride; for example: Tetrahedron Letters (2009), 50(50), 7028-7031; Journal of Organic Chemistry (1960), 25, 399-402.

Of these, the method of a) in which the reaction proceeds through an alkylthiouronium salt is preferred because the reaction rate is large such that an intended sulfonyl chloride can be obtained in a short time, and the after-treatment is easy. When the counter ion of the alkylthiouronium salt is a bromide ion or an iodide ion, the oxidative chlorination reaction possibly causes a sulfonyl chloride and a sulfonyl bromide or a sulfonyl iodide to be mixed into the product. However, these can be reacted with a compound having an alcoholic hydroxyl group to be changed into an intended sulfonic ester. For this reason, these acid halides may be mixed and present.

<Oxidative Chlorination of an Alkylthiouronium Salt>

With respect to the reagent used in the oxidative chlorination of an alkylthiouronium salt, there is no particular limitation as long as it is a reagent capable of forming chlorine cations. However, preferred are chlorine gas, an aqueous solution of sodium hypochlorite, sodium chlorite, NCS, and trichloroisocyanuric acid because they exhibit high reaction rate or high reaction efficiency. Further, from the viewpoint of ease of the after-treatment for the reaction, the cost of the oxidizing reagent, and load on the environment, more preferred are an aqueous solution of hypochlorous acid and sodium chlorite, and most preferred is an aqueous solution of hypochlorous acid from the viewpoint of ease of handling. With respect to these oxidative chlorinating agents, a commercially available product may be used as such, may be purified and used, or may be produced from the other compounds. Aqueous solutions of sodium hypochlorite having various concentrations are commercially available, and, the larger the sodium hypochlorite concentration is, the more the reaction vessel efficiency is improved, or the productivity can be improved, and therefore the sodium hypochlorite concentration is preferably 5% by mass or more, more preferably 10% by mass or more, most preferably 12% by mass or more.

<Counter Ion of the Alkylthiouronium Salt>

With respect to the counter ion of the alkylthiouronium salt, there is no particular limitation, but halide ions and a sulfuric acid ion have been reported. From the viewpoint of an easy synthesis from a corresponding haloalkane, preferred are a chloride ion, a bromide ion, and an iodide ion. These counter ions may be used individually, or a mixture of two or more types of the counter ions may be used.

<Crystal Deposition>

In the present invention, the crystal deposition means an operation of taking out a sulfonic ester in the form of a solid from a solution containing the sulfonic ester represented by the formula (10). The product of a reaction of a corresponding sulfonyl chloride and a compound having an alcoholic hydroxyl group is optionally subjected to filtration, and concentrated and then mixed with a solvent, and the resultant mixture can be subjected to crystal deposition step.

The sulfonic ester may be completely dissolved in the solvent, or may be in a state in which part of the sulfonic ester is deposited in the solvent. When the operation of crystal deposition is conducted after once completely dissolving the sulfonic ester, the impurity removing power is remarkably improved, and therefore it is preferred that the sulfonic ester is once completely dissolved. As examples of the operations of taking out the sulfonic ester from the solution, there can be mentioned a method in which the solution is concentrated by volatilizing the solvent under atmospheric pressure or under a reduced pressure so as to increase the concentration of the solution, causing a solid to be deposited, a method in which another solvent having a lower solubility of an intended product is added as a poor solvent to the solution to cause deposition, a method in which the solvent and a poor solvent are used in combination to cause deposition, and a method in which the temperature of the solution is reduced from the temperature at which an intended product is dissolved to cause the intended product to be deposited. Among these, preferred are a method in which a poor solvent is added to the solution and a method in which the temperature of the solution is reduced because the intended product can be deposited efficiently in a short time. Of these, more preferred is a method in which the temperature of the solution is reduced because an increase of the size of the reaction vessel is suppressed, and a load of an operation, such as a filtration operation, can be reduced, and thus excellent productivity can be obtained. By performing the operation of crystal deposition at least once, preferably once to three times, an intended product having high purity can be obtained.

When a method in which the temperature of the solution is reduced is used, the upper limit of the temperature at which the solution containing the sulfonic ester is prepared is the boiling point of the solvent used, and is preferably 80° C. or lower, more preferably 60° C. or lower, further preferably 50° C. or lower. When the upper limit of the temperature is in the above range, it is expected that the sulfonic ester can be stably present in the solution. An intended sulfonic ester can be deposited in the form of a solid by reducing the temperature of the solution, and therefore the temperature set on the lower temperature side is not limited as long as the temperature is the upper limit or lower, and the temperature set on the lower temperature side is preferably 40° C. or lower, more preferably 30° C. or lower, further preferably 20° C. or lower. When the lower side temperature is set to be in the above range, the solubility of the sulfonic ester is reduced, making it possible to obtain an intended product in high yield.

<Solvent for Crystal Deposition>

With respect to the solvent, there is no particular limitation as long as it is a non-aqueous solvent capable of dissolving therein the sulfonic ester which is an intended product, but examples of solvents include alcohols, such as methanol, ethanol, propanol, isopropanol, butanol, isobutanol, sec-butanol, t-butanol, 1-pentanol, 3-pentanol, 2-methyl-1-butanol, 3-methyl-1-butanol, 3-methyl-2-butanol, 2-methyl-2-butanol, cyclohexanol, ethylene glycol, and trimethylene glycol; ethers, such as diethyl ether, diisopropyl ether, t-butyl methyl ether, anisole, tetrahydrofuran, dioxane, ethylene glycol dimethyl ether, and triethylene glycol dimethyl ether; halogenated hydrocarbons, such as methylene chloride, chloroform, carbon tetrachloride, 1,2-dichloroethane, trichloroethane, bromopropane, chlorobenzene, and dichlorobenzene; cyano-containing hydrocarbons, such as acetonitrile, propionitrile, butyronitrile, and benzonitrile; esters, such as ethyl acetate and butyl acetate; and ketones, such as acetone and methyl ethyl ketone. These solvents may be used individually or in combination. Of these, from the viewpoint of the solubility of the base used in the reaction or a salt thereof and ease of the drying step after the crystal deposition, preferred are low boiling-point alcohols, such as methanol and ethanol.

<Poor Solvent for Crystal Deposition>

With respect to the poor solvent, there is no particular limitation as long as the solubility of the sulfonic ester which is an intended product in the poor solvent is lower than that in the solvent and the poor solvent is miscible with the solvent, but, from the viewpoint of the solubility, examples of poor solvents include aliphatic hydrocarbons, such as pentane, hexane, heptane, octane, and petroleum ether; and aromatic hydrocarbons, such as benzene, toluene, and nitrobenzene. These solvents may be used individually or in combination. The volume of the solvent may be either larger or smaller than the volume of the poor solvent. Further, water may be used in such a small amount that water is miscible with the solvent.

<After-Treatment Subsequent to the Crystal Deposition>

In the solid of the sulfonic ester represented by the formula (10) obtained by the crystal deposition, the solvent used in the crystal deposition step possibly remains, and therefore it is preferred that the solvent is removed by drying the solid. With respect to the method for removing the solvent, there is no particular limitation, but preferred is a method of removing the solvent under a reduced pressure. The temperature condition is preferably 80° C. or lower, more preferably 60° C. or lower, further preferably 50° C. or lower, and is preferably 0° C. or higher, more preferably 5° C. or higher, further preferably 10° C. or higher. When the temperature is in the above range, the solvent can be satisfactorily removed while preventing the sulfonic ester which is an intended product from suffering thermal decomposition. From the viewpoint of both satisfactory removal and production efficiency, the time for removal is preferably 30 minutes or more, more preferably 1 hour or more, further preferably 2 hours or more, and is preferably 48 hours or less, more preferably 36 hours or less, further preferably 24 hours or less.

<Amount of the Compound Represented by the Formula (1)>

The compounds represented by the formula (1) may be used individually, or two or more types of the compounds may be used in an arbitrary combination and in an arbitrary ratio. The amount of the compound represented by the formula (1) incorporated into the non-aqueous electrolytic solution (100% by mass) is not limited, and is arbitrary as long as the effects of the present invention are not markedly sacrificed. The amount of the compound incorporated can be 0.001% by mass or more, and is preferably 0.01% by mass or more, more preferably 0.02% by mass or more, and can be 5% by mass or less, and is preferably 4% by mass or less, more preferably 2% by mass or less. When the amount of the compound incorporated is in the above range, effects for, for example, output characteristics, load characteristics, low-temperature characteristics, cycle characteristics, and high-temperature storage characteristics are further improved.

In this case, with respect to the compound represented by the formula (1), it is preferred to use the compound which is preliminarily purified to such an extent that the productivity is not markedly lowered so as to contain an impurity in an amount as small as possible.

1-4. Auxiliary

In the non-aqueous electrolyte secondary battery of the present invention, in addition to the compound represented by the formula (1), an auxiliary may be appropriately used according to the purpose. As examples of auxiliaries, there can be mentioned the below-described cyclic carbonate having a carbon-carbon unsaturated bond, unsaturated cyclic carbonate having a fluorine atom, monofluorophosphate and difluorophosphate, overcharge preventing agent, and other auxiliaries.

<Cyclic Carbonate Having a Carbon-Carbon Unsaturated Bond>

In the non-aqueous electrolytic solution of the present invention, for forming a film on the surface of the negative electrode of a non-aqueous electrolyte secondary battery to increase the life of the battery, the use of a cyclic carbonate having a carbon-carbon unsaturated bond (hereinafter, frequently referred to simply as "unsaturated cyclic carbonate") in addition to the compound represented by the formula (1) is more effective.

With respect to the unsaturated cyclic carbonate, there is no particular limitation as long as it is a cyclic carbonate having a carbon-carbon double bond, and an arbitrary unsaturated carbonate can be used. A cyclic carbonate having a substituent having an aromatic ring is included in the unsaturated cyclic carbonate.

Examples of unsaturated cyclic carbonates include vinylene carbonates, ethylene carbonates substituted with a substituent having an aromatic ring or a carbon-carbon double bond, phenyl carbonates, vinyl carbonates, and allyl carbonates.

Examples of vinylene carbonates include vinylene carbonate (hereinafter, frequently referred to simply as "VC"), methylvinylene carbonate, 4,5-dimethylvinylene carbonate, phenylvinylene carbonate, 4,5-diphenylvinylene carbonate, vinylvinylene carbonate, 4,5-vinylvinylene carbonate, allylvinylene carbonate, and 4,5-diallylvinylene carbonate.

Examples of ethylene carbonates substituted with a substituent having an aromatic ring or a carbon-carbon double bond include vinylethylene carbonate, 4,5-divinylethylene carbonate, 4-methyl-5-vinylethylene carbonate, 4-allyl-5-vinylethylene carbonate, phenylethylene carbonate, 4,5-diphenylethylene carbonate, 4-phenyl-5-vinylethylene carbonate, 4-allyl-5-phenylethylene carbonate, allylethylene carbonate, 4,5-diallylethylene carbonate, and 4-methyl-5-allylethylene carbonate.

Of these, as an unsaturated cyclic carbonate preferably used in combination with the compound represented by the formula (1), vinylene carbonate, methylvinylene carbonate, 4,5-dimethylvinylene carbonate, vinylvinylene carbonate, 4,5-vinylvinylene carbonate, allylvinylene carbonate, 4,5-diallylvinylene carbonate, vinylethylene carbonate, 4,5-divinylethylene carbonate, 4-methyl-5-vinylethylene carbonate, allylethylene carbonate, 4,5-diallylethylene carbonate, 4-methyl-5-allylethylene carbonate, or 4-allyl-5-vinylethylene carbonate is more preferably used because a stable interfacial protective film is formed.

With respect to the molecular weight of the unsaturated cyclic carbonate, there is no particular limitation, and the molecular weight of the unsaturated cyclic carbonate is arbitrary as long as the effects of the present invention are not markedly sacrificed. The molecular weight of the unsaturated cyclic carbonate is preferably 86 to 250. When the molecular weight is in the above range, the solubility of the unsaturated cyclic carbonate in the non-aqueous electrolytic solution can be easily secured, so that the effects of the present invention are likely to be satisfactorily exhibited. The molecular weight of the unsaturated cyclic carbonate is more preferably 150 or less. With respect to the method for producing the unsaturated cyclic carbonate, there is no particular limitation, and the unsaturated cyclic carbonate can be produced by a known method arbitrarily selected.

The unsaturated cyclic carbonates may be used individually, or two or more types of the unsaturated cyclic carbonates may be used in an arbitrary combination and in an arbitrary ratio. With respect to the amount of the unsaturated cyclic carbonate incorporated, there is no particular limitation, and the amount is arbitrary as long as the effects of the present invention are not markedly sacrificed. The amount of the unsaturated cyclic carbonate incorporated is preferably 0.01% by mass or more, more preferably 0.1% by mass or more, further preferably 0.2% by mass or more, and is preferably 5% by mass or less, more preferably 4% by mass or less, further preferably 3% by mass or less, based on the mass of the non-aqueous electrolytic solution (100% by mass). When the amount of the unsaturated cyclic carbonate incorporated is in the above range, the non-aqueous electrolyte secondary battery is likely to exhibit a satisfactory cycle characteristics improvement effect, and further it is easy to avoid a problem, such as a lowering of the discharge capacity maintaining ratio due to the deterioration of the high-temperature storage characteristics resulting in an increase of gas generation. Meanwhile, when the amount of the unsaturated cyclic carbonate is too small, the effects of the present invention are unlikely to be satisfactorily exhibited, and, when the amount of the unsaturated cyclic carbonate is too large, the resistance is likely to be increased to lower the output or load characteristics.

<Unsaturated Cyclic Carbonate Having a Fluorine Atom>

As the unsaturated cyclic carbonate having a fluorine atom, a cyclic carbonate having an unsaturated bond and a fluorine atom (hereinafter, frequently referred to simply as "fluorinated unsaturated cyclic carbonate") is preferably used. With respect to the number of the fluorine atom(s) of the fluorinated unsaturated cyclic carbonate, there is no particular limitation as long as the number is 1 or more. Especially, the number of the fluorine atom(s) is generally 6 or less, preferably 4 or less, most preferably 1 or 2.

Examples of fluorinated unsaturated cyclic carbonates include fluorinated vinylene carbonate derivatives and fluorinated ethylene carbonate derivatives substituted with a substituent having an aromatic ring or a carbon-carbon double bond.

Examples of fluorinated vinylene carbonate derivatives include 4-fluorovinylene carbonate, 4-fluoro-5-methylvinylene carbonate, 4-fluoro-5-phenylvinylene carbonate, 4-allyl-5-fluorovinylene carbonate, and 4-fluoro-5-vinylvinylene carbonate.

Examples of fluorinated ethylene carbonate derivatives substituted with a substituent having an aromatic ring or a carbon-carbon double bond include 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, 4,5-difluoro-4,5-diallylethylene carbonate, 4-fluoro-4-phenylethylene carbonate, 4-fluoro-5-phenylethylene carbonate, 4,4-difluoro-5-phenylethylene carbonate, and 4,5-difluoro-4-phenylethylene carbonate.

Of these, as a fluorinated unsaturated cyclic carbonate preferably used in combination with the compound represented by the formula (1), 4-fluorovinylene carbonate, 4-fluoro-5-methylvinylene carbonate, 4-fluoro-5-vinylvinylene carbonate, 4-allyl-5-fluorovinylene carbonate, 4-fluoro-4-vinylethylene carbonate, 4-fluoro-4-allylethylene carbonate, 4-fluoro-5-vinylethylene carbonate, 4-fluoro-5-allylethylene carbonate, 4,4-difluoro-4-vinylethylene carbonate, 4,4-difluoro-4-allylethylene carbonate, 4,5-difluoro-4-vinylethylene carbonate, 4,5-difluoro-4-allylethylene carbonate, 4-fluoro-4,5-divinylethylene carbonate, 4-fluoro-4,5-diallylethylene carbonate, 4,5-difluoro-4,5-divinylethylene carbonate, or 4,5-difluoro-4,5-diallylethylene carbonate is more preferably used because a stable interfacial protective film is formed.

With respect to the molecular weight of the fluorinated unsaturated cyclic carbonate, there is no particular limitation, and the molecular weight of the fluorinated unsaturated cyclic carbonate is arbitrary as long as the effects of the present invention are not markedly sacrificed. The molecular weight of the fluorinated unsaturated cyclic carbonate is preferably 86 to 250. When the molecular weight is in the above range, the solubility of the fluorinated cyclic carbonate in the non-aqueous electrolytic solution can be easily secured, so that the effects of the present invention are likely to be exhibited. With respect to the method for producing the fluorinated unsaturated cyclic carbonate, there is no particular limitation, and the fluorinated unsaturated cyclic carbonate can be produced by a known method arbitrarily selected. The molecular weight of the fluorinated unsaturated cyclic carbonate is more preferably 150 or less.

The fluorinated unsaturated cyclic carbonates may be used individually, or two or more types of the fluorinated unsaturated cyclic carbonates may be used in an arbitrary combination and in an arbitrary ratio. With respect to the amount of the fluorinated unsaturated cyclic carbonate incorporated, there is no particular limitation, and the amount is arbitrary as long as the effects of the present invention are not markedly sacrificed. The amount of the fluorinated unsaturated cyclic carbonate incorporated is preferably 0.01% by mass or more, more preferably 0.1% by mass or more, further preferably 0.2% by mass or more, and is preferably 5% by mass or less, more preferably 4% by mass or less, further preferably 3% by mass or less, based on the mass of the non-aqueous electrolytic solution (100% by mass). When the amount of the fluorinated unsaturated cyclic carbonate incorporated is in the above range, the non-aqueous electrolyte secondary battery is likely to exhibit a satisfactory cycle characteristics improvement effect, and further it is easy to avoid a problem, such as a lowering of the discharge capacity maintaining ratio due to the deterioration of the high-temperature storage characteristics resulting in an increase of gas generation. Meanwhile, when the amount of the fluorinated unsaturated cyclic carbonate is too small, the effects of the present invention are unlikely to be satisfactorily exhibited, and, when the amount of the fluorinated unsaturated cyclic carbonate is too large, the resistance is likely to be increased to lower the output or load characteristics.

<Monofluorophosphate and Difluorophosphate>

With respect to the counter cation of the monofluorophosphate and difluorophosphate, there is no particular limitation, but examples of counter cations include lithium, sodium, potassium, magnesium, calcium, and an ammonium represented by $NR_5R_6R_7R_8$ (wherein each of $R_5$ to $R_8$ independently represents a hydrogen atom or an organic group having 1 to 12 carbon atoms).

With respect to the organic group having 1 to 12 carbon atoms represented by $R_5$ to $R_8$ for the ammonium, there is no particular limitation, but examples of the organic groups include an alkyl group which may be substituted with a halogen atom, a cycloalkyl group which may be substituted with a halogen atom or an alkyl group, an aryl group which may be substituted with a halogen atom or an alkyl group, and a nitrogen atom-containing heterocyclic group which may have a substituent. Of these, each of $R_5$ to $R_8$ is preferably independently a hydrogen atom, an alkyl group, a cycloalkyl group, or a nitrogen atom-containing heterocyclic group.

Specific examples of monofluorophosphates and difluorophosphates include lithium monofluorophosphate, sodium monofluorophosphate, potassium monofluorophosphate, lithium difluorophosphate, sodium difluorophosphate, and potassium difluorophosphate, and preferred are lithium monofluorophosphate and lithium difluorophosphate, and more preferred is lithium difluorophosphate.

The monofluorophosphates and difluorophosphates may be used individually, or two or more types of the monofluorophosphates and difluorophosphates may be used in an arbitrary combination and in an arbitrary ratio. With respect to the amount of the monofluorophosphate and difluorophosphate incorporated, there is no particular limitation, and the amount is arbitrary as long as the effects of the present invention are not markedly sacrificed. The amount of the monofluorophosphate and difluorophosphate incorporated is preferably 0.001% by mass or more, more preferably 0.01% by mass or more, further preferably 0.1% by mass or more, and is preferably 5% by mass or less, more preferably 4% by mass or less, further preferably 3% by mass or less, based on the mass of the non-aqueous electrolytic solution (100% by mass). When the amount of the monofluorophosphate and difluorophosphate incorporated is in the above range, the non-aqueous electrolyte secondary battery is likely to exhibit a satisfactory cycle characteristics improvement effect, and further it is easy to avoid a problem, such as a lowering of the discharge capacity maintaining ratio due to the deterioration of the high-temperature storage characteristics resulting in an increase of gas generation.

<Overcharge Preventing Agent>

In the non-aqueous electrolytic solution of the present invention, for effectively preventing the non-aqueous electrolyte secondary battery in the state of, for example, overcharge from bursting or burning, an overcharge preventing agent can be used.

Examples of overcharge preventing agents include aromatic compounds, such as biphenyl, an alkylbiphenyl, terphenyl, partially hydrogenated terphenyl, cyclohexylbenzene, t-butylbenzene, t-amylbenzene, diphenyl ether, and dibenzofuran; the aromatic compounds which are partially fluorinated, such as 2-fluorobiphenyl, o-cyclohexylfluorobenzene, and p-cyclohexylfluorobenzene; and fluorine-containing anisole compounds, such as 2,4-difluoroanisole, 2,5-difluoroanisole, 2,6-difluoroanisole, and 3,5-difluoroanisole. Of these, preferred are aromatic compounds, such as biphenyl, an alkylbiphenyl, terphenyl, partially hydrogenated terphenyl, cyclohexylbenzene, t-butylbenzene, t-amylbenzene, diphenyl ether, and dibenzofuran. These may be used individually or in combination. When two or more types of the overcharge preventing agents are used in combination, particularly, from the viewpoint of obtaining an excellent balance between the overcharge preventing properties and the high-temperature storage characteristics, preferred are a combination of cyclohexylbenzene and t-butylbenzene or t-amylbenzene, and a combination of at least one member selected from aromatic compounds containing no oxygen, such as biphenyl, an alkylbiphenyl, terphenyl, partially hydrogenated terphenyl, cyclohexylbenzene, t-butylbenzene, and t-amylbenzene, and at least one member selected from oxygen-containing aromatic compounds, such as diphenyl ether and dibenzofuran.

With respect to the amount of the overcharge preventing agent incorporated, there is no particular limitation, and the amount is arbitrary as long as the effects of the present invention are not markedly sacrificed. The amount of the overcharge preventing agent is preferably 0.1 to 5% by mass, based on the mass of the non-aqueous electrolytic solution (100% by mass). When the amount of the overcharge preventing agent is in the above range, the overcharge preventing agent is likely to satisfactorily exhibit an effect thereof, and further it is easy to avoid a problem, such as deterioration of characteristics of the battery, for example, high-temperature storage characteristics. The amount of the overcharge preventing agent is more preferably 0.2% by mass or more, further preferably 0.3% by mass or more, especially preferably 0.5% by mass or more, and is more preferably 3% by mass or less, further preferably 2% by mass or less.

<Other Auxiliaries>

In the non-aqueous electrolytic solution of the present invention, another known auxiliary can be used. Examples of other auxiliaries include carbonate compounds, such as erythritan carbonate, spiro-bis-dimethylene carbonate, and methoxyethyl-methyl carbonate; carboxylic anhydrides, such as succinic anhydride, glutaric anhydride, maleic anhydride, citraconic anhydride, glutaconic anhydride, itaconic anhydride, diglycolic anhydride, cyclohexanedicarboxylic anhydride, and phenylsuccinic anhydride, spiro compounds, such as 2,4,8,10-tetraoxaspiro[5.5]undecane and 3,9-divinyl-2,4,8,10-tetraoxaspiro[5.5]undecane; sulfur-containing compounds, such as ethylene sulfite, 1,3-propane sultone, 1-fluoro-1,3-propane sultone, 2-fluoro-1,3-propane sultone, 3-fluoro-1,3-propane sultone, 1-propene-1,3-sultone, 1-fluoro-1-propene-1,3-sultone, 2-fluoro-1-propene-1,3-sultone, 3-fluoro-1-propene-1,3-sultone, 1,4-butane sultone, 1-butene-1,4-sultone, 3-butene-1,4-sultone, methyl fluorosulfonate, ethyl fluorosulfonate, methyl methanesulfonate, ethyl methanesulfonate, busulfane, sulfolene, diphenyl sulfone, N,N-dimethylmethanesulfonamide, and N,N-diethylmethanesulfonamide; nitrogen-containing compounds, such as 1-methyl-2-pyrrolidinone, 1-methyl-2-piperidone, 3-methyl-2-oxazolidinone, 1,3-dimethyl-2-imidazolidinone, and N-methylsuccinimide; hydrocarbon compounds, such as heptane, octane, nonane, decane, and cycloheptane; and fluorine-containing aromatic compounds, such as fluorobenzene, difluorobenzene, hexafluorobenzene, and benzotrifluoride. These may be used individually or in combination. By adding the above auxiliary, the capacity maintaining characteristics and cycle characteristics after the high-temperature storage can be improved.

With respect to the amount of the other auxiliary incorporated, there is no particular limitation, and the amount is arbitrary as long as the effects of the present invention are not markedly sacrificed. The amount of the other auxiliary incorporated is preferably 0.01 to 5% by mass, based on the mass of the non-aqueous electrolytic solution (100% by mass). When the amount of the other auxiliary incorporated is in the above range, the other auxiliary is likely to satisfactorily exhibit an effect thereof, and further it is easy to avoid a problem, such as deterioration of characteristics of the battery, for example, high-load discharge characteristics. The amount of the other auxiliary incorporated is more preferably 0.1% by mass or more, further preferably 0.2% by mass or more, and is more preferably 3% by mass or less, further preferably 1% by mass or less.

The non-aqueous electrolytic solution of the present invention encompasses a non-aqueous electrolytic solution present inside of a non-aqueous electrolyte secondary battery. Specifically, the non-aqueous electrolytic solution of the present invention encompasses: a non-aqueous electrolytic solution present in a non-aqueous electrolyte secondary battery which is obtained by separately synthesizing constituents of a non-aqueous electrolytic solution, for example, an electrolyte (for example, a lithium salt), a non-aqueous solvent, a compound represented by the formula (1), and an arbitrary auxiliary, and substantially isolating the synthesized constituents, and preparing a non-aqueous electrolytic solution from the resultant constituents, and injecting the electrolytic solution into a battery separately assembled; a non-aqueous electrolytic solution present in a non-aqueous electrolyte secondary battery which is obtained by individually placing the constituents of the non-aqueous electrolytic solution of the present invention in the battery, and mixing them with each other within the battery to obtain the same composition as that of the non-aqueous electrolytic solution of the present invention; and a non-aqueous electrolytic solution present in a non-aqueous electrolyte secondary battery which is obtained by generating the constituents constituting the non-aqueous electrolytic solution of the present invention within the non-aqueous electrolyte secondary battery to obtain the same composition as that of the non-aqueous electrolytic solution of the present invention.

2. Construction of the Battery

The non-aqueous electrolytic solution of the present invention is advantageously used as an electrolytic solution for a non-aqueous electrolyte secondary battery, especially for a secondary battery, for example, a lithium secondary battery. The non-aqueous electrolyte secondary battery of the present invention can be of a known structure, and typically comprises a negative electrode and a positive electrode each being capable of having occluded therein and releasing metal ions (for example, lithium ions), and the non-aqueous electrolytic solution of the present invention.

2-1. Negative Electrode

With respect to the negative electrode active material used in the negative electrode, there is no particular limitation as long as it is capable of electrochemically having occluded therein and releasing metal ions (for example, lithium ions). Specific examples of such active materials include carbonaceous materials, alloy materials, and lithium-containing metal composite oxide materials. These materials may be used individually, or two or more types of the materials may be used in an arbitrary combination.

<Negative Electrode Active Material>

Examples of negative electrode active materials include carbonaceous materials, alloy materials, and lithium-containing metal composite oxide materials.

With respect to the carbonaceous material used as the negative electrode active material, preferred is one selected from:

(1) natural graphite;

(2) an artificial carbonaceous material, and a carbonaceous material obtained by subjecting an artificial graphite material to heat treatment in the range of from 400 to 3,200° C. once or more times;

(3) a carbonaceous material such that the negative electrode active material layer comprises at least two types or more of carbonaceous substances having different crystalline properties, and/or has an interface at which the carbonaceous substances having different crystalline properties are in contact with each other; and (4) a carbonaceous material such that the negative electrode active material layer comprises at least two types or more of carbonaceous substances having different orientation properties, and/or has an interface at which the carbonaceous substances having different orientation properties are in contact with each other because excellent balance between the initial irreversible capacity and the high current-density charge-discharge characteristics is obtained.

The carbonaceous materials of items (1) to (4) above may be used individually, or two or more types of the carbonaceous materials may be used in an arbitrary combination and in an arbitrary ratio.

Examples of the artificial carbonaceous materials and artificial graphite materials of item (2) above include natural graphite, coal coke, petroleum coke, coal pitch, petroleum pitch, and materials obtained by subjecting these pitches to oxidation treatment, needle coke, pitch coke, and carbon materials obtained by partially graphitizing the above coke, thermal decomposition products of an organic material, such as furnace black, acetylene black, and pitch carbon fiber, organic materials capable of being carbonized and carbides thereof, and a solution obtained by dissolving an organic material capable of being carbonized in a low-molecular organic solvent, such as benzene, toluene, xylene, quinoline, or n-hexane, and carbides thereof.

With respect to the alloy material used as the negative electrode active material, there is no particular limitation as long as it is capable of having occluded therein and releasing lithium, and the alloy material may be any of lithium simple substance, a simple substance metal and an alloy forming a lithium alloy, and a compound, such as an oxide, carbide, nitride, silicide, sulfide, or phosphide of the above metal or alloy. As the simple substance metal and alloy forming a lithium alloy, preferred are materials containing a metal or semi-metal element (namely, excluding carbon) belonging to Groups 13 and 14 of the Periodic Table, and more preferred are simple substance metals of aluminum, silicon, and tin (which are, hereinafter, frequently referred to as "specific metal elements") and alloys and compounds containing the above atom. These materials may be used individually, or two or more types of the materials may be used in an arbitrary combination and in an arbitrary ratio.

Examples of negative electrode active materials having at least one atom selected from the specific metal elements include respective metal simple substances of the specific metal elements, alloys comprising two or more specific metal elements, alloys comprising one or two or more specific metal elements and one or two or more the other metal elements, compounds containing one or two or more specific metal elements, and composite compounds, such as an oxide, carbide, nitride, silicide, sulfide, or phosphide of the above compound. By using the above metal simple substance, alloy, or metal compound as the negative electrode active material, the battery can be increased in the capacity.

Further, there can be mentioned compounds formed from the above composite compound complicatedly bonded to several elements, such as a metal simple substance, an alloy, or a nonmetallic element. Specifically, for example, with respect to silicon or tin, an alloy of the element and a metal which does not act as a negative electrode can be used. For example, in the case of tin, there can be used a complicated compound comprising a combination of tin, a metal other than tin and silicon, which acts as a negative electrode, a metal which does not act as a negative electrode, and a nonmetallic element so as to contain 5 to 6 elements.

Among these negative electrode active materials, preferred are respective metal simple substances of the specific metal elements, alloys of two or more specific metal elements, and oxides, carbides, nitrides and the like of the specific metal elements because the resultant battery has a large capacity per unit mass. Particularly, from the viewpoint of the capacity per unit mass and the load on the environment, preferred are metal simple substances, alloys, oxides, carbides, nitrides and the like of silicon and/or tin.

With respect to the lithium-containing metal composite oxide material used as the negative electrode active material, there is no particular limitation as long as it is capable of having occluded therein and releasing lithium. However, from the viewpoint of achieving high current-density charge-discharge characteristics, preferred are materials containing titanium and lithium, more preferred are lithium-containing composite metal oxide materials containing titanium, and further preferred are composite oxides of lithium and titanium (hereinafter, frequently referred to simply as "lithium-titanium composite oxide(s)"). That is, the negative electrode active material for non-aqueous electrolyte secondary battery, which contains a lithium-titanium composite oxide having a spinel structure, is especially preferably used because the output resistance is markedly reduced.

Further, preferred are the lithium-titanium composite oxides in which lithium or titanium is replaced by another metal element, for example, at least one element selected from the group consisting of Na, K, Co, Al, Fe, Mg, Cr, Ga, Cu, Zn, and Nb.

The above-mentioned metal oxide is preferably a lithium-titanium composite oxide represented by the general formula (A) below wherein, in the general formula (A), the relationships: $0.7 \leq x \leq 1.5$, $1.5 \leq y \leq 2.3$, and $0 \leq z \leq 1.6$ are satisfied, because the structure is stable upon doping or dedoping for lithium ions.

$$Li_x Ti_y M_z O_4 \hspace{2cm} (A)$$

Wherein, in the general formula (A), M represents at least one element selected from the group consisting of Na, K, Co, Al, Fe, Mg, Cr, Ga, Cu, Zn, and Nb.

Among the compositions represented by the general formula (A) above, especially preferred are structures which respectively satisfy the following relationships:

(a) $1.2 \leq x \leq 1.4$, $1.5 \leq y \leq 1.7$, $z=0$
(b) $0.9 \leq x \leq 1.1$, $1.9 \leq y \leq 2.1$, $z=0$
(c) $0.7 \leq x \leq 0.9$, $2.1 \leq y \leq 2.3$, $z=0$ because the balance of battery performance is excellent.

Especially preferred representative compositions of the above compound are $Li_{4/3}Ti_{5/3}O_4$ for structure (a), $Li_1Ti_2O_4$ for structure (b), and $Li_{4/5}Ti_{11/5}O_4$ for structure (c). Further, with respect to the structure in which $Z \neq 0$, as a preferred example, there can be mentioned $Li_{4/3}Ti_{4/3}Al_{1/3}O_4$.

<Physical Properties of a Carbonaceous Material>

When a carbonaceous material is used as the negative electrode active material, one having the following physical properties is desirable.

(X-Ray Parameters)

With respect to the carbonaceous material, the d value (distance between layers) on the lattice plane (002 plane) as determined by X-ray diffraction in accordance with a Gakushin method is preferably 0.335 nm or more, and is generally 0.360 nm or less, preferably 0.350 nm or less, further preferably 0.345 nm or less. Further, the crystallite size (Lc) of the carbonaceous material as determined by X-ray diffraction in accordance with a Gakushin method is preferably 1.0 nm or more, especially, further preferably 1.5 nm or more.

(Volume-Based Average Particle Diameter)

The volume-based average particle diameter of the carbonaceous material is a volume-based average particle diameter (median diameter) as determined by a laser diffraction/scattering method, and is generally 1 μm or more, preferably 3 μm or more, further preferably 5 μm or more, especially preferably 7 μm or more, and is generally 100 μm or less, preferably 50 μm or less, more preferably 40 μm or less, further preferably 30 μm or less, especially preferably 25 μm or less.

When the volume-based average particle diameter of the carbonaceous material is smaller than the above range, the irreversible capacity is likely to be increased to cause a loss of the initial battery capacity. On the other hand, when the volume-based average particle diameter is larger than the above range, a non-uniform coating surface is likely to be formed in the preparation of an electrode by application and this is not desirable in view of the battery production process.

The measurement of a volume-based average particle diameter is conducted using a laser diffraction/scattering-type particle size distribution meter (LA-700, manufactured by HORIBA, Ltd.) with respect to a carbon powder dispersed in a 0.2% by mass aqueous solution (about 10 mL) of polyoxyethylene (20) sorbitan monolaurate which is a surfactant. The median diameter determined by the above measurement is defined as a volume-based average particle diameter of the carbonaceous material in the present invention.

(Raman R Value, Raman Half Band Width)

The Raman R value of the carbonaceous material is a value measured using an argon-ion laser Raman spectrum method, and is generally 0.01 or more, preferably 0.03 or more, further preferably 0.1 or more, and is generally 1.5 or less, preferably 1.2 or less, further preferably 1 or less, especially preferably 0.5 or less.

With respect to the Raman half band width at around 1,580 cm$^{-1}$ of the carbonaceous material, there is no particular limitation, but the Raman half band width is generally 10 cm$^{-1}$ or more, preferably 15 cm$^{-1}$ or more, and is generally 100 cm$^{-1}$ or less, preferably 80 cm$^{-1}$ or less, further preferably 60 cm$^{-1}$ or less, especially preferably 40 cm$^{-1}$ or less.

The Raman R value and Raman half band width are indices indicating the crystalline properties of the surface of the carbonaceous material. It is preferred that the carbonaceous material has appropriate crystalline properties from the viewpoint of the chemical stability, and has crystalline properties such that sites between the layers which Li goes into do not disappear due to charging and discharging, that is, the charge acceptance properties do not deteriorate. When the negative electrode applied onto the current collector is increased in density by pressing, the crystals are likely to be oriented in the direction parallel to the electrode plate, and therefore it is preferred to take this tendency into consideration. When the Raman R value or Raman half band width is in the above range, a preferred film can be formed on the surface of the negative electrode to improve the storage characteristics, cycle characteristics, and load characteristics, and further a lowering of the efficiency and gas generation caused due to the reaction with the non-aqueous electrolytic solution can be suppressed.

The measurement of a Raman spectrum is conducted using a Raman spectrometer (Raman Spectrometer, manufactured by JASCO Corporation) by allowing a sample to freely fall in a measurement cell so as to fill the cell with the sample and, while irradiating the surface of the sample in the cell with an argon ion laser, rotating the cell within the plane perpendicular to the laser. With respect to the obtained Raman spectrum, intensity IA of peak PA appearing at around 1,580 cm$^{-1}$ and intensity IB of peak PB appearing at around 1,360 cm$^{-1}$ are measured, and an intensity ratio R (R=IB/IA) is determined by calculation. The Raman R value determined by the above measurement is defined as a Raman R value of the carbonaceous material in the present invention. Further, a half band width of peak PA appearing at around 1,580 cm$^{-1}$ in the obtained Raman spectrum is measured, and this is defined as a Raman half band width of the carbonaceous material in the present invention.

Conditions for the above Raman measurement are as follows.

Wavelength of argon ion laser: 514.5 nm
Laser power on a sample: 15 to 25 mW
Resolution: 10 to 20 cm$^{-1}$
Measuring range: 1,100 to 1,730 cm$^{-1}$
Analysis for Raman R value and Raman half band width:
  Background processing
Smoothing processing: Simple average, convolution 5 points (BET Specific Surface Area)

The BET specific surface area of the carbonaceous material is a value of a specific surface area measured using a BET method, and is generally 0.1 m$^2$·g$^{-1}$ or more, preferably 0.7 m$^2$·g$^{-1}$ or more, further preferably 1.0 m$^2$·g$^{-1}$ or more, especially preferably 1.5 m$^2$·g$^{-1}$ or more, and is generally 100 m$^2$·g$^{-1}$ or less, preferably 25 m$^2$·g$^{-1}$ or less, further preferably 15 m$^2$·g$^{-1}$ or less, especially preferably 10 m$^2$·g$^{-1}$ or less.

When the BET specific surface area value of the carbonaceous material is in the above range, deposition of lithium on the surface of the electrode can be suppressed and, meanwhile, gas generation caused due to the reaction with the non-aqueous electrolytic solution can be suppressed.

The measurement of a specific surface area by a BET method is conducted using a surface area meter (Fully-automatic surface area measurement apparatus, manufactured by Ohkura Riken Inc.) by subjecting a sample to predrying under a nitrogen gas flow at 350° C. for 15 minutes, and then making a measurement in accordance with a nitrogen adsorption BET single-point method by a gas flow method using a nitrogen-helium mixed gas accurately prepared so that the nitrogen pressure relative to atmospheric pressure becomes 0.3. The specific surface area determined by the above measurement is defined as a BET specific surface area of the carbonaceous material in the present invention.

(Roundness)

When a roundness is measured as the degree of sphere of the carbonaceous material, the roundness preferably falls within the range shown below. The roundness is defined by "Roundness=(Length of the circumference of the particle equivalent circle having the same area as that of the projected particle shape)/(Length of the actual circumference of the projected particle shape)", and, when the material has a roundness of 1, it is theoretically a true sphere. The roundness of the particles of the carbonaceous material having a particle diameter in the range of from 3 to 40 µm is desirably close to 1, and is preferably 0.1 or more, especially, preferably 0.5 or more, more preferably 0.8 or more, further preferably 0.85 or more, especially preferably 0.9 or more. With respect to the high current-density charge-discharge characteristics, the larger the roundness is, the more the filling properties are improved, and the resistance between the particles can be reduced, and therefore the high current-density charge-discharge characteristics are improved. Accordingly, the roundness is preferably higher as in the above-mentioned range.

The measurement of a roundness is conducted using a flow-type particle image analyzer (FPIA, manufactured by Sysmex Corporation). About 0.2 g of a sample is dispersed in a 0.2% by mass aqueous solution (about 50 mL) of polyoxyethylene (20) sorbitan monolaurate which is a surfactant, and irradiated with ultrasonic waves with 28 kHz at a power of 60 W for one minute and then, a detection range of from 0.6 to 400 µm is designated, and a roundness is measured with respect to the particles having a particle diameter in the range from 3 to 40 µm. The roundness determined by the above measurement is defined as a roundness of the carbonaceous material in the present invention.

With respect to the method for improving the roundness, there is no particular limitation. However, preferred are the particles which have been subjected to sphere forming treatment so as to be spherical because an electrode formed from such particles is advantageous in that the shapes of voids between the particles are uniform. As examples of the sphere forming treatments, there can be mentioned a method in which a shearing force or a compressive force is applied to particles to mechanically force them to be close to a sphere, and a mechanical or physical treatment method in which a plurality of microparticles are subjected to granulation using a binder or an adhesive force of the particles themselves.

(Tap Density)

The tap density of the carbonaceous material is generally 0.1 g·cm$^{-3}$ or more, preferably 0.5 g·cm$^{-3}$ or more, further preferably 0.7 g·cm$^{-3}$ or more, especially preferably 1 g·cm$^{-3}$ or more, and is preferably 2 g·cm$^{-3}$ or less, further preferably 1.8 g·cm$^{-3}$ or less, especially preferably 1.6 g·cm$^{-3}$ or less. When the tap density is in the above range, the battery capacity can be secured, and further an increase of the resistance between the particles can be suppressed.

The measurement of a tap density is conducted by passing a sample through a sieve having a sieve opening of 300 μm and allowing the sample to fall in a 20 cm$^3$ tapping cell to fill the cell with the sample so that the sample reaches the upper end surface of the cell, and then, using a powder density measurement apparatus (for example, Tap Denser, manufactured by Seishin Enterprise Co., Ltd.), subjecting the resultant sample to 1,000-time tapping with a stroke length of 10 mm, and determining a tap density by making a calculation from a volume measured at that time and the mass of the sample. The tap density determined by the above measurement is defined as a tap density of the carbonaceous material in the present invention.

(Orientation Ratio)

The orientation ratio of the carbonaceous material is generally 0.005 or more, preferably 0.01 or more, further preferably 0.015 or more, and is generally 0.67 or less. When the orientation ratio is in the above range, excellent high-density charge-discharge characteristics can be secured. The above-mentioned upper limit of the range is the theoretical upper limit of the orientation ratio of the carbonaceous material.

An orientation ratio is measured by X-ray diffraction with respect to a sample which has been subjected to press molding. A molding machine having a diameter of 17 mm is filled with 0.47 g of a sample, and the sample is compressed at 58.8 MN·m$^{-2}$, and the resultant molded material is set using clay so as to be on the same plane as the plane of a sample holder for measurement, and subjected to X-ray diffraction measurement. From the obtained peak intensities of the (110) diffraction and (004) diffraction of carbon, a ratio represented by (110) diffraction peak intensity/(004) diffraction peak intensity is determined by calculation. The orientation ratio determined by the above measurement is defined as an orientation ratio of the carbonaceous material in the present invention.

Conditions for the X-ray diffraction measurement are as follows. "2θ" indicates an angle of diffraction.

Target: Cu (Kα-line) graphite monochromator
Slit:
   Divergence slit=0.5°
   Receiving slit=0.15 mm
   Scatter slit=0.5°
Measuring range and step angle/measuring time:
   (110) plane: 75°≤2θ≤80° 1°/60 seconds
   (004) plane: 52°≤2θ≤57° 1°/60 seconds (Aspect Ratio (Powder))

The aspect ratio of the carbonaceous material is generally 1 or more, and is generally 10 or less, preferably 8 or less, further preferably 5 or less. When the aspect ratio of the carbonaceous material is in the above range, the occurrence of a streak line is suppressed upon forming an electrode plate to enable further uniform application, so that excellent high current-density charge-discharge characteristics can be secured. The above-mentioned lower limit of the range is the theoretical lower limit of the aspect ratio of the carbonaceous material.

The aspect ratio is measured by observing the particles of carbonaceous material magnified by means of a scanning electron microscope. 50 arbitrary graphite particles fixed to the edge face of a metal having a thickness of 50 μm or less are selected, and individually three-dimensionally observed while rotating and slanting the stage having the sample fixed thereto, and diameter A, which is the largest diameter of the carbonaceous material particle, and diameter B, which is the shortest diameter perpendicular to diameter A, are measured and an average of the A/B values is determined. The aspect ratio (A/B) determined by the above measurement is defined as an aspect ratio of the carbonaceous material in the present invention.

(Rhombohedral Crystal Ratio)

The rhombohedral crystal ratio defined in the present invention can be determined using the formula below from a ratio of the rhombohedral crystal structure graphite layer (ABC stacking layer) to the hexagonal crystal structure graphite layer (AB stacking layer) as measured by wide-angle X-ray diffractometry (XRD).

Rhombohedral crystal ratio (%)=Integrated intensity of the ABC (101) XRD peak÷Integrated intensity of the AB (101) XRD peak×100

The rhombohedral crystal ratio is generally in the range of 0% or more, preferably more than 0%, more preferably 3% or more, further preferably 5% or more, especially preferably 12% or more, and is generally 35% or less, preferably 27% or less, further preferably 24% or less, especially preferably 20% or less. The rhombohedral crystal ratio of 0% indicates that any XRD peak ascribed to the ABC stacking layer is not detected. The rhombohedral crystal ratio of more than 0% indicates that an XRD peak ascribed to the ABC stacking layer is detected though it is slight.

When the rhombohedral crystal ratio is too large, there are a number of defects contained in the crystal structure of the negative electrode active material, and therefore the amount of the Li inserted is likely to be reduced, making it difficult to obtain high capacity. Further, the defects are likely to cause the electrolytic solution to be decomposed during the cycle, leading to deterioration of the cycle characteristics. In contrast, when the rhombohedral crystal ratio is in the range in the present invention, for example, an advantage is obtained in that there are few defects in the crystal structure of the negative electrode active material, and thus the reactivity of the negative electrode active material with the electrolytic solution is small, so that consumption of the electrolytic solution is low during the cycle, achieving excellent cycle characteristics.

An XRD measurement method for determining a rhombohedral crystal ratio is as follows.

A 0.2 mm sample plate is filled with a negative electrode active material powder so that the powder is not oriented, and is subjected to X-ray diffraction measurement by means of an X-ray diffraction apparatus (for example, X'Pert Pro MPD, manufactured by PANalytical B. V., using a Cu Kα-line at a power of 45 kV and at 40 mA). Using the obtained diffraction pattern, the above-mentioned peak integrated intensities are individually calculated using an analysis soft JADE 5.0 by profile fitting using the asymmetric Pearson VII function, and a rhombohedral crystal ratio is determined from the above formula.

Conditions for the X-ray diffraction measurement are as follows. "2θ" indicates an angle of diffraction.

Target: Cu (Kα-line) graphite monochromator
Slit:
  Solar slit: 0.04°
  Divergence slit: 0.5°
  Transverse divergence mask: 15 mm
  Scatter preventing slit: 1°
Measuring range and step angle/measuring time:
  (101) plane: 41°≤2θ≤47.5° 0.3°/60 seconds
Background correction: A straight line connecting points 42.7° and 45.5° is drawn and subtracted as a background.
Peak for the rhombohedral crystal structure graphite particle layer: which indicates a peak appearing at around 43.4°.
Peak for the hexagonal crystal structure graphite particle layer: which indicates a peak appearing at around 44.5°.

<Construction of and Preparation Method for a Negative Electrode>

In the production of an electrode, any known method can be used as long as the effects of the present invention are not markedly sacrificed. For example, the electrode can be formed by adding to the negative electrode active material a binder and a solvent, and, if necessary, for example, a thickening agent, a conductor, and a filler to obtain a slurry, and applying the obtained slurry to a current collector and drying the applied slurry, and then pressing the resultant material.

When an alloy material is used, a method of forming a thin film layer containing the above-mentioned negative electrode active material (negative electrode active material layer) by a method, such as a vapor deposition method, a sputtering method, or a plating method, is also used.

(Current Collector)

As a current collector having held thereon the negative electrode active material, a known current collector can be arbitrarily used. Examples of current collectors for the negative electrode include metal materials, such as aluminum, copper, nickel, stainless steel, and nickel-plated steel. From the viewpoint of ease of processing and the cost, copper is especially preferred.

With respect to the form of the current collector, when the current collector is a metal material, examples of forms include a metal foil, a metal cylinder, a metal coil, a metal plate, a metal thin film, an expanded metal, a punching metal, and a foamed metal. Of these, preferred is a metal thin film, more preferred is a copper foil, and further preferred are a rolled copper foil formed by a rolling method and an electrolytic copper foil formed by an electrolytic method, and any of them can be used as a current collector.

From the viewpoint of securing the battery capacity and the handling properties, the thickness of the current collector is generally 1 μm or more, preferably 5 μm or more, and is generally 100 μm or less, preferably 50 μm or less.

(Thickness Ratio of the Current Collector and the Negative Electrode Active Material Layer)

With respect to the thickness ratio of the current collector and the negative electrode active material layer, there is no particular limitation. However, a value of "(the thickness of the negative electrode active material layer on one side immediately before injecting the non-aqueous electrolytic solution)/(the thickness of the current collector)" is preferably 150 or less, further preferably 20 or less, especially preferably 10 or less, and is preferably 0.1 or more, further preferably 0.4 or more, especially preferably 1 or more. When the thickness ratio of the current collector and the negative electrode active material layer is in the above range, the battery capacity can be secured, and further heat generation of the current collector during the high current-density charging and discharging can be suppressed.

(Binder)

With respect to the binder for binding the negative electrode active material, there is no particular limitation as long as it is a stable material against the non-aqueous electrolytic solution and the solvent used when producing the electrode.

Specific examples of binders include resin polymers, such as polyethylene, polypropylene, polyethylene terephthalate, polymethyl methacrylate, aromatic polyamide, polyimide, cellulose, and nitrocellulose; rubber polymers, such as an SBR (styrene-butadiene rubber), an isoprene rubber, a butadiene rubber, a fluororubber, an NBR (acrylonitrile-butadiene rubber), and an ethylene-propylene rubber; a styrene-butadiene-styrene block copolymer and hydrogenation products thereof; thermoplastic elastomer polymers, such as an EPDM (ethylene-propylene-diene terpolymer), a styrene-ethylene-butadiene-styrene copolymer, a styrene-isoprene-styrene block copolymer, and hydrogenation products thereof; soft resin polymers, such as syndiotactic 1,2-polybutadiene, polyvinyl acetate, an ethylene-vinyl acetate copolymer, and a propylene-α-olefin copolymer; fluorine polymers, such as polyvinylidene fluoride, polytetrafluoroethylene, fluorinated polyvinylidene fluoride, and a polytetrafluoroethylene-ethylene copolymer; and a polymer composition having ion-conductive properties of alkali metal ions (particularly, lithium ions). These binders may be used individually, or two or more types of the binders may be used in an arbitrary combination and in an arbitrary ratio.

The proportion of the binder to the negative electrode active material is preferably 0.1% by mass or more, further preferably 0.5% by mass or more, especially preferably 0.6% by mass or more, and is preferably 20% by mass or less, more preferably 15% by mass or less, further preferably 10% by mass or less, especially preferably 8% by mass or less. When the proportion of the binder to the negative electrode active material is in the above range, the battery capacity and the strength of the negative electrode can be satisfactorily secured.

Particularly, when the binder contains a rubbery polymer, such as an SBR, as a main component, the proportion of the binder to the negative electrode active material is generally 0.1% by mass or more, preferably 0.5% by mass or more, further preferably 0.6% by mass or more, and is generally 5% by mass or less, preferably 3% by mass or less, further preferably 2% by mass or less. When the binder contains a fluorine polymer, such as polyvinylidene fluoride, as a main component, the proportion of the binder to the negative electrode active material is generally 1% by mass or more, preferably 2% by mass or more, further preferably 3% by mass or more, and is generally 15% by mass or less, preferably 10% by mass or less, further preferably 8% by mass or less.

(Solvent for Forming a Slurry)

With respect to the type of the solvent for forming a slurry, there is no particular limitation as long as it is a solvent capable of dissolving or dispersing therein the negative electrode active material, and binder, and thickening agent and conductor used if necessary, and any of an aqueous solvent and an organic solvent may be used.

Examples of aqueous solvents include water and alcohols, and examples of organic solvents include N-methylpyrrolidone (NMP), dimethylformamide, dimethylacetamide, methyl ethyl ketone, cyclohexanone, methyl acetate, methyl acrylate, diethyltriamine, N,N-dimethylaminopropylamine, tetrahydrofuran (THF), toluene, acetone, diethyl ether, dimethylacetamide, hexamethylphosphoramide, dimethyl sulfoxide, benzene, xylene, quinoline, pyridine, methylnaphthalene, and hexane.

Especially when an aqueous solvent is used, it is preferred that a slurry is formed using a thickening agent and a latex of, e.g., an SBR as well as, for example, a dispersant. These solvents may be used individually, or two or more types of the solvents may be used in an arbitrary combination and in an arbitrary ratio.

(Thickening Agent)

A thickening agent is generally used for controlling the viscosity of a slurry. With respect to the thickening agent, there is no particular limitation, but specific examples of thickening agents include carboxymethyl cellulose, methyl cellulose, hydroxymethyl cellulose, ethyl cellulose, polyvinyl alcohol, oxidized starch, starch phosphate, casein, and salts thereof. These thickening agents may be used individually, or two or more types of the thickening agents may be used in an arbitrary combination and in an arbitrary ratio.

When a thickening agent is further used, the proportion of the thickening agent to the negative electrode active material is generally 0.1% by mass or more, preferably 0.5% by mass or more, further preferably 0.6% by mass or more, and is generally 5% by mass or less, preferably 3% by mass or less, further preferably 2% by mass or less. When the proportion of the thickening agent to the negative electrode active material is in the above range, a lowering of the battery capacity and an increase of the resistance can be suppressed, and further excellent application properties can be secured.

(Electrode Density)

When an electrode is formed from the negative electrode active material, with respect to the resultant electrode structure, there is no particular limitation, but the density of the negative electrode active material present on the current collector is preferably 1 g·cm$^{-3}$ or more, further preferably 1.2 g·cm$^{-3}$ or more, especially preferably 1.3 g·cm$^{-3}$ or more, and is preferably 2.2 g·cm$^{-1}$ or less, more preferably 2.1 g·cm$^{-3}$ or less, further preferably 2.0 g·cm$^{-3}$ or less, especially preferably 1.9 g·cm$^{-3}$ or less. When the density of the negative electrode active material present on the current collector is in the above range, a damage of the negative electrode active material particles can be prevented, making it possible to suppress an increase of the initial irreversible capacity and deterioration of the high current-density charge/discharge characteristics due to a lowering of penetration of the non-aqueous electrolytic solution to near the current collector/negative electrode active material interface, and, meanwhile, a lowering of the battery capacity and an increase of the resistance can be suppressed.

(Thickness of the Negative Electrode Plate)

The thickness of the negative electrode plate is designed in accordance with the positive electrode plate, and is not particularly limited, but the thickness of the active material layer obtained by taking away the thickness of the metal foil as a core material is generally 15 μm or more, preferably 20 μm or more, more preferably 30 μm or more, and is generally 300 μm or less, preferably 280 μm or less, more preferably 250 μm or less.

(Surface Coating on the Negative Electrode Plate)

The above-mentioned negative electrode plate having deposited on the surface thereof a substance having a composition different from that of the negative electrode plate may be used. Examples of surface deposition substances include oxides, such as aluminum oxide, silicon oxide, titanium oxide, zirconium oxide, magnesium oxide, calcium oxide, boron oxide, antimony oxide, and bismuth oxide; sulfates, such as lithium sulfate, sodium sulfate, potassium sulfate, magnesium sulfate, calcium sulfate, and aluminum sulfate; and carbonates, such as lithium carbonate, calcium carbonate, and magnesium carbonate.

2-2. Positive Electrode

<Positive Electrode Active Material>

The positive electrode active material used in the positive electrode is described below.

(Composition)

With respect to the positive electrode active material, there is no particular limitation as long as it is capable of electrochemically having occluded therein and releasing lithium ions. However, the positive electrode active material is preferably, for example, a material containing lithium and at least one transition metal. Specific examples of such materials include a lithium-transition metal composite oxide and a lithium-containing transition metal phosphate compound.

As the transition metal for the lithium-transition metal composite oxide, for example, V, Ti, Cr, Mn, Fe, Co, Ni, and Cu are preferred, and specific examples of the oxides include lithium-cobalt composite oxides, such as $LiCoO_2$, lithium-nickel composite oxides, such as $LiNiO_2$, lithium-manganese composite oxides, such as $LiMnO_2$, $LiMn_2O_4$, and $Li_2MnO_4$, and these lithium-transition metal composite oxides in which part of the transition metal atoms mainly constituting the oxide are replaced by another element, such as Na, K, B, F, Al, Ti, V, Cr, Mn, Fe, Co, Li, Ni, Cu, Zn, Mg, Ga. Zr, Si, Nb, Mo, Sn, or W. Specific examples of the lithium-transition metal composite oxides having part of the transition metal atoms replaced by another element include $LiNi_{0.5}Mn_{0.5}O_2$, $LiNi_{0.85}Co_{0.10}Al_{0.05}O_2$, $LiNi_{0.33}Co_{0.33}Mn_{0.33}O_2$, $LiNi_{0.45}Co_{0.10}Al_{0.45}O_2$, $LiMn_{1.8}Al_{0.2}O_4$, and $LiMn_{1.5}Ni_{0.5}O_4$.

As the transition metal for the lithium-containing transition metal phosphate compound, for example, V, Ti, Cr, Mn, Fe, Co, Ni, and Cu are preferred, and specific examples of the compounds include iron phosphates, such as $LiFePO_4$, $Li_3Fe_2(PO_4)_3$, and $LiFeP_2O_7$, cobalt phosphates, such as $LiCoPO_4$, and these lithium transition metal phosphate compounds in which part of the transition metal atoms mainly constituting the compound are replaced by another element, such as Al, Ti, V, Cr, Mn, Fe, Co, Li, Ni, Cu, Zn, Mg, Ga, Zr, Nb, or Si.

Further, the positive electrode active material preferably contains lithium phosphate because the continuous charging characteristics are improved. With respect to the use of lithium phosphate, there is no particular limitation, but it is preferred that the above-mentioned positive electrode active material and lithium phosphate are mixed together and used. With respect to the amount of the lithium phosphate used, the lower limit is preferably 0.1% by mass or more, more preferably 0.3% by mass or more, further preferably 0.5% by mass or more, and the upper limit is preferably 10% by mass or less, more preferably 8% by mass or less, further preferably 5% by mass or less, based on the total mass of the positive electrode active material and lithium phosphate.

(Surface Coating)

The above-mentioned positive electrode active material having deposited on the surface thereof a substance having a composition different from that of the positive electrode active material may be used. Examples of surface deposition substances include oxides, such as aluminum oxide, silicon oxide, titanium oxide, zirconium oxide, magnesium oxide, calcium oxide, boron oxide, antimony oxide, and bismuth oxide; sulfates, such as lithium sulfate, sodium sulfate, potassium sulfate, magnesium sulfate, calcium sulfate, and aluminum sulfate; carbonates, such as lithium carbonate, calcium carbonate, and magnesium carbonate; and carbon.

The surface deposition substance can be deposited on the surface of the positive electrode active material by, for example, a method in which a surface deposition substance is dissolved or suspended in a solvent and the positive electrode active material is impregnated with the resultant solution or suspension, followed by drying, a method in which a surface deposition substance precursor is dissolved or suspended in a solvent and the positive electrode active material is impregnated with the resultant solution or suspension, followed by a reaction caused by, e.g., heating, or a method in which a surface deposition substance is added to a positive electrode active material precursor whereupon the resultant mixture is calcined. When carbon is deposited, a method can be used in which a carbonaceous material, for example, in the form of activated carbon is mechanically deposited later.

With respect to the amount of the surface deposition substance, the lower limit is preferably 0.1 ppm or more, more preferably 1 ppm or more, further preferably 10 ppm or more, and the upper limit is preferably 20% or less, more preferably 10% or less, further preferably 5% or less, based on the mass of the positive electrode active material. The surface deposition substance can prevent the electrolytic solution from suffering an oxidation reaction on the surface of the positive electrode active material, improving the battery life. However, when the amount of the substance deposited is too small, the above effect is not satisfactorily exhibited, and, when the amount of the substance deposited is too large, the substance is likely to inhibit lithium ions from going into or out of the active material, increasing the resistance.

In the present invention, the positive electrode active material having deposited on the surface thereof a substance having a composition different from that of the positive electrode active material is also called a "positive electrode active material".

(Shape)

Examples of shapes of the particles of the positive electrode active material include a bulk shape, a polyhedral shape, a spherical shape, an ellipsoidal shape, a plate shape, a needle-like shape, and a cylindrical shape that are conventionally used. The primary particles of the positive electrode active material may undergo aggregation to form secondary particles.

(Tap Density)

The tap density of the positive electrode active material is preferably 0.5 g/cm$^3$ or more, more preferably 0.8 g/cm$^3$ or more, further preferably 1.0 g/cm$^3$ or more. When the tap density of the positive electrode active material is in the above range, the amount of the dispersing medium required and the amount of the conductor or binder required for forming the positive electrode active material layer can be reduced, so that the filling ratio of the positive electrode active material and the battery capacity can be secured. By using a composite oxide powder having a high tap density, a positive electrode active material layer having high density can be formed. Generally, the tap density is preferably larger, and does not particularly have the upper limit, but is preferably 4.0 g/cm$^3$ or less, more preferably 3.7 g/cm$^3$ or less, further preferably 3.5 g/cm$^3$ or less. When the tap density of the positive electrode active material is in the above range, deterioration of the load characteristics can be suppressed.

In the present invention, the tap density is determined by placing 5 to 10 g of a positive electrode active material powder in a 10-ml glass measuring cylinder and subjecting the powder to 200-time tapping with a stroke of about 20 mm to measure a powder filling density (tap density) g/cc.

(Median Diameter d50)

The median diameter d50 of the particles of the positive electrode active material (secondary particle diameter when the primary particles of the positive electrode active material undergo aggregation to form secondary particles) is preferably 0.3 µm or more, more preferably 0.5 µm or more, further preferably 0.8 µm or more, most preferably 1.0 µm or more, and the upper limit of the median diameter is preferably 30 µm or less, more preferably 27 µm or less, further preferably 25 µm or less, most preferably 22 µm or less. When the median diameter is in the above range, particles having high tap density can be obtained and deterioration of the battery performance can be suppressed and, meanwhile, when a positive electrode for battery is prepared, that is, an active material, a conductor, a binder, and others are mixed into a solvent and the resultant slurry is applied to form a thin film, problems of the occurrence of a streak line and the like can be prevented. When two types or more of the positive electrode active materials having different median diameters d50 are mixed, the filling properties upon preparing a positive electrode can be further improved.

In the present invention, the median diameter d50 is measured by a known laser diffraction/scattering-type particle size distribution measurement apparatus. When LA-920, manufactured by HORIBA, Ltd., is used as a particle size distribution meter, ultrasonic dispersion is performed for 5 minutes using a 0.1% by mass aqueous solution of sodium hexametaphosphate as a dispersing medium for the measurement, and then the refractive index measured is set at 1.24, and the measurement is conducted.

(Average Primary Particle Diameter)

When the primary particles of the positive electrode active material undergo aggregation to form secondary particles, the average primary particle diameter of the positive electrode active material is preferably 0.05 µm or more, more preferably 0.1 µm or more, further preferably 0.2 µm or more, and the upper limit of the average primary particle diameter is preferably 5 µm or less, more preferably 4 µm or less, further preferably 3 µm or less, most preferably 2 µm or less. When the average primary particle diameter of the positive electrode active material is in the above range, the powder filling properties and specific surface area can be secured to suppress deterioration of the battery performance and, meanwhile, appropriate crystalline properties can be obtained, so that the reversibility for charging and discharging can be secured.

In the present invention, the primary particle diameter is measured by observation using a scanning electron microscope (SEM). Specifically, in a photomicrograph taken at a magnification of 10,000 times, with respect to 50 arbitrary primary particles, a value of the longest section of a horizontal line defined by the boundaries of the primary particle on the both sides is determined, and an average of the obtained values is determined as a primary particle diameter.

(BET Specific Surface Area)

The BET specific surface area of the positive electrode active material is preferably 0.1 m$^2$/g or more, more preferably 0.2 m$^2$/g or more, further preferably 0.3 m$^2$/g or more, and the upper limit is 50 m²/g or less, preferably 40 m²/g or less, further preferably 30 m²/g or less. When the BET specific surface area of the positive electrode active material is in the above range, the battery performance can be secured, and further excellent application properties of the positive electrode active material can be maintained.

In the present invention, the BET specific surface area is defined by a value which is measured using a surface area meter (for example, Fully-automatic surface area measurement apparatus, manufactured by Ohkura Riken Inc.) by subjecting a sample to predrying under a nitrogen gas flow at 150° C. for 30 minutes, and then making a measurement in accordance with a nitrogen adsorption BET single-point method by a gas flow method using a nitrogen-helium mixed gas accurately prepared so that the nitrogen pressure relative to atmospheric pressure becomes 0.3.

(Method for Producing the Positive Electrode Active Material)

As a method for producing the positive electrode active material, a method customarily employed as a method for producing an inorganic compound is used. Particularly, as a method for producing an active material of a spherical shape or an ellipsoidal shape, various methods can be considered, and, for example, there can be mentioned a method in which a transition metal raw material is dissolved or pulverized and dispersed in a solvent, such as water, and the pH of the resultant solution or dispersion is controlled while stirring to form a spherical precursor, and the formed spherical precursor is recovered, and dried if necessary, and then a Li source, such as LiOH, $Li_2CO_3$, or $LiNO_3$, is added to the precursor, followed by calcination at a high temperature, to obtain an active material.

In the production of a positive electrode, the above-mentioned positive electrode active materials may be individually used, or the positive electrode active material and the other one or more positive electrode active materials having a composition different from that of the above positive electrode active material may be used in an arbitrary combination and in an arbitrary ratio. In this case, examples of preferred combinations include a combination of $LiCoO_2$ and $LiMn_2O_4$ or the $LiMn_2O_4$ having part of Mn replaced by, e.g., the other transition metal, such as $LiNi_{0.33}Co_{0.33}Mn_{0.33}O_2$, and a combination with $LiCoO_2$ or the $LiCoO_2$ having part of Co replaced by, e.g., the other transition metal.

<Construction of and Preparation Method for a Positive Electrode>

The construction of a positive electrode is described below. In the present invention, the positive electrode can be prepared by forming a positive electrode active material layer containing the positive electrode active material and a binder on a current collector. Production of the positive electrode using the positive electrode active material can be performed by a general method. Specifically, the positive electrode can be obtained by mixing together the positive electrode active material and a binder, and, if necessary, for example, a conductor and a thickening agent by a dry process and forming the resultant mixture into a sheet form, and bonding the sheet onto a current collector for positive electrode by pressing, or by dissolving or dispersing the above materials in a liquid medium to form a slurry, and applying the slurry to a current collector for positive electrode, and drying the applied slurry to form a positive electrode active material layer on a current collector.

The content of the positive electrode active material in the positive electrode active material layer is preferably 80% by mass or more, more preferably 82% by mass or more, especially preferably 84% by mass or more, and is preferably 99% by mass or less, more preferably 98% by mass or less. When the content of the positive electrode active material is in the above range, the electric capacity of the positive electrode active material in the positive electrode active material layer can be secured, and further the strength of the positive electrode can be maintained.

For increasing the filling density of the positive electrode active material, the positive electrode active material layer obtained after the application and drying is preferably pressed and increased in density by means of, for example, a handpress or a roller press. With respect to the density of the positive electrode active material layer, the lower limit is preferably 1.5 g/cm³ or more, more preferably 2 g/cm³, further preferably 2.2 g/cm³ or more, and the density is preferably in the range of 5 g/cm³ or less, more preferably 4.5 g/cm³ or less, further preferably 4 g/cm³ or less. When the density of the positive electrode active material layer is in the above range, excellent charge/discharge characteristics can be obtained, and further an increase of the electric resistance can be suppressed.

(Conductor)

As the conductor, a known conductor can be arbitrarily used. Specific examples of conductors include metal materials, such as copper and nickel; graphite, such as natural graphite and artificial graphite; carbon black, such as acetylene black; and carbon materials, e.g., amorphous carbon, such as needle coke. These conductors may be used individually, or two or more types of the conductors may be used in an arbitrary combination and in an arbitrary ratio. The conductor is used in such an amount that the amount of the conductor contained in the positive electrode active material layer is generally 0.01% by mass or more, preferably 0.1% by mass or more, more preferably 1% by mass or more, and the upper limit of the amount of the conductor is generally 50% by mass or less, preferably 30% by mass or less, more preferably 15% by mass or less. When the amount of the conductor is in the above range, satisfactory conductive properties and battery capacity can be secured.

(Binder)

With respect to the binder used in producing the positive electrode active material layer, there is no particular limitation, and, in the case of application method, the binder may be a material which can be dissolved or dispersed in the liquid medium used in producing the electrode, and specific examples of binders include resin polymers, such as polyethylene, polypropylene, polyethylene terephthalate, polymethyl methacrylate, polyimide, aromatic polyamide, cellulose, and nitrocellulose; rubber polymers, such as an SBR (styrene-butadiene rubber), an NBR (acrylonitrile-butadiene rubber), a fluororubber, an isoprene rubber, a butadiene rubber, and an ethylene-propylene rubber; thermoplastic elastomer polymers, such as a styrene-butadiene-styrene block copolymer and hydrogenation products thereof, an EPDM (ethylene-propylene-diene terpolymer), a styrene-ethylene-butadiene-ethylene copolymer, a styrene-isoprene-styrene block copolymer, and hydrogenation products thereof; soft resin polymers, such as syndiotactic 1,2-polybutadiene, polyvinyl acetate, an ethylene-vinyl acetate copolymer, and a propylene-α-olefin copolymer; fluorine polymers, such as polyvinylidene fluoride (PVdF), polytetrafluoroethylene, fluorinated polyvinylidene fluoride, and a polytetrafluoroethylene-ethylene copolymer; and a polymer composition having ion-conductive properties of alkali metal ions (particularly, lithium ions). These substances may be used individually, or two or more types of the substances may be used in an arbitrary combination and in an arbitrary ratio.

The proportion of the binder to the positive electrode active material layer is generally 0.1% by mass or more, preferably 1% by mass or more, further preferably 1.5% by mass or more, and the upper limit of the proportion of the binder is generally 80% by mass or less, preferably 60% by mass or less, further preferably 40% by mass or less, most preferably 10% by mass or less. When the proportion of the binder is too low, it is likely that the positive electrode active material cannot be satisfactorily held so that the resultant positive electrode is unsatisfactory in the mechanical strength, leading to deterioration of battery performance, such as cycle characteristics. On the other hand, when the proportion of the binder is too high, the battery capacity and conductive properties are likely to be lowered.

(Solvent for Forming a Slurry)

With respect to the type of the solvent for forming a slurry, there is no particular limitation as long as it is a solvent capable of dissolving or dispersing therein the positive electrode active material, conductor, and binder, and thickening agent used if necessary, and any of an aqueous solvent and an organic solvent may be used. Examples of aqueous media include water, and a mixed medium of an alcohol and water. Examples of organic media include aliphatic hydrocarbons, such as hexane; aromatic hydrocarbons, such as benzene, toluene, xylene, and methylnaphthalene; heterocyclic compounds, such as quinoline and pyridine; ketones, such as acetone, methyl ethyl ketone, and cyclohexanone; esters, such as methyl acetate and methyl acrylate; amines, such as diethylenetriamine and N,N-dimethylaminopropylamine; ethers, such as diethyl ether, propylene oxide, and tetrahydrofuran (THF); amides, such as N-methylpyrrolidone (NMP), dimethylformamide, and dimethylacetamide; and aprotic polar solvents, such as hexamethylphosphoramide and dimethyl sulfoxide.

Especially when an aqueous medium is used, it is preferred that a slurry is formed using a thickening agent and a latex of, e.g., a styrene-butadiene rubber (SBR). The thickening agent is generally used for controlling the viscosity of a slurry. With respect to the thickening agent, there is no particular limitation, but specific examples of thickening agents include carboxymethyl cellulose, methyl cellulose, hydroxymethyl cellulose, ethyl cellulose, polyvinyl alcohol, oxidized starch, starch phosphate, casein, and salts thereof. These thickening agents may be used individually, or two or more types of the thickening agents may be used in an arbitrary combination and in an arbitrary ratio. When a thickening agent is further added, the proportion of the thickening agent to the active material is in the range of 0.1% by mass or more, preferably 0.2% by mass or more, more preferably 0.3% by mass or more, and the upper limit of the proportion is 5% by mass or less, preferably 3% by mass or less, more preferably 2% by mass or less. When the proportion of the thickening agent is in the above range, excellent application properties can be obtained, and further a lowering of the battery capacity and an increase of the resistance can be suppressed.

(Current Collector)

With respect to the material for the positive electrode current collector, there is no particular limitation, and a known material can be arbitrarily used. Specific examples of materials for the current collector include metal materials, such as aluminum, stainless steel, nickel plating, titanium, and tantalum, and carbon materials, such as carbon cloth and carbon paper. Of these, metal materials are preferred, and especially preferred is aluminum.

With respect to the form of the current collector, in the case of a metal material, examples of forms include a metal foil, a metal cylinder, a metal coil, a metal plate, a metal thin film, an expanded metal, a punching metal, and a foamed metal, and, in the case of a carbon material, examples of forms include a carbon plate, a carbon thin film, and a carbon cylinder. Of these, a metal thin film is preferred. The thin film may be appropriately formed into a mesh form. The thickness of the thin film is arbitrary, but, from the viewpoint of the strength and handling properties of the current collector, the thickness of the thin film is generally 1 μm or more, preferably 3 μm or more, more preferably 5 μm or more, and the upper limit of the thickness is generally 1 mm or less, preferably 100 μm or less, more preferably 50 μm or less.

It is preferred that a conductive auxiliary is applied to the surface of the current collector from the viewpoint of reducing the electronic contact resistance between the current collector and the positive electrode active material layer. Examples of conductive auxiliaries include carbon, and noble metals, such as gold, platinum, and silver.

With respect to the thickness ratio of the current collector and the positive electrode active material layer, there is no particular limitation. However, a value of (the thickness of the positive electrode active material layer on one side immediately before injecting the electrolytic solution)/(the thickness of the current collector) is preferably in the range of 20 or less, more preferably 15 or less, most preferably 10 or less, and the lower limit of the thickness ratio is preferably 0.5 or more, more preferably 0.8 or more, most preferably 1 or more. When the thickness ratio is larger than the above range, the current collector may cause heat generation due to Joulean heat during the high current-density charging and discharging. When the thickness ratio is in the above range, heat generation of the current collector during the high current-density charging and discharging can be suppressed, and the battery capacity can be secured.

(Electrode Area)

When the non-aqueous electrolytic solution of the present invention is used, from the viewpoint of improving the stability at high output and at high temperatures, it is preferred that the area of the positive electrode active material layer is large, relative to the outer surface area of a battery outer casing. Specifically, the total electrode area of the positive electrode is preferably 15 times or more, more preferably 40 times or more (area ratio) the outer surface area of the secondary battery. The outer surface area of the outer casing in the case of a closed-end rectangular shape means the total area determined by calculation from the sizes of the vertical and horizontal thicknesses of the casing portion filled with electricity generating elements, excluding the protruding portion of the terminal. The outer surface area of the outer casing in the case of a closed-end cylindrical shape means a geometric surface area of a cylinder determined when the casing portion filled with electricity generating elements, excluding the protruding portion of the terminal, is presumed to approximate to the cylinder. The total electrode area of the positive electrode means a geometric surface area of the positive electrode active material layer opposite to the active material layer containing the negative electrode active material, and, in the structure having on both sides the positive electrode active material layers through a current collector foil, the total electrode area of the positive electrode means the total of areas individually calculated for the respective sides.

(Thickness of the Positive Electrode Plate)

With respect to the thickness of the positive electrode plate, there is no particular limitation. However, from the viewpoint of the high capacity and high output, the lower limit of the thickness of the active material layer obtained by taking away the thickness of the metal foil as a core material, per one side of the current collector, is preferably 10 µm or more, more preferably 20 µm or more, and the upper limit of the thickness is preferably 500 µm or less, more preferably 450 µm or less.

(Surface Coating on the Positive Electrode Plate)

The above-mentioned positive electrode plate having deposited on the surface thereof a substance having a composition different from that of the positive electrode plate may be used. Examples of surface deposition substances include oxides, such as aluminum oxide, silicon oxide, titanium oxide, zirconium oxide, magnesium oxide, calcium oxide, boron oxide, antimony oxide, and bismuth oxide; sulfates, such as lithium sulfate, sodium sulfate, potassium sulfate, magnesium sulfate, calcium sulfate, and aluminum sulfate; carbonates, such as lithium carbonate, calcium carbonate, and magnesium carbonate; and carbon.

2-3. Separator

For preventing the occurrence of short-circuiting, generally, a separator is disposed between the positive electrode and the negative electrode. In this case, the separator is generally impregnated with the non-aqueous electrolytic solution of the present invention.

With respect to the material for and the form of the separator, there is no particular limitation, and a separator of a known material or form can be arbitrarily employed as long as the effects of the present invention are not markedly sacrificed. Especially, a separator formed from a material stable to the non-aqueous electrolytic solution of the present invention, such as a resin, a glass fiber, or an inorganic material, is used, and a separator in the form of a porous sheet or nonwoven fabric having excellent liquid retaining property is preferably used.

As a material for a resin or glass fiber separator, for example, a polyolefin, such as polyethylene or polypropylene, aromatic polyamide, polytetrafluoroethylene, polyether sulfone, or a glass filter can be used. Of these, preferred are a glass filter and a polyolefin, and further preferred is a polyolefin. These materials may be used individually, or two or more types of the materials may be used in an arbitrary combination and in an arbitrary ratio.

The thickness of the separator is arbitrary, but is generally 1 µm or more, preferably 5 µm or more, further preferably 8 µm or more, and is generally 50 µm or less, preferably 40 µm or less, further preferably 30 µm or less. When the thickness of the separator is in the above range, the insulation properties and mechanical strength can be secured, and further battery performance, such as rate characteristics, and the energy density can be secured.

Further, when a porous material, such as a porous sheet or nonwoven fabric, is used as a separator, the porosity of the separator is arbitrary, but is generally 20% or more, preferably 35% or more, further preferably 45% or more, and is generally 90%, or less, preferably 85% or less, further preferably 75% or less. When the porosity of the separator is in the above range, the insulation properties and mechanical strength can be secured, and further the film resistance can be suppressed to obtain excellent rate characteristics.

The average pore diameter of the separator is arbitrary, but is generally 0.5 µm or less, preferably 0.2 µm or less, and is generally 0.05 µm or more. When the average pore diameter of the separator is larger than the above range, short-circuiting is likely to occur. When the average pore diameter of the separator is in the above range, the occurrence of short-circuiting can be prevented, and the film resistance can be suppressed to obtain excellent rate characteristics. On the other hand, as an inorganic material, for example, an oxide, such as alumina or silicon dioxide, a nitride, such as aluminum nitride or silicon nitride, or a sulfate, such as barium sulfate or calcium sulfate, is used, and an inorganic material which is in a particle form or in a fiber form is used.

With respect to the form of the separator, a separator in the form of a thin film, such as nonwoven fabric, woven fabric, or a microporous film, is used. In the separator in the form of a thin film, one having a pore diameter of 0.01 to 1 µm and a thickness of 5 to 50 µm is preferably used. As a separator other than the separator in the form of the above-mentioned independent thin film, there can be used a separator having a composite porous layer containing particles of the above-mentioned inorganic material formed on the surface layer of the positive electrode and/or negative electrode using a binder made of a resin. For example, there can be mentioned a separator having on both sides of the positive electrode porous layers formed from alumina particles having a 90% particle diameter of less than 1 µm using a fluororesin as a binder.

2-4. Design of the Battery

<Electrode Group>

The electrode group may have any of a stacked structure in which the above-mentioned positive electrode plate and negative electrode plate are stacked through the above-mentioned separator, and a structure in which the above positive electrode plate and negative electrode plate have the above separator disposed therebetween and are spirally wound. The proportion of the volume of the electrode group to the internal volume of the battery (hereinafter, referred to as "electrode group occupancy") is generally 40% or more, preferably 50% or more, and is generally 90% or less, preferably 80% or less. When the electrode group occupancy is in the above range, the battery capacity can be secured, and the deterioration of characteristics caused due to an increase of the internal pressure, such as charging/discharging repeating performance or high-temperature storage properties, is suppressed, and further the operation of a gas valve can be prevented.

<Current Collection Structure>

With respect to the current collection structure, there is no particular limitation. However, for more effectively achieving the improvement of the high current-density charge-discharge characteristics by the non-aqueous electrolytic solution of the present invention, it is preferred to employ a structure such that the resistance of a wiring portion or joint portion is reduced. When the internal resistance is reduced as mentioned above, the effects obtained using the non-aqueous electrolytic solution of the present invention are especially advantageously exhibited.

In the electrode group of the above-mentioned stacked structure, a structure formed by binding together metal core portions of the individual electrode layers and welding the bound core portions to the terminal is advantageously used. When the area of a single electrode is increased, the internal resistance is increased, and therefore a method of forming a plurality of terminals in the electrode to reduce the resistance is also advantageously used. In the electrode group of the above-mentioned spirally wound structure, the internal resistance can be reduced by forming a plurality of lead structures in each of the positive electrode and the negative electrode and binding them together with the terminal.

<Outer Casing>

With respect to the material for the outer casing, there is no particular limitation as long as it is a material stable to the non-aqueous electrolytic solution used. Specifically, a metal, such as a nickel-plated steel plate, stainless steel, aluminum, an aluminum alloy, or a magnesium alloy, or a stacked film of a resin and an aluminum foil (laminate film) is used. From the viewpoint of the weight reduction, a metal, such as aluminum or an aluminum alloy, or a laminate film is preferably used.

Examples of the outer casings using a metal include those having a sealed structure obtained by welding the metals together by laser welding, resistance welding, or ultrasonic welding, and those having a calked structure obtained by caulking the above metals through a gasket made of a resin. Examples of the outer casings using the above-mentioned laminate film include those having a sealed structure obtained by heat-fusing the resin layers together. For improving the sealing properties, a resin different from the resin used in the laminate film may be disposed between the above resin layers. Particularly, when the resin layers are heat-fused through a current collection terminal to form a closed structure, bonding of a metal and a resin is made, and therefore, as a resin present between the metals, a resin having a polar group or a modified resin having introduced a polar group is preferably used. Further, the shape of the outer casing is arbitrary and, for example, any of a cylinder shape, a rectangle shape, a laminate shape, a coin shape, and a large-size type may be used.

<Protective Device>

As a protective device, for example, a PTC (positive temperature coefficient) which is increased in the resistance when abnormal heat generation occurs or too large a current flows, a temperature fuse, a thermistor, or a valve which cuts out the current flowing the circuit due to a rapid increase of the pressure or temperature in the battery upon abnormal heat generation (current cut-out valve) can be used. With respect to the above-mentioned protective device, one having conditions in which the device does not operate in the general use at a high current is preferably selected, and a design is more preferably employed such that abnormal heat generation or heat runaway is not caused without a protective device.

EXAMPLES

Hereinblow, the present invention will be described in more detail with reference to the following Examples and Reference Examples, which should not be construed as limiting the scope of the present invention.

[Preparation of a Secondary Battery]
<Preparation of a Positive Electrode>

90 Parts by mass of nickel-manganese-lithium cobalt oxide ($LiNi_{1/3}Mn_{1/3}Co_{1/3}O_2$) as a positive electrode active material, 7 parts by mass of carbon black, and 3 parts by mass of polyvinylidene fluoride were mixed together, and N-methyl-2-pyrrolidone was added to the resultant mixture to obtain a slurry, and the obtained slurry was uniformly applied to both sides of an aluminum foil having a thickness of 15 μm so that the coating weight became 11.85 mg·cm$^{-2}$, and dried and then, the resultant material was pressed so that the positive electrode active material layers had a density of 2.6 g·cm$^{-3}$ to obtain a positive electrode.

<Preparation of a Negative Electrode>

To graphite were added an aqueous dispersion of sodium carboxymethyl cellulose (sodium carboxymethyl cellulose concentration: 1% by mass) as a thickening agent and an aqueous dispersion of a styrene-butadiene rubber (styrene-butadiene rubber concentration: 50%, by mass) as a binder, and the resultant mixture was mixed using a disperser to obtain a slurry. The obtained slurry was uniformly applied to one side of a copper foil having a thickness of 12 μm so that the coating weight became 6.0 mg·cm$^{-2}$, and dried and then, the resultant material was pressed so that the negative electrode active material layer had a density of 1.36 g·cm$^{-3}$ to obtain a negative electrode. The graphite used had a d50 of 10.9 μm, a specific surface area of 3.41 m$^2$/g, and a tap density of 0.985 g/cm$^3$. The slurry was prepared so that the [graphite:sodium carboxymethyl cellulose:styrene-butadiene rubber] mass ratio in the negative electrode after being dried became 97.5:1.5:1.

<Production of a Non-Aqueous Electrolyte Secondary Battery>

The above-prepared positive electrode and negative electrode and a separator were stacked in the order of the negative electrode, separator, and positive electrode. A separator made of polypropylene having a thickness of 20 μm and a porosity of 54% was used. The thus obtained battery element was wrapped in an aluminum laminate film in a cylindrical form, and the below-mentioned electrolytic solution was injected into the wrapped element, followed by vacuum sealing, to produce a non-aqueous electrolyte secondary battery in a sheet form. Further, for increasing the adhesion between the electrodes, the sheet-form battery was sandwiched between glass plates and a pressure was applied to the battery.

[Evaluation of a Battery]
<Initial Charge/Discharge Test>

In a thermostatic chamber at 25° C., the sheet-form non-aqueous electrolyte secondary battery was charged at 0.05 C for 10 hours, and then allowed to rest for 3 hours, and subsequently the battery was subjected to constant-current charging at 0.2 C until the voltage became 4.1 V. After allowed to rest for another 3 hours, with respect to the resultant battery, constant-current constant-voltage charging at 0.2 C was performed until the voltage became 4.1 V, and then constant-current discharging at ⅓C was performed until the voltage became 3.0 V. Subsequently, a series of constant-current constant-voltage charging at ⅓C performed until the voltage became 4.1 V and the subsequent constant-current discharging at ⅓C performed until the voltage became 3.0 V was taken as one charge-discharge cycle and the charge-discharge cycle was repeated twice (2 cycles). Further, constant-current constant-voltage charging at ⅓C was performed until the voltage became 4.1 V, and then the battery was stored at 60° C. for 12 hours so that the battery was stabilized. Subsequently, a charge-discharge cycle of constant-current constant-voltage charging at ⅓C performed at 25° C. until the voltage became 4.2 V and the subsequent constant-current discharging at ⅓C performed until the voltage became 3.0 V was repeated twice (2 cycles). The discharge capacity after the last cycle was taken as an initial capacity. 1 C indicates a current at which discharging of the whole capacity of the battery is completed in 1 hour.

<Test for Evaluation of the Cycle Capacity Maintaining Ratio>

With respect to the battery which had been subjected to initial charging/discharging, a charge-discharge cycle of charging by a constant-current method at 2 C performed at 60° C. until the voltage became 4.2 V and discharging by a constant-current method at 2 C performed until the voltage became 3.0 V was repeated 100 times (100 cycles). Then, a charge-discharge cycle of constant-current constant-voltage charging at ⅓C performed at 25° C. until the voltage became 4.2 V and the subsequent constant-current discharging at ⅓C performed until the voltage became 3.0 V was repeated three times (3 cycles). The discharge capacity after the last cycle was taken as an after-cycle capacity, and a percentage of the after-cycle capacity to the initial capacity was taken as a cycle capacity maintaining ratio (%).

<High-Temperature Storage Test>

With respect to the battery which had been subjected to initial charging/discharging, constant-current constant-voltage charging at ⅓C was performed until the voltage became 4.2 V, and the resultant battery was allowed to stand at 60° C. for one week. Then, a charge-discharge cycle of constant-current constant-voltage charging at ⅓C performed at 25° C. until the voltage became 4.2 V and the subsequent constant-current discharging at ⅓C performed until the voltage became 3.0 V was repeated three times (3 cycles). The discharge capacity after the last cycle was taken as an after-high-temperature-storage capacity, and a percentage of the after-high-temperature-storage capacity to the initial capacity was taken as a high-temperature storage capacity maintaining ratio (%).

<Test for Evaluation of the Low-Temperature Resistance Characteristics>

The initial and after-cycle batteries are adjusted to 3.72 V, and the batteries in this state are subjected to constant-current discharging at −30° C. for 10 seconds using various current values. Voltages obtained after 10 seconds are plotted with respect to the various current values, and a current value at which the voltage after 10 seconds becomes 3 V is determined. The slope of a straight line obtained by connecting a point of the thus determined current value and a point of the initial value (open circuit state) was defined as low-temperature resistance characteristics (Ω).

[Synthesis of Compounds]

Synthesis Example 1: Synthesis of a Compound of Formula (A)

[Chemical formula 50]

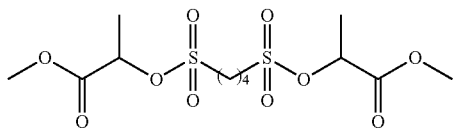

(A)

4.28 g (41 mmol) of methyl L-lactate was weighed and placed in a 50 ml three-neck flask, and 10 ml of methyl ethyl ketone (MEK) was added thereto to obtain a uniform solution. The flask containing the solution was immersed in an ice bath, and the solution was cooled to 3° C., and then 4.16 g (41 mmol) of triethylamine was added to the solution. A solution of 5.0 g (20 mmol) of 1,4-butanedisulfonyl chloride in 13 ml of MEK was dropwise added to the resultant mixture using a dropping funnel over about 1.5 hours so that the internal temperature did not exceed 10° C. After completion of the addition, the resultant mixture was stirred at an internal temperature of 5° C. for 2 hours, and then the reaction solution was subjected to filtration. The resultant filtrate was concentrated until the volatile components disappeared to obtain a pale yellow oil. The obtained oil was dissolved in 40 ml of methanol and, while cooling using a dry ice/ethanol bath, the resultant solution was stirred at an internal temperature of −20° C. for 30 minutes. An intended product was deposited in the form of a white powder. The deposited product was collected by filtration by means of suction, and washed with methanol, and then subjected to vacuum drying using a vacuum pump (at 25° C. for 12 hours) to obtain 4.87 g of an intended disulfonic ester (yield: 63.6%). The purity estimated from a GC analysis was 99.3%.

¹H-NMR (CDCl₃, 400 MHz): δ5.15 (q, J=7, 2H), 3.81 (s, 6H), 3.38-3.25 (m, 4H), 2.13-2.10 (m, 4H), 1.62 (d, J=7, 6H). MS (DCI): m/z 391 (M+H)⁺.

Synthesis Example 2: Synthesis of a Compound of Formula (B)

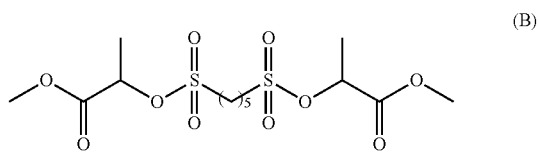

(B)

Into a 100 ml three-neck flask were charged 1.79 g (17.2 mmol) of methyl L-lactate, 2.10 g (7.8 mmol) of 1,5-pentanedisulfonyl chloride, and 20 ml of tetrahydrofuran (THF) to obtain a uniform solution. Then, the solution was cooled using an ice bath until the internal temperature became 2° C. A solution of 1.92 g (18.9 mmol) of triethylamine in THF (5 ml) was dropwise added using a dropping funnel to the solution in the flask under a nitrogen gas flow at an internal temperature of 2 to 5° C. After completion of the addition, the resultant mixture was stirred for 2 hours while cooling using an ice bath, and water was poured into the mixture, and then the mixture was extracted with ethyl acetate, and the resultant organic layer was dried over anhydrous magnesium sulfate, and then concentrated to obtain an oily material. 5 ml of methanol was added to the oily material, and stirred at an internal temperature of −20° C. for 30 minutes while cooling using a dry ice/ethanol bath. The deposited white powder was collected by filtration and subjected to vacuum drying (at 40° C. for 5 hours) to obtain 1.8 g (4.4 mmol) of an intended disulfonic ester (yield: 57%). The purity estimated from a GC analysis was 99.8%.

¹H-NMR (CDCl₃, 400 MHz): δ5.14 (q, J=8, 2H), 3.81 (s, 6H), 3.33-3.18 (m, 4H), 2.03-1.92 (m, 4H), 1.61-1.58 (m, 2H), 1.62 (d, J=8, 6H). MS (DCI): m/z 405 (M+H)⁺.

Synthesis Example 3: Synthesis of a Compound of Formula (C)

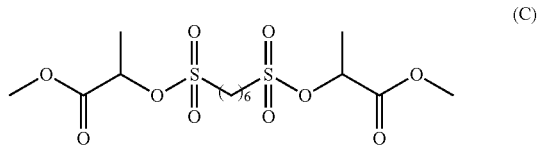

(C)

Into a 100 ml three-neck flask were charged 2.03 g (19.5 mmol) of methyl L-lactate, 2.50 g (8.8 mmol) of 1,6-hexanebis(sulfonyl chloride), and 20 ml of THF to obtain a uniform solution. Then, the solution was cooled using an ice bath until the internal temperature became 2° C. A solution of 2.23 g (22.0 mmol) of triethylamine in THF (5 ml) was dropwise added using a dropping funnel to the solution in the flask under a nitrogen gas flow at an internal temperature of 2 to 5° C. After completion of the addition, the resultant mixture was stirred for 2 hours while cooling using an ice bath, and water was poured into the mixture, and then the mixture was extracted with ethyl acetate, and the resultant organic layer was dried over anhydrous magnesium sulfate and then concentrated. 5 ml of methanol was added to the resultant oily crude product, and stirred at an internal temperature of −20° C. while cooling using a dry ice/ethanol bath, but solidification did not occur. The mixture was subjected to purification using a silica gel column (ethyl acetate/hexane=3/7→2/3) to obtain an intended oily product. After removing methanol, the resultant product was subjected to vacuum drying to obtain 1.1 g (2.6 mmol) of an intended disulfonic ester at a yield of 30%.

$^1$H-NMR (CDCl$_3$): δ5.14 (q, J=8, 2H), 3.80 (s, 6H), 3.30-3.16 (m, 4H), 2.01-1.88 (br, 4H), 1.62 (d, J=8, 6H), 1.56-1.49 (m, 4H). MS (DCI): m/z 419 (M+H)$^+$.

Synthesis Example 4: Synthesis of a Compound of Formula (D)

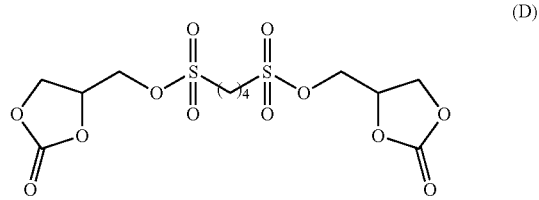

(D)

Into a 50 ml three-neck flask in a nitrogen gas atmosphere were charged 1.94 g (0.016 mol) of glycerol carbonate and 10 ml of THF to obtain a uniform solution. Then, 1.75 g (0.017 mol) of triethylamine was added to the solution while stirring, and the resultant mixture was cooled until the internal temperature became 3° C. using an ice bath. A solution of 2.0 g (0.008 mol) of 1,4-butanedisulfonyl chloride in 6 ml of THF was slowly dropwise added to the resultant mixture so that the internal temperature did not exceed 10° C. Then, the mixture was further stirred at an internal temperature of 5° C. for 2 hours. The ice bath was removed and the temperature of the mixture was increased to room temperature (27.2° C.), and 20 ml of water and 30 ml of ethyl acetate were added to the mixture, and then the deposited solid was collected by filtration. The solid was dissolved in an acetone:methanol mixed solvent (1:3 in a volume ratio), and stirred at 5° C. for 30 hours. An intended product was deposited in the form of a white powder. The deposited product was collected by filtration by means of suction, and washed with methanol, and then subjected to vacuum drying using a vacuum pump (at 25° C. for 12 hours) to obtain 2.76 g of an intended disulfonic ester (yield: 90.2%). The obtained compound had a high boiling point so that it could not be detected by a GC analysis. However, a $^1$H NMR analysis confirmed that an intended disulfonic ester free of an impurity was obtained.

$^1$H-NMR (CDCl$_3$, 400 MHz): δ5.12-5.07 (m, 2H), 4.60 (t, J=9, 2H), 4.51-4.42 (m, 4H), 4.30-4.26 (dd, J=6, 2H), 3.51-3.47 (m, 4H), 1.88-1.81 (m, 4H). MS (DCI): m/z 419 (M+H)$^+$.

Reference Synthesis Example 1: Production of a Compound of Formula (A)(Another Method 1)

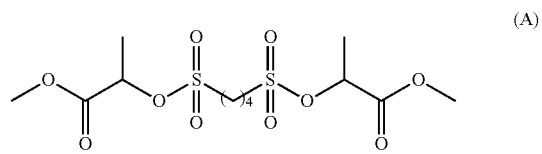

(A)

The production of a compound was conducted by substantially the same method as in Example 1 except the operation after a pale yellow oil was obtained. The obtained oil was cooled as such to an internal temperature of −20° C. using a dry ice/ethanol bath. However, a solid of an intended product was not able to be obtained. The pale yellow oil was subjected to vacuum drying using a vacuum pump (at 25° C. for 12 hours) to obtain 9.27 g of a pale yellow oil of an intended product (yield: 121.1%). The purity estimated from a GC analysis was 66.5%.

Reference Synthesis Example 2: Production of a Compound of Formula (A) (Another Method 2)

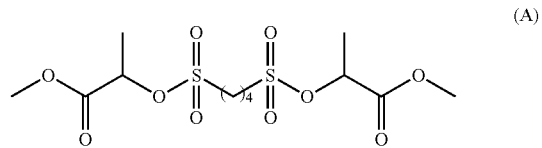

(A)

The production of a compound was conducted by substantially the same method as in Example 1 (on a three-fifth scale) except the operation after the obtained pale yellow oil was dissolved in methanol. The resultant methanol solution was stirred at room temperature (27° C.). However, a solid of an intended product was not be able to be obtained. The methanol solution was further concentrated using a water bath at 30° C. to obtain 4.99 g of a pale yellow oil of an intended product (yield: 108.7%). The purity estimated from a GC analysis was 87.8%.

The results of observations on the Synthesis Examples and Reference Synthesis Examples are shown in Table 1. It has been found that, by conducting crystal deposition, an intended sulfonic ester having a high purity is obtained. On the other hand, in Reference Synthesis Example 1, an intended product in the form of a solid was not obtained, and the obtained product remained in an oil form, and this oil contained the residual alcohol raw material and amine, and therefore the yield exceeded 100%. Consequently, the purity was as low as 66.5% In Reference Synthesis Example 2, deposition of a solid of an intended product was not recognized, and, even when the product was further subjected to vacuum concentration using a water bath at 30° C., deposition of a solid was not recognized. From these results, it is apparent that an intended product having a high purity cannot be obtained without crystal deposition after the reaction, and that an intended product cannot be obtained when a cooling operation is not performed after the product is dissolved in the solvent for crystal deposition.

TABLE 1

| | Crystal deposition solvent | Crystal deposition temperature | Yield | Purity |
|---|---|---|---|---|
| Synthesis Example 1 | MeOH | −20° C. | 63.6% | 99.3 Area % |
| Synthesis Example 2 | MEOH | −20° C. | 57.0% | 99.8 Area % |
| Synthesis Example 3 | — | — | 30.0% | 98.1 Area % |
| Synthesis Example 4 | Acetone/MeOH | 5° C. | 90.2% | Impurity undetected※ |
| Reference Synthesis Example 1 | None | −20° C. | 121.1% Pale yellow oil | 66.5 Area % |
| Reference Synthesis Example 2 | MeOH | 27° C. | 108.7% Pale yellow oil | 87.8 Area % |

※By $^1$H NMR

Example 1

Satisfactorily dried $LiPF_6$ was dissolved in a mixture of ethylene carbonate, dimethyl carbonate, and ethylmethyl carbonate (volume ratio: 3:3:4) in a dry argon atmosphere so that the $LiPF_6$ concentration of the resultant non-aqueous electrolytic solution became 1 mol/L (this electrolytic solution is frequently referred to as "reference electrolytic solution"). The compound represented by formula (A) obtained above in Synthesis Example 1 was added to the reference electrolytic solution so that the amount of the compound became 0.73% by mass, based on the mass of the resultant non-aqueous electrolytic solution (100% by mass), to prepare a non-aqueous electrolytic solution. Using the prepared electrolytic solution, a battery was produced by the above-mentioned method, and a cycle capacity maintaining ratio, high-temperature storage test, and low-temperature resistance characteristics were measured. The results are shown in Table 2.

Example 2

A battery was produced by substantially the same method as in Example 1 except that vinylene carbonate (hereinafter, referred to as "VC") was further added to the non-aqueous electrolytic solution in Example 1 so that the amount of the VC became 0.5% by mass, based on the mass of the resultant non-aqueous electrolytic solution (100% by mass), and a cycle capacity maintaining ratio, high-temperature storage test, and low-temperature resistance characteristics were measured. The results are shown in Table 2.

Example 3

A battery was produced by substantially the same method as in Example 1 except that, instead of the compound of formula (A), the compound of formula (B) in Synthesis Example 2 was added so that the amount of the compound became 1.03% by mass, based on the mass of the resultant non-aqueous electrolytic solution, and a cycle capacity maintaining ratio, high-temperature storage test, and low-temperature resistance characteristics were measured. The results are shown in Table 2.

Example 4

A battery was produced by substantially the same method as in Example 1 except that, instead of the compound of formula (A), the compound of formula (C) in Synthesis Example 3 was added so that the amount of the compound became 1.07% by mass, based on the mass of the resultant non-aqueous electrolytic solution, and a cycle capacity maintaining ratio, high-temperature storage test, and low-temperature resistance characteristics were measured. The results are shown in Table 2.

Example 5

A battery was produced by substantially the same method as in Example 1 except that, instead of the compound of formula (A), the compound of formula (D) in Synthesis Example 4 was added so that the amount of the compound became 0.78% by mass, based on the mass of the resultant non-aqueous electrolytic solution, and a cycle capacity maintaining ratio, high-temperature storage test, and low-temperature resistance characteristics were measured. The results are shown in Table 2.

Reference Example 1

A battery was produced by substantially the same method as in Example 1 except that, instead of the compound represented by formula (A), a compound represented by the formula (E) below was added so that the amount of the compound became 0.70% by mass, based on the mass of the resultant non-aqueous electrolytic solution (100% by mass), and a cycle capacity maintaining ratio, high-temperature storage test, and low-temperature resistance characteristics were measured. The thus obtained results are shown in Table 2.

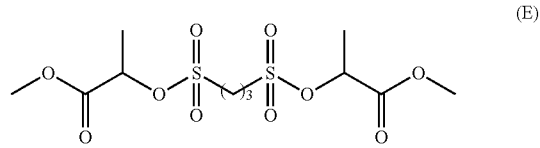

(E)

Reference Example 2

A battery was produced by substantially the same method as in Reference Example 1 except that VC was further added to the non-aqueous electrolytic solution in Reference Example 1 so that the amount of the VC became 0.5% by mass, based on the mass of the resultant non-aqueous electrolytic solution (100% by mass), and a cycle capacity maintaining ratio, high-temperature storage test, and low-temperature resistance characteristics were measured. The results are shown in Table 2.

Reference Example 3

A battery was produced by substantially the same method as in Example 1 except that, instead of the compound of structural formula (A), a compound of the formula (F) below was added so that the amount of the compound became 0.51% by mass, based on the mass of the resultant non-aqueous electrolytic solution, and a cycle capacity maintaining ratio, high-temperature storage test, and low-temperature resistance characteristics were measured. The results are shown in Table 2.

(F)

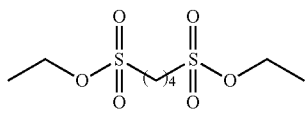

Reference Example 4

A battery was produced by substantially the same method as in Example 1 except that, instead of the compound of structural formula (A), a compound of the formula (G) below was added so that the amount of the compound became 0.71% by mass, based on the mass of the resultant non-aqueous electrolytic solution, and a cycle capacity maintaining ratio, high-temperature storage test, and low-temperature resistance characteristics were measured. The results are shown in Table 2.

(G)

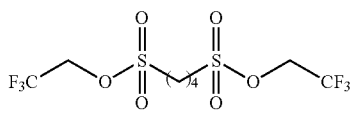

Comparative Example 1

A battery was produced by substantially the same method as in Example 1 except that, instead of the compound represented by formula (A), VC was added so that the amount of the VC became 0.50% by mass, based on the mass of the resultant non-aqueous electrolytic solution (100% by mass), and a cycle capacity maintaining ratio, high-temperature storage test, and low-temperature resistance characteristics were measured. The results are shown in Table 2.

Comparative Example 2

A battery was produced by substantially the same method as in Example 1 except that the compound of formula (A) was not used, and a cycle capacity maintaining ratio, high-temperature storage test, and low-temperature resistance characteristics were measured. The results are shown in Table 2.

TABLE 2

| | Compound 1 | Compound 2 | Cycle capacity maintaining ratio/% | High-temperature storage capacity maintaining ratio/% | Low-temperature resistance characteristics/Ω |
|---|---|---|---|---|---|
| Example 1 | [structure] | — | 94.9 | 95.3 | 17.2 |
| Example 2 | [structure] | — | 95.5 | 96.0 | 26.6 |
| Example 3 | [structure] | — | 94.6 | 95.3 | 19.4 |
| Example 4 | [structure] | — | 94.4 | 94.9 | 19.2 |
| Example 5 | [structure] | — | 94.1 | 95.2 | 16.2 |

TABLE 2-continued

| | Compound 1 | Compound 2 | Cycle capacity maintaining ratio/% | High-temperature storage capacity maintaining ratio/% | Low-temperature resistance characteristics/Ω |
|---|---|---|---|---|---|
| Reference Example 1 | (structure with I, two sulfonate groups linked by (CH₂)₃, methyl ester groups) | — | 94.8 | 95.1 | 26.9 |
| Reference Example 2 | (structure with I, two sulfonate groups linked by (CH₂)₃, methyl ester groups) | VC | 95.3 | 95.5 | 31.1 |
| Reference Example 3 | (structure with two sulfonate groups linked by (CH₂)₄, ethyl groups) | — | 92.6 | 94.4 | 21.5 |
| Reference Example 4 | (structure with two sulfonate groups linked by (CH₂)₄, F₃C-CH₂-O- groups) | — | 92.5 | 94.3 | 23.4 |
| Comparative Example 1 | — | VC | 94.5 | 95.1 | 27.2 |
| Comparative Example 2 | — | — | 92.7 | 94.6 | 23.4 |

As is apparent from Table 2, in Examples 1 and 2 using the non-aqueous electrolytic solution containing the compound represented by the formula (1) in the present invention, both very excellent cycle capacity maintaining ratio and very excellent low-temperature resistance characteristics are achieved, as compared to those in Comparative Examples 1 and 2. Further, Examples 3 to 5 show that the effects of the present invention can be obtained by the use of various compounds represented by the formula (1).

Reference Examples 1 and 2 show that, when a sulfonic ester of the formula (1) wherein Z has 3 carbon atoms was used, it was possible to improve the cycle capacity maintaining ratio; however, with respect to the low-temperature resistance characteristics, more excellent results were obtained in Examples 1 and 2 using a compound of the formula (1) wherein Z has 4 or more carbon atoms.

Reference Examples 3 and 4 show that, when a compound of the formula (1) wherein X has no oxygen atom was used, no effect of improvement of the cycle capacity maintaining ratio and low-temperature resistance characteristics was found.

The cycle test in the present Examples is conducted in an atmosphere at a temperature as high as 60° C., which means that the present invention is effective not only in improving the cycle capacity maintaining ratio but also in improving the high-temperature storage capacity maintaining ratio.

INDUSTRIAL APPLICABILITY

By using the non-aqueous electrolytic solution of the present invention, the cycle capacity maintaining ratio and low-temperature resistance characteristics of a non-aqueous electrolyte secondary battery can be improved. Therefore, the non-aqueous electrolytic solution of the present invention and the non-aqueous electrolyte secondary battery using the same can be used in known various applications.

Specific examples of applications include a laptop personal computer, a tablet personal computer, an electronic book player, a cell phone, a smartphone, a portable CD/DVD/BD player, a portable liquid crystal television set, a hand-held cleaner, a transceiver, an electronic organizer, a calculator, a memory card, a radio receiver, a backup power source, a motor, an automobile, a bike, a bicycle fitted with a motor, a bicycle, a lighting fixture, a toy, a video game machine, a clock, an electric tool, a camera, a load smoothing power source, and a natural energy-stored power source.

The invention claimed is:

1. A compound which is represented by the following formula (20):

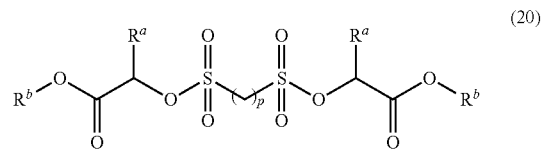

(20)

wherein:
$R^a$ each occurrence independently represents an alkyl group having 1 to 4 carbon atoms,
$R^b$ each occurrence independently represents an alkyl group having 1 to 4 carbon atoms, and
p represents an integer of 4 to 6.

2. The compound of claim 1, wherein $R^a$ independently represents a methyl or ethyl.

3. The compound of claim 1, wherein $R^b$ independently represents a methyl or ethyl.

4. The compound of claim 2, wherein $R^b$ independently represents a methyl or ethyl.

5. A non-aqueous electrolytic solution comprising an electrolyte and a non-aqueous solvent dissolving therein the electrolyte, the non-aqueous electrolytic solution containing the compound of claim 1.

6. The non-aqueous electrolytic solution according to claim 5, wherein the compound is contained in an amount of 0.01 to 5% by mass, based on 100% by mass of the non-aqueous electrolytic solution.

7. A non-aqueous electrolyte secondary battery comprising a negative electrode and a positive electrode each being capable of having occluded therein and releasing metal ions, and the non-aqueous electrolytic solution according to claim 6.

\* \* \* \* \*